US008679352B2

(12) United States Patent  
Olivier et al.

(10) Patent No.: US 8,679,352 B2  
(45) Date of Patent: Mar. 25, 2014

(54) METHOD AND SYSTEM FOR PROCESSING OF AQUATIC SPECIES

(75) Inventors: Laurent Olivier, Vero Beach, FL (US); Greg Havemann, Pearland, TX (US); Paul Antalik, Palm Bay, FL (US); Brandi Alderson, Melbourne, FL (US)

(73) Assignee: PA LLC, Melbourne, FL (US)

( * ) Notice: Subject to any disclaimer, the term of this patent is extended or adjusted under 35 U.S.C. 154(b) by 29 days.

(21) Appl. No.: 13/050,931

(22) Filed: Mar. 17, 2011
(Under 37 CFR 1.47)

(65) Prior Publication Data

US 2012/0110901 A1 May 10, 2012

Related U.S. Application Data

(60) Provisional application No. 61/314,736, filed on Mar. 17, 2010.

(51) Int. Cl.
*B01D 37/00* (2006.01)
*B01D 21/01* (2006.01)
*A01H 13/00* (2006.01)

(52) U.S. Cl.
USPC ............ 210/770; 210/723; 210/724; 210/806

(58) Field of Classification Search
None
See application file for complete search history.

(56) References Cited

U.S. PATENT DOCUMENTS

| 5,047,332 | A | 9/1991 | Chahal |
| 5,171,592 | A | 12/1992 | Holtzapple |
| 6,077,548 | A | 6/2000 | Lasseur |
| 6,096,546 | A * | 8/2000 | Raskin .......................... 435/410 |
| 6,251,643 | B1 | 6/2001 | Hansen |
| 2004/0030516 | A1* | 2/2004 | Dunhill et al. .................. 702/83 |
| 2008/0096267 | A1 | 4/2008 | Howard |
| 2010/0151558 | A1 | 6/2010 | Alianell |

FOREIGN PATENT DOCUMENTS

| WO | WO 98/18344 | 5/1998 |
| WO | WO 2007/109066 | 9/2007 |
| WO | WO 2008/033573 | 3/2008 |
| WO | WO 2010/123943 | 10/2010 |
| WO | WO 2010144877 | 12/2010 |

OTHER PUBLICATIONS

PCT International Preliminary Report on Patentability in corresponding International application No. PCT/US2011/028911, issued Sep. 18, 2012, 4 pages.
U.S. Appl. No. 61/171,036, filed Apr. 20, 2009, "Cultivation, Harvesting and Processing of Floating Aquatic Species With High Growth Rates".
U.S. Appl. No. 61/186,349, filed Jun. 11, 2009, "Vegetation Indices for Measuring Multilayer Microcrop Density and Growth".

* cited by examiner

*Primary Examiner* — Katherine Zalasky
(74) *Attorney, Agent, or Firm* — Kelley Drye & Warren, LLP

(57) ABSTRACT

Disclosed herein is a method and system of recovering multiple products from industrial-scale production of a biomass of an aquatic species.

35 Claims, 39 Drawing Sheets

Example Calculation of Product Yield

Example Calculation for Product Yield

Figure 28 Test Protocol Scenario

METHOD AND SYSTEM FOR PROCESSING OF AQUATIC SPECIES

CROSS REFERENCE TO RELATED APPLICATION

This application claims priority under 35 U.S.C. §119(e) to U.S. Provisional Application No. 61/314,736, filed on Mar. 17, 2010, which is hereby incorporated by reference in its entirety.

BACKGROUND

Marine protein sources are often utilized in feeds because they are an excellent source of essential amino acids, fatty acids, vitamins and minerals, and because they generally enhance palatability. Alternative ingredients can be used in the feed industry in place of fish meal. For this reason, many studies have been conducted on the replacement of expensive marine proteins with lower cost ingredients. Considerable attention has been devoted to the replacement of fish meal with plant protein; lemnae, as a natural protein source, has a better array of essential amino acids than most other vegetable proteins and resembles animal protein more closely. Newly harvested lemnae contain up to 43% protein by dry weight and can be used without further processing as a complete feed for fish. Compared with most other plants, lemnae leaves contain little fiber (5% in dry matter for cultivated plants) and little to essentially no indigestible material even for monogastric animals. This contrasts with the compositions of many crops such as soy beans, rice, and maize, approximately 50% of whose biomass comprises residues high in fiber and low in digestibility.

*Lemna* is a genus of free-floating aquatic plant from the duckweed family, also known as Lemnaceae family. These rapidly growing plants have found uses as a model system for studies in basic plant biology, in eco-toxicology, in production of biopharmaceuticals, and as a source of animal feeds for agriculture and aquaculture.

*Lemna* species grow as simple free-floating thalli on or just beneath the water surface. Most are small, not exceeding 5 mm in length, except *Lemna trisulca* which is elongated and has a branched structure. *Lemna thalli* have a single root. The plants grow mainly by vegetative reproduction. This form of growth can allow very rapid colonization of new water.

The rapid growth of duckweeds finds application in bioremediation of polluted waters and as test organisms for environmental studies. It is also being used as an expression system for economical production of complex biopharmaceuticals.

Dried duckweed can be a good cattle feed. It can contain 25-45% protein (depending on the growth conditions), 4.4% fat, and 8-10% fiber, measured by dry weight.

Duckweed can be farmed organically, with nutrients being supplied from a variety of sources, for example cattle dung, pig waste, biogas plant slurry, or other organic matter in slurry form.

SUMMARY

Embodiments of the present invention provide a process of recovering multiple products from biomass of an aquatic species. The process can include: providing the biomass; lysing the biomass to generate a lysed biomass; separating the lysed biomass to generate a juice and a first solid phase; forming a wet protein concentrate using the juice; drying the wet protein concentrate to generate a dry protein concentrate; producing a wet bio-crude using the first solid phase; drying the wet bio-crude to generate at least one product selected from a dry bio-crude and a carbohydrate-rich meal; wherein the multiple products can include products selected from the dry protein concentrate, dry bio-crude, and carbohydrate-rich meal, and wherein at least 50% of the protein in the multiple products is in the dry protein concentration. In some embodiments, the providing step can include: producing the biomass of an aquatic species on an industrial scale; and harvesting the biomass. In some embodiments, the separating step can include pressing the lysed biomass. Likewise, in some embodiments, the process can include filtering the juice to generate a filtered juice and a second solid phase; clarifying the filtered juice to generate a clarified juice and a third solid phase; coagulating protein from the clarified juice to generate a broth including the wet protein concentrate; and separating the wet protein concentrate from the broth.

In some embodiments, at least one of: the first solid phase, the second solid phase, the third solid phase, and the broth, can be used to recover the bio-crude and/or the carbohydrate-rich meal. The aquatic species can include, for example, a species of *Lemna*. The lysing can include using at least one of: a ball mill, a colloid mill, a knife mill, a hammer mill, a grinding mill, a puree machine, and a filter press. The pressing can include using at least one of a belt press, a fan press, a rotary press, a screw press, a filter press, and finisher press. The juice can include soluble protein. The process can include pressing at least one of the first solid phase, the second solid phase, or the third solid phase to generate a second juice and a bio-crude. In some embodiments, the second juice can be combined with the juice. Likewise, in some embodiments, the further pressing can be carried out using a screw press. In some embodiments, the process further can include drying the bio-crude. The drying can be carried out using at least one of: a spin flash dryer, a spray dryer, a drum dryer, a flash dryer, a fluid bed dryer, a double drum dryer, and a rotary dryer. The filtering can be carried out using at least one of: a vibratory separator, a vibrating screen filter, a circular vibratory separator, a linear/inclined motion shaker, a decanter centrifuge, and a filter press. The vibratory separator can include at least one vibrating screen filter. The clarifying can include centrifuging and/or further filtration of the filtered juice, such as, for example, at least one of a high-speed multi disc stack centrifuge, microfiltration, ultrafiltration, and the like.

In some embodiments, the clarified juice can be stored in a storage tank such as, for example, a chilled storage tank. The coagulating can include lowering the pH of the clarified juice, for example to below about 6, or to below about 5, or to about 4.5, or less. Lowering the pH can include using at least one acid selected from hydrochloric acid, nitric acid, sulfuric acid, and the like. The coagulating can be carried out using a precipitator including at least one heat exchanger, such as, for example, at least one plate, or tube, or steam injection heat exchanger, or the like. The coagulating can include heating the clarified juice to a first temperature to generate a broth; and cooling the broth to a second temperature. In some embodiments, the first temperature can be from about 40° C. to about 100° C., likewise, the second temperature can be below about 40° C. or below about 30° C., for example. The separating can include using a high speed multi-disk stack centrifuge. In some embodiments, the wet protein concentrate can be stored in a storage tank, such as, for example, a chilled storage tank. The process further can include drying the wet protein concentrate to generate a dry protein concentrate. The drying can be carried out using, for example, a spray dryer, a drum dryer, a spin flash dryer, a flash dryer, a fluid bed dryer, a double drum dryer, a rotary dryer, and the like. In some embodiments, the process further can include contacting a material selected from the group consisting of: the third solid phase and the clarified juice, with at least one of, for example, an alcohol, a solvent, water, and the like, and further contacting the material with an acid catalyst, to form a mixture, separating the mixture into a liquid and a solid, whereby lipids and ash-forming components, and the like, in the material are segregated into the liquid. The process further can include either before or directly after the lysing, washing the biomass using an aqueous solvent or the like.

Embodiments of the invention also provide systems of recovering multiple products from biomass of an aquatic species; such systems can include, for example: a lysing unit for lysing the biomass to generate a lysed biomass; a separating unit for separating the lysed biomass to generate a juice and a solid phase; a unit for forming a wet protein concentrate using the juice; a protein drying unit for drying the wet protein concentrate to generate a dry protein concentrate; and a unit for drying a wet bio-crude to generate at least one product selected from a dry bio-crude and carbohydrate-rich meal, wherein the wet bio-crude can include the solid phase; and wherein the multiple products can include products selected from, for example, the dry protein concentrate, dry bio-crude, carbohydrate-rich meal, and the like, and wherein at least about 50% of the protein in the multiple products is in the dry protein concentration. The lysing unit can include at least one apparatus selected from a colloid mill, knife mill, ball mill, hammer mill, grinding mill, puree machine, and filter press. The separating unit can include at least one apparatus selected from a belt press, decanter centrifuge, fan press, rotary press, screw press, filter press, and finisher press. The unit for forming the wet protein concentrate using the juice can include at least one unit selected from, for example, a filtering unit, a clarifying unit, a protein coagulation unit, and a protein collection unit. In some embodiments, the filtering unit can include at least one apparatus selected from, for example, a vibratory separator, a vibrating screen filter, a circular vibratory separator, a linear/inclined motion shaker, a decanter centrifuge, a filter press, and the like. The clarifying unit can include at least one apparatus or process selected from, for example, a high-speed disc stack centrifuge, microfiltration, ultra-filtration, and the like. In some embodiments, the protein coagulation unit can include at least one apparatus selected from, for example, a heat precipitator, an acid precipitation apparatus, and the like. The protein collection unit can include at least one apparatus selected from, for example, a high speed multi-disk stack centrifuge, a settling tank, a clarifier, a decanter centrifuge, and the like. The protein drying unit can include at least one apparatus selected from, for example, a spray dryer, double drum dryer, flash dryer, and the like. The unit for drying the bio-crude can include at least one apparatus selected from, for example, a fluid bed dryer, a spin flash dryer, a flash dryer, a drum dryer, a rotary dryer, and the like. Likewise, in some embodiments, the system can further include a sanitizing unit.

DETAILED DESCRIPTION

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Any discussion of the prior art throughout the specification should in no way be considered as an admission that such prior art is widely known or forms part of common general knowledge in the field.

Unless explicitly stated otherwise, throughout the description and the claims, the words "comprise(s)," "comprising," "include(s)," "including," and the like, are to be construed in an inclusive sense as opposed to an exclusive or exhaustive sense; that is to say, in the sense of "including, but not limited to."

Plant species in the Lemnaceae family (a.k.a. duckweed) grow prolifically in many regions of the world and, as such, have been studied extensively for potential industrial uses, including feed applications. Species in this family contain high levels of protein, ranging from ca. 15-43% (dry weight basis) offering potential value for feed applications which call for concentrated protein sources. Given this defining feature, the species can be suitable as an alternative protein source for aquaculture feeds, animal feeds, as well as other applications.

Figure 1A:
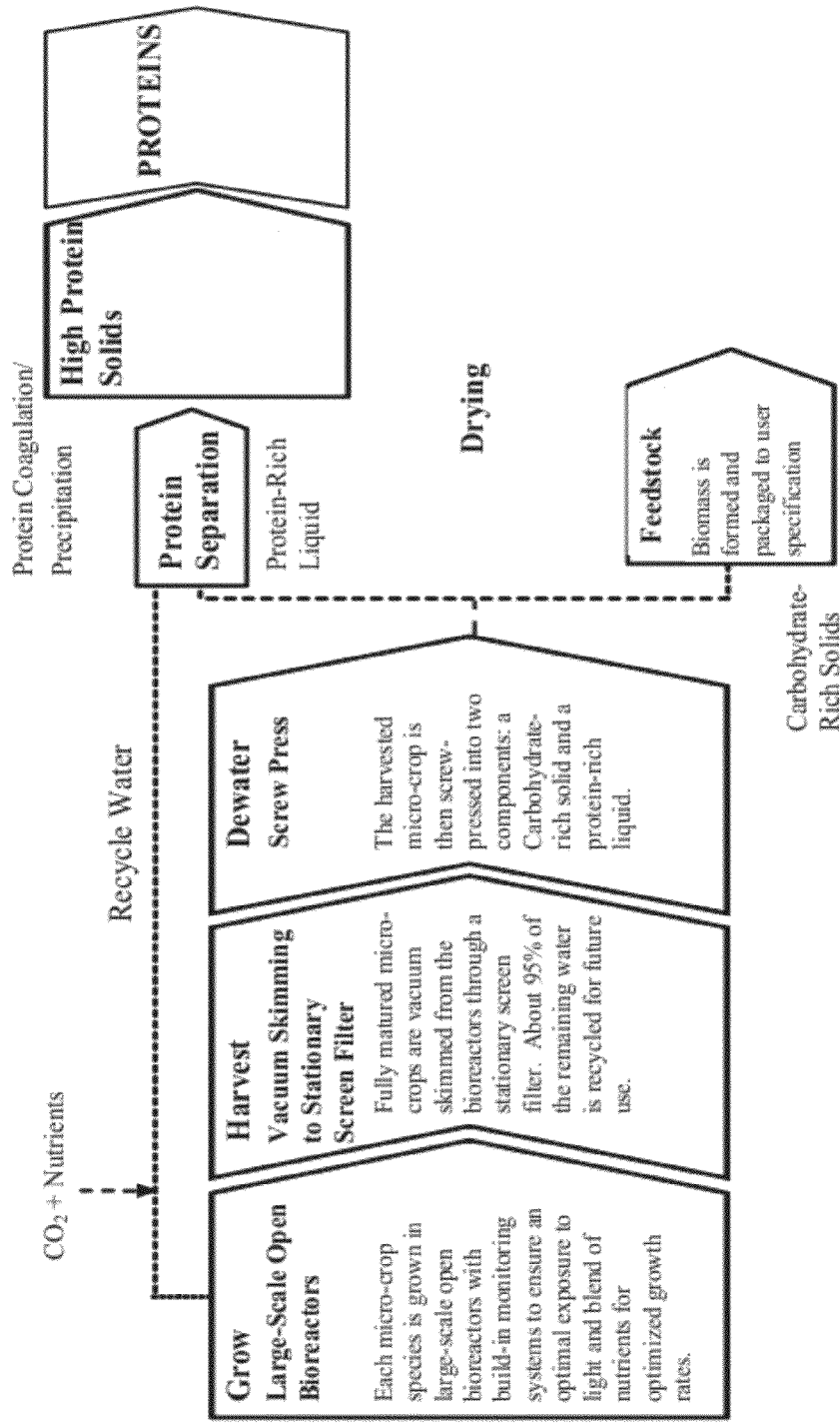
FIG. 1A is a flow diagram illustrating an exemplary lemnaceae production for biofuels feedstock and protein concentrate.

The current environment encompassing climate change and sustainable resources is driving development to commercialize materials from Lemnaceae as a feedstock for the biofuels industry and protein concentrate. FIG. 1A shows a flow diagram of an exemplary lemnaceae production for biofuels feedstock and protein concentrate. Carbohydrate can be separated from the substrate material for biofuels applications whereas the protein fraction (which also contains appreciable amounts of fat) can be utilized for feed applications. Notably, given the scale of the biofuels industry, commercialization of these processes can result in large scale availability of this sustainable protein source. Further, a protein concentrate containing up to 65%-70% protein (dry weight basis), or higher, can be obtained. Table 1 shows typical compositional, essential amino acid, and preliminary digestibility data of lemna which can illustrate the potential efficacy of this protein source for aquaculture feed applications.

TABLE 1

Essential Amino Acid Profile of
Lemna Protein Concentration

| Essential Amino Acid | Protein (g/100 g) |
| --- | --- |
| Lysine | 5.9 |
| Leucine | 9.7 |
| Isoleucine | 5.1 |
| Methionine | 2.4 |
| Phenylalanine | 6.3 |
| Threonine | 4.4 |
| Tryptophan | 2.0 |
| Valine | 6.3 |
| Histidine | 2.7 |
| Arginine | 6.8 |

As illustrated in FIG. 1A, an aquatic species, e.g. a micro-crop species such as lemnae, can be grown in a growth system. The growth system can comprise one or more bioreactors. The bioreactor(s) can be large-scale, medium-scale, or small-scale, or a combination thereof. The scale of the bioreactor(s) can be chosen based on the considerations including, e.g., the space available for constructing the growth system and/or the processing facilities, the source of water (or other growth media for the micro-crop species) supply, and the like. The bioreactor(s) can be an open bioreactor, a closed bioreactor, or a semi-open bioreactor, or a combination thereof. The growth system can comprise a monitoring system. The bioreactor(s) can comprise a built-in monitoring system. The monitoring system can adjust the operation conditions including, such as, for example, the flow rate of nutrients and/or $CO_2$ into the bioreactor(s), light exposure, time and/or rate of harvest, or the like, or a combination thereof. Such adjustment can be made in real time or periodically. Such adjustment can optimize growth rates and/or yield of the aquatic species. Merely by way of example, the micro-crop species is grown in large-scale open bioreactors with build-in monitoring systems to ensure an optimal exposure to light and blend of nutrients for optimized growth rates.

After the aquatic species matures, it can be harvested from the growth system. In some embodiments, as exemplified in FIG. 1A, the aquatic species, e.g., a micro-crop, can be harvested by vacuum skimming from the bioreactors through a stationary screen filter. In some embodiments, the biomass slurry including the harvested aquatic species with a large portion of water or any other growth medium can be conveyed to an inclined vibrating screen where the biomass comprising the aquatic species can be separated from the water or the growth medium by letting the water or the growth medium flow through the screen. At least 40%, or at least 50%, or at least 60%, or at least 70%, or at least 80%, or at least 90%, or at least 95% of the water or the growth medium collected by the vacuum can be recycled for future use. Merely by way of example, the recycled water or growth medium can be delivered back to the bioreactor and reused.

The harvested biomass comprising the aquatic species can be processed into two components: a carbohydrate-rich solid phase and a protein-rich liquid phase, also referred to as a juice. The procedure can be achieved using a screw press, a belt press, a knife mill, a ball mill, and the like, or a combination thereof. Merely by way of example, the harvested biomass can be lysed in a knife mill. As used herein, "lysing" biomass encompasses mechanical or chemical procedures that disturb the organization of the organism on the level of individual cells or multicellular structures, so as to render the carbohydrates, proteins, and micronutrients present in the biomass organisms more available for downstream processing to purified protein, carbohydrate-containing materials, or micronutrient-containing fluids. Lysing can include, for example, chopping, shredding, smashing, pressing, tearing, lysis by osmotic pressure, or chemical treatments that degrade biological structures. The lysed biomass can be pressed in a belt press to generate a juice and a first solid phase; and the first solid phase can be pressed in a screw press to generate more juice and a wet material, referred to as wet "bio-crude." The wet bio-crude can include the carbohydrate-rich solid phase, and can be processed further. The juice generated in different pressing procedures can be combined for further processing.

"Bio-crude" and "biocrude" are used interchangeably. The wet bio-crude can be processed based on considerations, such as, for example, suitability for further applications. Merely by way of example, the bio-crude can be dried to be used as a power plant feedstock. In other embodiments, the bio-crude can be optimized via pelletization or the like for co-combustion with other hydrocarbon-based fuels, such as coal. In other embodiments, the bio-crude is used as a feedstock for biofuel conversion. In other embodiments, the bio-crude is further processed using physical or chemical methods to further extract protein content. In further embodiments, the bio-crude can be processed via, for example, pelletization, to user specification.

As illustrated in FIG. 1A, in some embodiments, the juice comprising the protein-rich liquid phase is processed to coagulate and/or precipitate protein to generate high protein solids, which in some embodiments are further processed to generate protein of higher purity. The high protein solids are suitable for animal feed.

Figure 1B:
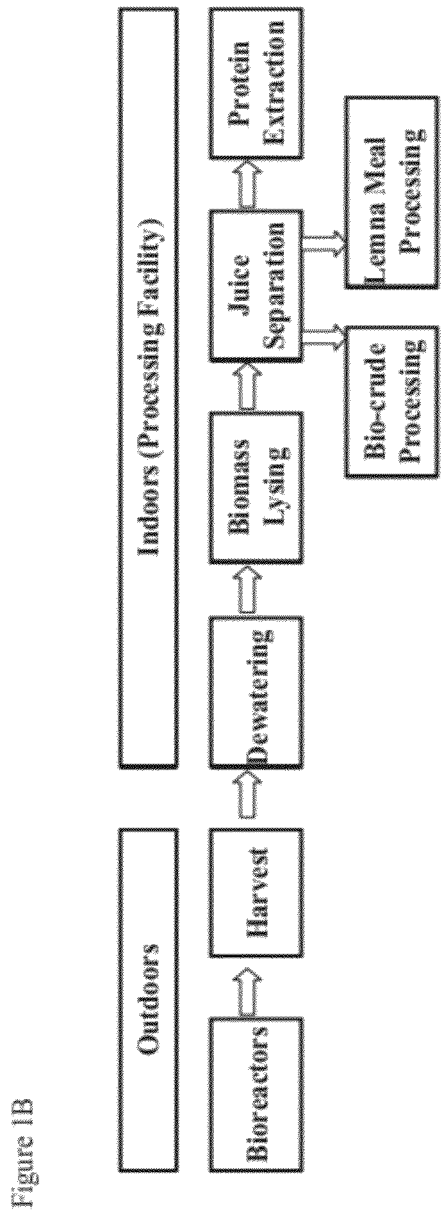
FIG. 1B is a block diagram illustrating an exemplary process of growing, harvesting and processing micro-crops.

FIG. 1B shows a block diagram of an exemplary process of growing, harvesting and processing micro-crops. This exemplary process is designed to take as input large volumes of "micro-crops", e.g., lemna, and output several products including a protein concentrate, a fuel feedstock (referred to as "bio-crude"), and a carbohydrate-rich animal feed (referred to as "lemna meal"). The amounts, yields, and distribution of product-outputs can be varied and designated by implementing specific protocols. FIG. 1B illustrates this in a basic block diagram. Other factors that can be optimized include identifying and utilizing as part of the process, unit operations that are scalable based on the intended outcome. This analysis includes whether the process is run in batch or continuous mode and can have an effect on the end-product and/or yields produced.

The exemplary process includes an outdoors part and an indoors part. The exemplary process starts with the bioreactors which are production ponds designed to provide optimum growth conditions for the production of surface micro-crops. An automated system monitors the nutrient levels and controls a specified recipe of nutrients in the ponds. During harvest, an automated skimmer system withdraws specified amounts of the micro-crop from designated areas in the ponds and transfers the biomass via a pumping system into an inclined vibrating screen to separate the wet biomass from water and debris. More than 99% of the water is recycled back into the ponds via a return manifold to provide uniform mixing throughout the pond. The wet biomass is collected and conveyed to the Processing center (an indoor processing facility). Once entering the processing facility, the wet biomass is lysed (by a ball mill, hammer mill, or other similar milling technologies) to release the internal water. The juice stream that results is protein-rich and undergoes further processing for the extraction of protein resulting in a protein concentrate suitable as an ingredient for animal feed and potentially human food. The soluble protein in the juice is coagulated using a heat precipitator, acid precipitation or similar type of technology. The protein precipitate is then separated using a high speed multi-disk stack centrifuge. The supernatant liquid is recycled back to the ponds while the wet protein concentrate is dried using a dryer chosen specifically for optimizing the end product (including a spray dryer, drum dryer, etc.). The dried product is then packaged. The material remaining after the juice extraction is a carbohydrate-rich slurry. This slurry is further processed to result in any one of the following bio-crude used for combustion, bio-crude used as a coker feedstock (for a refinery) or lemna meal used as an animal meal. Each application has specified (and different) end-product characteristics that determine the acceptable quality. These include particle size, moisture content, ash content, etc. The drying mechanism varies and is chosen to improve or optimize these characteristics based on the end product. In some instances further processing can be applied to reduce ash content. The procedure for ash removal (if utilized) is further described elsewhere in the application.

In some embodiments, in the selection of a surface micro-crop, a dominant local species with selected compositional and growth characteristics that have historically developed within the local environmental conditions is chosen. Dominant local species can out-compete other species in open ponds or bioreactors (and sometimes even in closed environments or bioreactors). The selection procedure starts with choosing several species from local ponds and lakes, and investigating their growth and product potentials (i.e., composition). The mix of dominant species can vary by season. This identifies potential micro-crops which are grown in different seasons and climates. A few local species are selected. The desired colonies are generated from the selections for use in larger-scale outdoor production.

In some embodiments, the bioreactor (e.g., the pond) is an earthen basin with the embankments made of compacted dirt removed from the interior bottom of the bioreactor. Multiple bioreactors are lined and designed to provide optimal conditions for lemna growth (including nutritional availability, water quality, etc.). The bioreactor has dimensions chosen to optimize capital expenses and operational expenses to produce the highest volume of material retrieved. The surface area is designed to accommodate typical rainfall for a specific area. Excess water is designed to run into a storm water storage container (e.g., a storm water storage pond).

In some embodiments, a micro-crop grows rapidly and forms a floating mat on the water surface of the bioreactor (e.g., the pond). In order to maintain uniform nutrient levels and the desired temperature throughout the bioreactor, various recirculation techniques (propulsion systems, paddle wheels, etc.) are utilized and controlled to create an improved growing conditions for the mat population. During recirculation, the water quality can be monitored and if needed essential nutrients, which include a balanced proportion of all macro- and micro-nutrition that the micro-crop needs, are added to keep nutrition within set levels.

In some embodiments, the growth medium includes water. The water includes balanced nutrition for the micro-crop. In other embodiments, one or more nutrients that the micro-crop needs are added to the growth medium. Merely by way of example, the growth medium includes well water that has acceptable water quality and then the proper amount of balanced nutrition.

In some embodiments, smaller bioreactors (i.e., ponds) are designed and sized to adequately serve as "feeder" bioreactors to a larger bioreactor. The smaller bioreactors are first inoculated and grown to high density at which point they can optimally seed the larger bioreactor in a manner that supports a more rapid growth.

In some embodiments, a growth medium (e.g., water) is added to a bioreactor (e.g., a pond) and is maintained at a certain set-point level. For optimal micro-crop (or biomass) productivity, the water is monitored to maintain the nutrients and compositions within standard levels. Sensors are installed in the bio sensor to monitor and record the levels of the nutrients and compositions including, for example, ammonia, pH, oxidation reduction potential (ORP), and temperature, and the like, or a combination thereof. The ammonia sensor is used as feedback to control the levels of nitrogen in the bioreactor via the nutrient tank injection system. A liquid level transmitter is installed in the bioreactor to assure that the water level does not fall below the desired depth.

In some embodiments, the bioreactor is equipped with one or more sensors to monitor and control various aspects including water quality, nutrients, environmental conditions, and the like, or a combination thereof. These parameters are both monitored and controlled via dedicated control systems comprising PLCs and data management systems.

For optimal micro-crop (or biomass) productivity, the thickness of the micro-crop mat is monitored and maintained at a desired thickness. Harvesting can take place through several physical mechanisms and at varying times throughout the year (based on environmental conditions and the corresponding growth of the specific species).

In some embodiments, when the desired harvesting conditions are met, the micro-crop mat is transported over the skimmers and pumped to a vibrating screen where the micro-crop is separated and collected in a hopper for further processing. The water runoff is collected and recycled back into the pond.

The harvest procedure is controlled via a programmable logic controller (PLC) and human/machine interface (HMI).

Additional discussion regarding choosing a micro-crop species, and growing and harvesting it can be found at, for example, U.S. Patent Application Publication Nos. 20080096267, filed Mar. 15, 2007, and PCT Application Publication No. WO 2007109066, filed Mar. 15, 2007, all entitled "SYSTEMS AND METHODS FOR LARGE-SCALE PRODUCTION AND HARVESTING OF OIL-RICH ALGAE;" U.S. Patent Application Publication No 20100151558, filed Mar. 12, 2009, and PCT Application Publication No. WO 2008033573, filed Sep. 13, 2007, both entitled "TUBULAR MICROBIAL GROWTH SYSTEM;" U.S. Provisional Application No. 61/171,036, filed Apr. 20, 2009, and PCT Application Publication No. WO 2010123943, filed Apr. 20, 2010, both entitled "CULTIVATION, HARVESTING AND PROCESSING OF FLOATING AQUATIC SPECIES WITH HIGH GROWTH RATES;" and U.S. Provisional Application No. 61/186,349, filed Jun. 11, 2009, PCT Application Publication No. WO 2010144877, filed Jun. 11, 2010, both entitled "VEGETATION INDICES FOR MEASURING MULTI-LAYER MICROCROP DENSITY AND GROWTH." All of the foregoing patent applications are hereby incorporated by reference.

The method and system of recovering multiple products from industrial-scale production of a biomass described herein can be customized to produce the desired product specifications with a specific specie/specie mix of micro-crop used as supply. For the purpose of illustration, lemna (indigenous to Florida) is referenced from this point forward. In some portion of the application, lemna is also referred to as *Lemna*. The products discussed below include a protein concentrate (suitable for, for example, animal feed) and a carbohydrate-rich stream that can be processed into "bio-crude" (suitable for, for example, fuel feedstock) or an animal feed supplement that is referred to as "lemna meal." This is for illustration purposes only, and is not intended to limit the scope of the application. A person of ordinary skill in the art would understand that the method and/or system described herein are suitable for processing other micro-crops or species. Merely by way of example, the method and/or system of processing are suitable to processing algae, duckweed, watermeal, mosquito fern, salvinia, water lettuce, or the like, or a specific specie/specie mix of micro-crop whose industrial-scale feedstock supply is readily available.

Some advantages of the method and system of recovering multiple products from industrial-scale production of a biomass described herein include at least the following. The method and system can effectively recover commercially valuable products (e.g., dry protein concentrate, dry bio-crude suitable for fuel feedstock, animal meal or fish meal, etc.) from cheap raw feedstock. The method and system can be eco-friendly. The raw feedstock can include a specie or specie mix that can be indigenous and/or fast-growing. In addition, a lot of the residues of the process (e.g., water, liquor generated in the process, and the like) can be recycled with or without treatment. Merely by way of example, when a biomass including an aquatic species is harvested for processing, a significant amount of water (or any other growth medium) can be removed from the biomass and can be reused as, for example, growth medium, with or without treatment. The method and system are suitable for industrial-scale operation.

As used herein, "industrial-scale" or "industrial scale" indicates that the method and system are commercially feasible or viable for processing a large amount of raw feedstock. Merely by way of example, the method and system described herein have the capacity to process at least 100 kg, or at least 500 kg, or at least 1000 kg, or at least 1500 kg, or at least 2000 kg, or at least 2500 kg, or at least 3000 kg or more of raw feedstock a day, and can run on a continuous mode or a batch mode.

Embodiments of the present invention provide a process of recovering multiple products from biomass of an aquatic species. The process can include: providing the biomass; lysing the biomass to generate a lysed biomass; separating the lysed biomass to generate a juice and a first solid phase; forming a wet protein concentrate using the juice; drying the wet protein concentrate to generate a dry protein concentrate; producing a wet bio-crude using the first solid phase; drying the wet bio-crude to generate at least one product selected from a dry bio-crude and a carbohydrate-rich meal; wherein the multiple products can include products selected from the dry protein concentrate, dry bio-crude, and carbohydrate-rich meal, and wherein at least 50% of the protein in the multiple products is in the dry protein concentration.

A raw feedstock can be harvested from a growth system as described above. The raw feedstock can comprise the biomass and water or a growth medium from the growth system.

The biomass can include at least one of the following properties: fast growing, cheap to culture, harvest and process, high in protein, eco-friendly, or the like. In certain embodiments, the biomass can include lemnae, algae, duckweed, watermeal, mosquito fern, salvinia, water lettuce, and the like, or a combination thereof.

The raw feedstock can be transported using, e.g., an inclined vibratory screen, from a bioreactor to a dewatering station. The dewatering station can be located either inside a main processing building or facility, or near the bioreactor itself, depending on the customer/site-specific needs or the size of the facility. The water can flow through the screen, while the wet biomass can be conveyed down the screen. Separation of water from the wet biomass can be enhanced by, for example, low amplitude vibration. The water can be pumped back into the bioreactor. Optionally, before the water is pumped back into the bioreactor, its nutrients level or compositions can be measured, and/or modified if desired. The screen can deposit the wet biomass into a collection system where the wet biomass is then conveyed and fed into the milling unit operation. The dewatering phase can include multiple passes and/or types of dewatering methods other than the inclined vibratory screen.

In some embodiments, "dewater" can refer to the procedure of removing water from the raw feedstock. In some embodiments, "dewater" can refer to the procedure of removing a juice (e.g., a protein-rich juice) from a solid phase.

In some embodiments, the lysing is achieved in a mechanical way (also referred to as milling), for example, by milling, grinding, or shredding the biomass to generate a lysed biomass. That is, the milling can essentially tears, grinds, and shears the biomass and biomass fronds to lyse the cell walls, allowing for water, protein, and other components to be exposed and therefore available. Interchangeable unit operations include a ball mill, colloid mill, knife mill, hammer mill, grinding mill, puree machine, filter press, and the like, or a combination thereof.

A ball mill can function by having a horizontal or vertical cylinder spinning on its axis with grinding media inside. Merely by way of example, the rotation speed is 1 Hz, 10 Hz, or 20 Hz, or 30 Hz, or 40 Hz, or 50 Hz, or 60 Hz, or 70 Hz, or 80 Hz, or 90 Hz, or 100 Hz, or higher than 100 Hz, or from 1 Hz to 10 Hz, or from 10 Hz to 30 Hz, or from 30 Hz to 50 Hz, or from 50 Hz to 70 Hz, from 70 Hz to 90 Hz, from 90 Hz to 120 Hz. Typical grinding media can include balls that are comprised of ceramic, stainless steel, glass, and the like, or a combination thereof. The grinding media can be rotated by the circular motion of the ball mill. As the grinding media is lifted along the internal wall, the media can then fall back down, smashing the lemna. The constant motion of the balls moving against each other can also provide a grinding effect which helps mill the lemna.

A colloid mill can function by introducing lemna into a spinning series of grooves that provide a high amount of friction and shear. Those forces can then act to shear the lemna apart.

A knife mill can use a horizontal rotating shaft on which blades are mounted. The rotor can be spun at high speed while material is fed via a small feed hopper built internally. The material can be shredded and expelled through a screen at the bottom of the mill. This unit can essentially shear the lemna fronds to expose the internal cell structure, allowing more water and protein to be removed.

A hammer mill can operate similarly to a knife mill, but instead of blades, large blunt paddles can be used. The paddles can press the lemna against a serrated screen, creating high stress and shear that can then act to break the plant structure apart. Once the structure is sufficiently destroyed, some or essentially all internal components can be available for extraction.

Exemplary apparatuses for milling or lysing the wet biomass, e.g., lemna, are described for illustration purposes only, and are not intended to limit the scope of the application. A person of ordinary skill in the art, reading the description, would understand other apparatuses can be employed to perform the milling or lysing function.

In certain embodiments, the biomass is fed to the lysing (or milling) procedure at a constant rate, while in other embodiments it is fed at a variable rate. In some embodiments, the biomass is fed to the lysing (or milling) procedure continuously, while in other embodiments it is fed intermittently. The feeding rate and/or mode can be determined based on the considerations including, the target production rate, apparatus(es) employed in the process, property of the feedstock, and the like, or a combination thereof. In some embodiments, the feeding rate is at least 10 kg/hour, or at least 50 kg/hour, or at least 100 kg/hour, or at least 200 kg/hour, or at least 300 kg/hour, or at least 400 kg/hour, or at least 500 kg/hour, or at least 600 kg/hour, or at least 700 kg/hour, or at least 800 kg/hour, or at least 900 kg/hour, or at least 1000 kg/hour, or higher than 1000 kg/hour. In some embodiments, the feeding rate is from 10 kg/hour to 200 kg/hour, or from 200 kg/hour to 400 kg/hour, or from 400 kg/hour to 600 kg/hour, or from 600 kg/hour to 800 kg/hour, or from 800 kg/hour to 1000 kg/hour, or higher than 1000 kg/hour.

In some embodiments, chemical methods are employed to lyse the wet biomass. In particular embodiments, the lysing is performed by changing the pH value of the wet biomass. The pH value can be raised to higher than 7.0, or higher than 7.5, or higher than 8.0, or higher than 8.5, or higher than 9.0, or higher than 9.5, or higher than 10.0. The pH value of the wet biomass can be maintained from 7.0 to 7.5, or from 7.5 to 8.0, or from 8.0 to 8.5, or from 8.5 to 9.0, or from 9.0 to 9.5, or from 9.5 to 10.0. The pH value of the wet biomass can be maintained from 7.0 to 14.0, or from 7.0 to 13.0, or from 7.0 to 12.0, or from 7.0 to 11.0, or from 7.0 to 10.0, or from 7.0 to 10.5, or from 7.0 to 10.0, or from 7.0 to 9.5, or from 7.0 to 9.0, or from 7.0 to 8.5, or from 7.0 to 8.0, or from 7.0 to 7.5. The pH value can be lowered to below 7.0, or below 6.5, or below 6.0, or below 5.5, or below 5.0, or below 4.5, or below 4.0, or below 3.5, or below 3.0. The pH value of the wet biomass can be maintained from 3.0 to 3.5, or from 3.5 to 4.0, or from 4.0 to 4.5, or from 4.5 to 5.0, or from 5.0 to 5.5, or from 5.5 to 6.0, or from 6.0 to 6.5, or from 6.5 to 7.0. The pH value of the wet biomass can be maintained from 3.0 to 7.0, or from 3.5 to 7.0, or from 4.0 to 7.0, or from 4.5 to 7.0, or from 5.0 to 7.0, or from 5.5 to 7.0, or from 6.0 to 7.0, or from 6.5 to 7.0. In certain embodiments, the feedstock comprising the lysed biomass and the water or the growth medium after the lysing procedure is fed directly to the next procedure for isolating protein; in other embodiments, the feedstock is neutralized before fed to the next procedure for isolating protein and/or other product(s).

In other embodiments, the lysing is achieved using a combination of mechanical and chemical methods.

In some embodiments, the lysing is performed at room temperature, or at atmospheric pressure. In other embodiments, the lysing is performed at elevated temperatures or pressures.

In some embodiments, the lemna biomass goes through a sanitization procedure (e.g., washing) either before or after the lysing procedure in order to remove toxins either adhering to the surface of or incorporated into the lemna during the growth of the organisms. This can be accomplished by bringing the lemna biomass into contact with a solution or solvent, either by submersion, spraying, or other methods known in the art. The solution or solvent can be an aqueous solution or solvent. The solution or solvent can be at an elevated temperature. The solution or solvent can be sprayed at high pressure. In an embodiment, water is employed as the solution or solvent. Several wash steps are possible. In some embodiments, the lemna biomass is first brought into contact with a solution or solvent containing one or more ingredients commonly used for the washing of crops, such as fatty acids, alcohols, or chlorine. After exposure to this solution or solvent, the biomass is then washed again with water. This solution or solvent can act as a disinfectant and can significantly reduce the amount of micro-organisms such as bacteria, viruses, and mold. The level of reduction of such micro-organisms is dependent on the factors including, for example, the concentration of oxidizing agents, contact time, and the like, or a combination thereof.

Merely by way of example, after dewatering, the wet biomass including lemna goes through sanitization. A sanitizing unit separates out macroscopic debris and larger environmental organisms such as plants and animals (if applicable or desirable). The lemna is then rinsed with water dosed with an oxidizing solution or solvent. This solution or solvent can act as a disinfectant and can significantly reduce the amount of micro-organisms such as bacteria, viruses, and mold. The level of reduction of such micro-organisms is dependent on the factors including, for example, the concentration of oxidizing agents, contact time with the lemna, and the like, or a combination thereof.

In some embodiments, the milled or lysed lemna are separated into a first solid phase and juice. In some embodiments, unlysed lemna (e.g., lemna obtained from dewatering without the milling or lysing procedure) are processed to separate the first solid phase and juice. In some embodiments, a mixture of milled or lysed lemna and unlysed lemna are processed to separate the first solid phase and juice. The purpose is to provide an efficient way of handling large input capacities while performing the separation, where the maximum amount of soluble protein can continue with the lemna juice stream. Interchangeable unit operations include a decanter centrifuge, belt press, fan press, rotary press, screw press, filter press, finisher press, and the like, or a combination thereof.

A decanter centrifuge can operate by pumping the mixture including the solids and juice into a spinning cylinder. As the centrifugal force pushes the solids against the outer wall, an internal rotating scroll can move the solids against the wall towards the discharge at one end. The solids discharge end can have a diminishing radius along with the scroll to match the diminishing size. As the solids move up the ramp created by the diminishing radius, the solids can be removed from the pond depth inside the bowl, allowing for additional dewatering. The dewatered solids can then be ejected continuously. The juice can be pushed towards the other end of the decanter through centrifugal force, and during its travel to the other side, can have solids removed via centrifugal force.

A belt press can use mechanical compression by having milled or lysed lemna introduced between two taut belts with small micron size openings. The belts can then pass through a series of rollers that squeeze the juice out through the openings in the belt. The caked solids can then be ejected where the two belts separate at the end of the unit operation. The juice can drip into pans at the bottom of the unit where using gravitational force it can be ejected through a common opening and sent downstream for further processing.

The screw press can use mechanical compression to squeeze out the internal juice from the lysed biomass fronds. A screw press can operate by introducing material into a device that resembles a screw auger. The rotating shaft on the screw press can convey the material into the equipment, where as the material progresses, the fighting, or distance between the threads of the screw, gets smaller or the shaft getting wider. As the flighting decreases in distance, the total volume in between the threads decreases, creating a compression effect. The lemna can be compressed between these flights and juice can be expelled. The rotating shaft can be encased by a mesh screen of small micron size that can hold the wet bio-crude in the screw but allow the juice to be expelled. Removal of the juice can decrease the overall moisture content of the wet bio-crude.

A filter press can operate by using a positive displacement pump and pumping the milled or lysed lemna into a series of filter chambers. The filter chambers can have small micron size openings that can push juice and water out using the pressure of the positive-displacement pump. Once enough solids have accumulated inside the filter and juice cannot be extracted further, a "squeeze" can be introduced by injecting water or air into bladders in between the filter chambers, creating additional pressure on the filter cake. As the bladders push outwards, additional pressure can be exerted on the filter chambers as the walls push inwards. Additional liquid (e.g., juice) can be liberated. Once the juice is sufficiently removed, the filter press chambers can be opened and a solid filter cake can be ejected where the solids proceed downstream for further processing, e.g., bio-crude processing and/or lemna meal processing.

A finisher press can operate similar to the screw press, but instead of a screw with threads, there is a rotating shaft with paddles that can push the material along a screen size. The remaining solid phase of the material can then be ejected out of the finisher press.

In certain embodiments, the separating procedure is performed at a constant rate, or at a variable rate. The separating procedure is performed continuously, or intermittently.

In certain embodiments, the separating procedure is performed at room temperature, or at atmospheric pressure. In other embodiments, the separating procedure is performed at elevated temperatures or atmospheric pressures.

In some embodiments, the separating procedure comprises one stage separating, and the wet bio-crude includes the first solid phase. In other embodiments, the separating procedure comprises two-stage separating, or three- or more-stage separating, in which the first solid phase is further processed to extract more juice from it, and the solid phase generated in one stage can be fed to the next separating stage. Multiple stages of separating can be performed using the same separating apparatus. At least one stage can be performed using a different separating apparatus than the other stage or stages. Further removal of the juice from the first solid phase have one or more benefits including, decreased overall moisture content of the wet bio-crude, a lower operational expenses and capital expenses for the bio-crude dryer, increased efficiency of recovering juice from the biomass; improved efficiency of recovering protein from the biomass, and the like.

Merely by way of example, the biomass is pressed in a belt press to generate a juice and a first solid phase; and the first solid phase is pressed in a screw press to generate more juice and a wet bio-crude. In some embodiments, the belt press is the primary pressing stage (or primary juice separation stage) for the biomass. The biomass, lysed (or milled), or unlysed, or a combination thereof, is pumped from a hopper between two perforated belt filters. These belts carrying the biomass in between are passed through a series of rollers. As the belts pass through the rollers, internal juice is expelled from the biomass to generate a juice and a first solid phase. The expelled juice comprises water as well as water-soluble compounds, such as soluble protein and minerals. Once through the press, the first solid phase is removed, for example, by scraping. In certain embodiments, the first solid phase is fed into a secondary pressing stage. In certain embodiments, a screw press is used at the secondary pressing stage. The screw press employs the mechanical compression of a screw to squeeze out remaining internal juice from the first solid phase to generate a juice and a wet bio-crude. In some embodiments, the juice generated here is combined with the juice generated in the primary pressing stage and/or in any other pressing stage(s) for further processing. After passing through the screw press, the pressed solids, i.e., the wet bio-crude, are collected, for example in large mobile hoppers, for further processing by, for example, drying.

As another example, the biomass, lysed (or milled), or unlysed, or a combination thereof, is fed to a decanter centrifuge for the primary separation to obtain a juice and a first solid phase. The first solid phase is fed to one or more mechanical pressing stages for further separating the juice from the first solid phase. The juice obtained from the centrifuge and from the one or more mechanical pressing stages is combined for further processing. If one mechanical pressing stage is employed, the wet bio-crude is obtained from the mechanical pressing. If more than one mechanical pressing are employed, the solid phase generated in one pressing stage can be fed to the next pressing stage, and the wet bio-crude is obtained from the last pressing stage. The one or more mechanical pressing stages can be performed using a pressing apparatus including, a belt press, screw press, filter press, and the like, or a combination thereof.

Exemplary apparatuses for separating the juice and solid phase of the biomass, e.g., lemna, are described for illustration purposes only, and are not intended to limit the scope of the application. A person of ordinary skill in the art, reading the description, would understand other apparatuses can be employed to perform the function.

In some embodiments, the juice generated by the separating procedure is filtered to generate a filtered juice and a second solid phase. Several different interchangeable unit operations can be used to filter the coarse solids out of the juice. These unit operations include using, for example, a circular vibratory separator, linear/inclined motion shaker, decanter centrifuge, filter press, and the like, or a combination thereof.

A circular vibratory separator can operate and remove excess solids by introducing the liquid stream (e.g., the juice) onto a vibrating circular bed. The bed can contain a filter mesh where the liquid can pass through and the solids can remain on the screen. The circular motion of the vibration can allow for the solids to be pushed towards the outer wall of the circular bed, vibrating and dewatering continuously. The solids can then be ejected through a side-port where they can be recycled or processed with the wet bio-crude. The fluid that passes through the first screen can undergo a second (or third) screening with a smaller mesh screen underneath. At the end the liquid (e.g., the filtered juice) is collected in a solid vessel at the bottom of the unit and expelled where it can be pumped further downstream for further processing.

A linear (or inclined) motion shaker can operate very similar to the circular vibratory separators, but instead of the material being pushed towards the outer wall of the circle, the solids can continuously vibrate along the path of the linear shaker until being discharged at the other end. Liquid can pass through the filter screens just as with the circular vibratory separators to form a filtered juice, and is pumped downwards for further processing.

A decanter centrifuge can be used. The liquid with solids can be introduced into a cylindrical unit that is rotating, producing centrifugal force. The solids can be pushed to the outside wall and where a rotating scroll conveys the solids towards the outlet. The juice can be discharged at the other end where the centrifugal force continues to separate the solids from the liquid to form a filtered juice.

A filter press, described elsewhere in the application, can also be used to remove the solids from the liquid (e.g., the juice) to form a filtered juice.

Merely by way of example, the filtering can be performed using a filter. In some embodiments, a 106-micrometer vibrating screen filter is used. A filter with a mesh size other than 106 micrometers, or filters of other than a vibrating-type can also be used. Suitable mesh sizes for the filtering procedure include smaller than 1000 micrometers, or smaller than 800 micrometers, or smaller than 600 micrometers, or smaller than 500 micrometers, or smaller than 400 micrometers, or smaller than 300 micrometers, or smaller than 200 micrometers, or smaller than 180 micrometers, or smaller than 150 micrometers, or smaller than 120 micrometers, or smaller than 100 micrometers, or smaller than 90 micrometers, or smaller than 80 micrometers, or smaller than 70 micrometers, or smaller than 60 micrometers, or smaller than 50 micrometers, or smaller than 40 micrometers, or smaller than 30 micrometers, or smaller than 20 micrometers.

In certain embodiments, the filtering is performed at room temperature, or at atmospheric pressure. In other embodiments, the filtering is performed at elevated or lowered temperatures or pressures or vacuum.

In certain embodiments, the second solid phase is fed to the separating procedure. In other embodiments, the second solid phase is combined with the wet bio-crude generated by the separating procedure for further processing. In particular embodiments, the water content of the wet bio-crude is less than 90%, or less than 80%, or less than 70%, or less than 60%, or less than 50%, or less than 40% by weight.

In some embodiments, the filtered juice is clarified to generate a clarified juice and a third solid phase. This clarifying procedure can be a final separation of smaller particles in the filtered juice that are not removed in the filtering procedure prior to protein purification. This procedure can also be referred to as polishing. This procedure can be optional, depending on the specific needs of the product of interest. These remaining solids can be very small in particle size. The filtered juice can be clarified using, for example, a high-speed disc stack centrifuge, microfiltration, ultra-filtration, and the like, or a combination thereof. When a centrifuge is used to clarify the filtered juice, the clarified juice generated by the clarifying procedure can also be referred to as a spun-filtered juice.

A high-speed disc stack centrifuge can be used. The filtered juice can be pumped into the centrifuge where the centrifugal force can push the filtered juice outwards along a path of slanted discs. The solids can be pushed on the downward slope of the discs and the juice is pushed upwards along the discs to the outlet. Solids can be discharged either continuously or intermittently. The discharged solids form the third solid phase, and the discharged juice forms the clarified juice.

A microfiltration and an ultra-filtration can use a porous membrane to separate out the unwanted particles based on particle size. The size and type of filter media can be varied to selectively separate out different components from the filtered juice.

The clarifying procedure can capture a large portion of the carbohydrates as well as fiber in the third solid phase. In some embodiments, the third solid phase is fed to a separating apparatus, for example, a decanter, a belt press, a screw press, and the like, to further recover protein in the third solid phase, thereby reducing protein losses. In other embodiments, the third solid phase can be combined with the wet bio-crude for further processing.

In some embodiments, the clarified juice is pumped into a storage tank, for example, a chilled storage tank, until further processing. The chilled storage tank is maintained at a temperature below room temperature. In particular embodiments, the chilled storage tank is maintained at a temperature below 50° C., or below 40° C., or below 30° C., or below 25° C., or below 20° C., or below 15° C., or below 10° C., or below 5° C., or below 2° C. Storage of the clarified juice at a low temperate until further processing can reduce proteolytic activity, and therefore, can improve the protein recovery efficiency through the further processing described below. The juice formed in the clarifying procedure can be referred to "clarified juice" or "polished juice." For example, the juice formed in the clarifying procedure is referred to as "polished juice" before it enters the storage tank (e.g., the juice tank), and referred to as "clarified juice" after it exits the storage tank (e.g., the juice tank). See, for example, FIG. 37. In other embodiments, the clarified juice is fed directly to further processing without being stored in a storage tank.

A protein-containing liquid can be processed to coagulate protein from it to generate a broth comprising a wet protein concentrate. This procedure can also be referred to as protein precipitation. Protein precipitation can be accomplished using heat treatment, acid treatment, or various other methods. The protein-containing liquid can include the clarified (or polished) juice, the filtered juice (if no clarifying procedure is performed), and the like. In some portion of the application, the protein-containing liquid refers to the clarified juice.

In some embodiments, the protein in the clarified juice is coagulated by acid treatment (also referred to as acid precipitation), thereby lowering the pH of the clarified juice. The pH can be lowered to below 7.0, or below 6.5, or below 6.0, or below 5.5, or below 5.0, or below 4.5. The lowered pH of the clarified juice can cause certain proteins to coagulate and precipitate out of the clarified juice to generate a broth comprising a wet protein concentrate.

The pH of the clarified juice can be lowered using, for example, hydrochloric acid, sulfuric acid, or the like, or a combination thereof. The acid can be added in the form in which it is used in the procedure. Alternatively, the acid can be generated in situ. In exemplary embodiments in which hydrochloric acid is used, the acid can be provided in the form of anhydrous hydrochloric acid, or can be generated in situ by adding both sulfuric acid and sodium chloride to the clarified juice.

The temperature of the clarified juice with lowered pH can be maintained at room temperature, or below room temperature. Merely by way of example, the temperature can be maintained below 30° C., or below 25° C., or below 20° C., or below 15° C., or below 10° C., or below 5° C., or below 0° C.

In other embodiments, the protein in the clarified juice can be coagulated by temperature manipulation. In this specification, the procedure will be referred to as heat coagulation or heat precipitation. In particular exemplary embodiments, the clarified juice can be pumped at a regulated flow rate into a heat precipitator (similar to a heat exchanger) that contains a series of heat exchangers. The heat exchangers can be plate or tube-in-tube heat exchangers. Heat can be introduced by a heating medium including, for example, heating oil, water, steam, and the like, or a combination thereof. The heating medium and the clarified juice can interact in either co-current or counter-current manner. As used herein, the co-current manner indicates that the temperature gradient of the flow of the heating medium is essentially in the same direction as that of the flow of the clarified juice in the heat precipitator; and the counter-current matter indicates that the temperature gradient of the flow of the heating medium is essentially in the opposite direction to that of the flow of the clarified juice in the heat precipitator. In the heat precipitator, the clarified juice can be heated to a first temperature from 40° C. to 100° C., or from 50° C. to 95° C., or from 60° C. to 90° C., or from 70° C. to 90° C., or from 80° C. to 85° C. In the heat precipitator, the clarified juice can be heated to a first temperature higher than 40° C., or higher than 50° C., or higher than 60° C., or higher than 70° C., or higher than 80° C. The heated clarified juice can then be quickly cooled to a second temperature below 100° C., or below 90° C., or below 80° C., or below 70° C., or below 60° C., or below 50° C., or below 40° C., or below 30° C. The cooling can be accomplished in less than 60 minutes, or less than 50 minutes, or less than 40 minutes, or less than 30 minutes, or less than 20 minutes, or less than 15 minutes, or less than 10 minutes, or less than 5 minutes, or less than 3 minutes, or less than 2 minutes, or less than 1 minute. This heating and cooling can force the protein to coagulate and precipitate out of the clarified juice to generate a broth including the wet protein concentrate. It is understood that the heating and/or cooling can be performed in an apparatus other than that described above.

As used herein, "broth" refers to the mixture including a wet protein concentrate that is generated by the protein coagulation by, e.g. acid treatment, or heat coagulation (or heat precipitation), or the like, or a combination thereof.

The protein in the clarified juice can be coagulated by a combination of pH change and temperature change. In particular exemplary embodiments, the protein in the clarified juice can be coagulated by temperature manipulation to generate a broth comprising the wet protein concentrate. The broth, before or after partial removal of the wet protein concentrate, can then go through a secondary protein coagulation by dropping the pH of the broth to precipitate at least some of the protein remaining in the broth.

In some embodiments, the broth including the wet protein concentrate can be further processed to collect a wet protein concentrate. The remaining liquid phase is referred to as "liquor." This can be achieved by, for example, filtering, centrifuging, or the like, or a combination thereof. Merely by way of example, the wet protein concentrate is collected from the broth by filtering using a membrane filter.

In other exemplary embodiments, a high speed multi-disk stack centrifuge is used. The protein wet concentrate can be separated from the supernatant liquid (referred to as "liquor") by centrifuging. Inside the centrifuge, the liquor is forced to the top of the centrifuge by centripetal force and can be pumped out, while the denser wet protein concentrate can be collected at the bottom and can be periodically or continuously ejected from the centrifuge. The liquor can go through the protein coagulation procedure and/or separating procedure described above for a second time to further recover the protein content. After undergoing these procedures, the liquor can be discarded or recycled to the growth system.

The wet protein concentrate separated from the broth can be washed using, for example, water, to remove impurities. This washing procedure is optional. Merely by way of example, water is added to the wet protein concentrate and mixed for a certain mixing time sufficient to achieve desired mixing. The amount and/or condition (e.g., temperature, pH, active cleaning agent, or the like, or a combination thereof) of the water can be chosen to optimize the operation. The water can also include an active cleaning agent if desired. The washed wet protein concentrate can be collected from the mixture of the wet protein concentration and washing water using, for example, a high-speed disc-stack centrifuge, settling tank (or clarifier), decanter centrifuge, or the like, or a combination thereof.

The mixture of the wet protein concentrate and the washing water can undergo another centrifuge using, for example, a high-speed disc-stack centrifuge, where the wash liquor (or supernatant) is removed and the washed wet protein concentrate is ejected.

A settling tank or clarifier can operate by introducing the mixture of the wet protein concentrate and the washing water into a tank where the coagulated proteins agglomerate. Heavier particles containing protein are separated from the wash liquor by gravity sedimentation. The settling tank or clarifier can include a series of plates and/or trays designed to enhance the separation. The wash liquor is discharged at the location on the tank that can facilitate an optimized protein recovery (removal from the mixture).

The washed wet protein concentrate can then be dried using a protein dryer.

The wet protein concentrate separated from the broth, or washed wet protein concentration if the washing procedure is employed, can be chilled for storage to reduce degradation and maintain high quality until further processing including, for example, evaporation, drying, and the like, or a combination thereof. Merely by way of example, the wet protein concentrate (or washed wet protein concentrate is stored in a chilled storage tank until further processing. The chilled storage tank can be maintained at a temperature below room temperature. In particular embodiments, the chilled storage tank is maintained at a temperature below 50° C., or below 40° C., or below 30° C., or below 25° C., or below 20° C., or below 15° C., or below 10° C., or below 5° C., or below 0° C., or below −5° C., or below −10° C.

The wet protein concentration (or washed wet protein concentrate) can contain high moisture content (or water content), depending on the combination of previous unit operations. High moisture content (or water content) can directly impact the capital expenditures and operational expenditures of the process, including, for example, the protein drying operation. Different moisture contents (or water contents) can also affect the types of protein dryers that are suitable. Optionally, an evaporating procedure can be included to lower the moisture content (or water content) of the wet protein concentration (or washed wet protein concentrate) before the drying procedure. Evaporation can be performed by, for example, a mechanical means, thermal (evaporative) means, or the like, or a combination thereof. Merely by way of example, the evaporation are performed using, a filter press, an evaporator, or the like, or a combination thereof.

An evaporator can remove moisture and/or volatiles from a material stream (e.g., the wet protein concentrate, or washed wet protein concentrate). The evaporator can be chosen based on the physical and morphological properties of the wet protein concentrate (or washed wet protein concentrate). Exemplary styles or types of evaporators include a rising film evaporator, falling film evaporator, natural circulation evaporator (vertical or horizontal), agitated-film evaporator, multiple-effect evaporator, and the like. Heat can be supplied directly into the evaporator, or indirectly through a heat jacket. The heat can either come from a raw source (e.g., combustion of natural gas, propane, etc., or steam from a boiler) or from a waste heat stream (dryer exhaust). By removing moisture from the wet protein concentrate (or washed wet protein concentrate), the moisture content (or water content) can be decreased, thus reducing the overall amount of water that needs to be removed at the protein drying operation.

In some embodiments, the wet protein concentrate is dried to generate dry protein concentrate. The drying procedure can reduce the moisture content of the wet protein concentrate (or washed wet protein concentrate, with or without the evaporating procedure) to the desired levels. The temperature of the drying procedure may not exceed the value that may damage vital characteristics of the product of interest. The dry protein concentrate can be used as a fish meal, animal feed, feedstock for further processing (e.g., pelletization), or the like, or a combination thereof. Merely by way of example, the dry protein concentrate is used as a feedstock to generate protein product with higher protein concentration for human use. In particular, the dry protein concentrate of certain embodiments is an effective replacement for soy protein isolates, which are presently used in a large number of human food products.

The drying procedure can be performed using, for example, a spray dryer, double drum dryer, flash dryer, or the like, or a combination thereof. In some embodiments, the inlet temperature (the temperature at the entrance to the dryer) is above or above 25° C., or above 50° C., or above 75° C., or above 100° C., or above 125° C., or above 150° C., or above 175° C., or above 200° C., or above 225° C., or above 250° C., or above 275° C., or above 300° C., or above 325° C., or above 350° C., or above 375° C., or above 400° C., or above 425° C., or above 450° C., or above 475° C., or above 500° C. In some embodiments, the inlet temperature is from 25° C. to 50° C., or from 50° C. to 75° C., or from 75° C. to 100° C., or from 100° C. to 125° C., or from 125° C. to 150° C., or from 150° C. to 175° C., or from 175° C. to 200° C., or from 200° C. to 225° C., or from 225° C. to 250° C., or from 250° C. to 275° C., or from 275° C. to 300° C., or from 300° C. to 325° C., or from 325° C. to 350° C., or from 350° C. to 375° C., or from 375° C. to 400° C., or from 400° C. to 425° C., or from 425° C. to 450° C., or from 450° C. to 475° C., or from 475° C. to 500° C., or above 500° C. In some embodiments, the inlet temperature is from 50° C. to 100° C., or from 100° C. to 150° C., or from 150° C. to 200° C., or from 200° C. to 250° C., or from 250° C. to 300° C., or from 300° C. to 350° C., or from 350° C. to 400° C., or from 400° C. to 450° C., or from 450° C. to 500° C., or above 500° C. In some embodiments, the outlet temperature (the temperature at the exit from the dryer) is below 300° C., or below 275° C., or below 250° C., or below 225° C., or below 200° C., or below 175° C., or below 150° C., or below 125° C., or below 100° C., or below 75° C., or below 50° C., or below 25° C. In some embodiments, the outlet temperature is from 300° C. to 275° C., or from 275° C. to 250° C., or from 250° C. to 225° C., or from 225° C. to 200° C., or from 200° C. to 175° C., or from 175° C. to 150° C., or from 150° C. to 125° C., or from 125° C. to 100° C., from 100° C. to 75° C., or from 75° C. to 50° C., or from 50° C. to 25° C., or below 25° C. In some embodiments, the outlet temperature is from 300° C. to 250° C., or from 250° C. to 200° C., or from 200° C. to 150° C., or from 150° C. to 100° C., from 100° C. to 50° C., or from 50° C. to 25° C., or below 25° C.

A spray dryer can operate by pumping the feed through either a nozzle or an atomizer, for the purpose of creating small droplets containing protein that have increased surface area (or increased surface area to volume ratio). The increased surface area (or increased surface area to volume ratio) can allow for drying with improved efficiency. Hot air injected directly into the drying chamber can dry the droplets containing protein that can then be carried pneumatically by the air into a collection vessel such as a cyclone, bag-house, or the like, or combination thereof. Merely by way of example, the wet protein concentrate (or washed wet protein concentrate) is conveyed from a chilled storage or from the centrifuge or other upstream apparatus into a spray dryer. The spray dryer can use a high-speed centrifugal atomizer to spray a fine mist into a heated drying chamber. The fine mist can create more surface area, and therefore, increase the drying efficiency. The water can evaporate as the small particles fall to the bottom. The dry protein concentrate, also referred to as dry protein meal, can then be collected using a cyclone separator, a bag-house, or the like, or a combination thereof.

A double drum dryer can operate by rotating two cylinders in opposite directions. The wet protein concentrate (or washed wet protein concentrate) can be injected onto the surface of the cylinders, or drums, which can be heated indirectly with steam. The direct contact with the heated surface can dry the wet protein concentrate (or washed wet protein concentrate). The flakes (or dry protein concentrate) can then be scraped off the surface of the cylinder drums and collected.

A flash dryer can drop the wet protein concentrate (or washed wet protein concentrate) into a closed loop system with hot air injected tangentially to the outside of the loop. The heated air can convey the wet protein concentrate (or washed wet protein concentrate) along the outer edge of the loop, drying continuously and reducing particle size. Once the particle size and moisture content (or water content) are reduced to the desirable levels, the product (dry protein concentrate) can be pneumatically transferred to a collection apparatus such as a cyclone, bag-house, or the like, or combination thereof.

In some embodiments, a back-mixing procedure is employed when, for example, moisture content (or water content) of the wet protein concentrate (or washed wet protein concentrate) is higher than what the specific dryer can accept as input. Back-mixing is performed by mixing dried final product (dry protein concentrate) with the wet protein concentrate (or washed wet protein concentrate) to enhance the solids content that is conveyed into the dryer.

In some embodiments, the dry protein concentrate that exits the dryer is packed and/or sealed in either an industry-standard bag or drum of varying sizes. A sealing method of industry-standard can be used to ensure proper shelf-life and shipping conditions. The bag or drum can include printed instructions or specifications regarding, for example, its intended use, shelf-life, suggested storage conditions, shipping conditions, compositions, or the like, or a combination thereof.

In some embodiments, the wet protein concentrate (or washed wet protein concentrate) is subjected to a drying procedure to reduce the moisture content (or water content) to generate a dry protein concentrate. The moisture content (or water content) of the dry protein concentrate is below 40%, or below 30%, or below 20%, or below 10%, or below 5% by weight of the dry protein concentrate. The solids content of the dry bio-crude is at least 60%, or at least 70%, or at least 80%, or at least 90%, or at least 95% by weight of the dry bio-crude.

In some embodiments, the protein concentration (or purity) of the dry protein concentrate can be from 30% to 95%, or from 40% to 90%, or from 50% to 85%, or from 60% to 80%, or from 70% to 75% by weight of the dry protein concentrate. In some embodiments, the protein concentration (or purity) of the dry protein concentrate is higher than 30%, or higher than 40%, or higher than 50%, or higher than 60%, or higher than 70%, or higher than 75%, or higher than 80% by weight of the dry protein concentrate. The remainder of the dry protein concentrate can include carbohydrates, minerals, and the like, or a combination thereof.

In some embodiments, the dry protein concentrate includes one or more essential amino acids. In some embodiments, the dry protein concentrate includes one or more amino acids selected from leucine, isoleucine, lysine, methionine, phenylalanine, theronine, tryptophan, valine, histidine, arginine, aspartic acid, serine, glutamic acid, proline, glycine, alanine, tyrosine and cysteine. In some embodiments, the concentration of one essential amino acid is at least 1 g/100 g of dry protein concentrate, or at least 1.5 g/100 g of dry protein concentrate, or at least 2 g/100 g of dry protein concentrate, or at least 2.5 g/100 g of dry protein concentrate, or at least 3 g/100 g of dry protein concentrate, or at least 4 g/100 g of dry protein concentrate, or at least 5 g/100 g of dry protein concentrate, or at least 6 g/100 g of dry protein concentrate, or at least 7 g/100 g of dry protein concentrate, or at least 8 g/100 g of dry protein concentrate, or at least 9 g/100 g of dry protein concentrate, or at least 10 g/100 g of dry protein concentrate. In some embodiments, the concentration of one essential amino acid is evaluated by percentage weight of the protein purified from the dry protein concentrate, and is at least 1 g/100 g of protein, or at least 1.5 g/100 g of protein, or at least 2 g/100 g of protein, or at least 2.5 g/100 g of protein, or at least 3 g/100 g of protein, or at least 4 g/100 g of protein, or at least 5 g/100 g of protein, or at least 6 g/100 g of protein, or at least 7 g/100 g of protein, or at least 8 g/100 g of protein, or at least 9 g/100 g of protein, or at least 10 g/100 g of protein.

In some embodiments, the dry protein concentrate includes a fat content lower than 50%, or lower than 40%, or lower than 30%, or lower than 25%, or lower than 20%, or lower than 15%, or lower than 10%, or lower than 5%, or lower than 4%, or lower than 3%, or lower than 2%, or lower than 1% by weight of the dry protein concentrate. In some embodiments, the dry protein concentrate includes a fat content from 1% to 10%, or from 10% to 20%, or from 20% to 30%, or from 30% to 40%, or from 40% to 50% by weight of the dry protein concentrate. In some embodiments, the dry protein concentrate includes a fat content from 1% to 50%, or from 2% to 40%, or from 5% to 30%, or from 8% to 20%, or from 10% to 15% by weight of the dry protein concentrate. The dry protein concentrate can be further processed to meet a desired fat content.

In some embodiments, the dry protein concentrate includes an ash content lower than 50%, or lower than 40%, or lower than 30%, or lower than 25%, or lower than 20%, or lower than 15%, or lower than 10%, or lower than 5%, or lower than 4%, or lower than 3%, or lower than 2%, or lower than 1% by weight of the dry protein concentrate. In some embodiments, the dry protein concentrate includes an ash content from 1% to 10%, or from 10% to 20%, or from 20% to 30%, or from 30% to 40%, or from 40% to 50% by weight of the dry protein concentrate. In some embodiments, the dry protein concentrate includes an ash content from 1% to 50%, or from 2% to 40%, or from 3% to 30%, or from 3% to 20%, or from 3% to 15%, or from 3% to 10%, or from 5% to 10%, or from 5% to 15% by weight of the dry protein concentrate. The dry protein concentrate can be further processed to meet a desired ash content.

In some embodiments, the dry protein concentrate includes a carbohydrate content lower than 50%, or lower than 40%, or lower than 30%, or lower than 25%, or lower than 20%, or lower than 15%, or lower than 10%, or lower than 5%, or lower than 4%, or lower than 3%, or lower than 2%, or lower than 1% by weight of the dry protein concentrate. In some embodiments, the dry protein concentrate includes a carbohydrate content from 1% to 10%, or from 10% to 20%, or from 20% to 30%, or from 30% to 40%, or from 40% to 50% by weight of the dry protein concentrate. In some embodiments, the dry protein concentrate includes a carbohydrate content from 1% to 50%, or from 2% to 40%, or from 5% to 30%, or from 8% to 20%, or from 10% to 15% by weight of the dry protein concentrate. The dry protein concentrate can be further processed to meet a desired carbohydrate content.

In some embodiments, the dry protein concentrate includes a fiber content lower than 20%, or lower than 15%, or lower than 10%, or lower than 8%, or lower than 5%, or lower than 4%, or lower than 3%, or lower than 2%, or lower than 1% by weight of the dry protein concentrate.

Merely by way of example, the dry protein concentrate produced by the process described herein include the following contents summarized in Table 2.

TABLE 2

Exemplary Contents of Dry Protein Concentrate Product

|  | Product 1 | Product 2 | Product 3 |
| --- | --- | --- | --- |
| % Solids | ≥90 | ≥88-90 | ≥95 |
| % Moisture | ≤10 | ≤12-10 | ≤5 |
| % Protein | ≥50 | from 60 to 80 | ≥65-75 |
| % Fat | ≤20 | from 5 to 20 | ≤5-15 |
| % Ash | ≤15 | from 1 to 10 | ≤2-10 |
| % Carbohydrate | ≤20 | from 5 to 20 | ≤10-15 |
| % Fiber | ≤10 | ≤5 | ≤5 |
| % other | 10 | 5-20 | 10-15 |

In some embodiments, other characteristics of the dry protein concentrate, e.g., the particle size, bacterial specification, or the like, or a combination thereof, are suitable for the intended purpose. In some embodiments, standard plate count of bacteria is lower than 100,000 cfu/g, or lower than 80,000 cfu/g, or lower than 60,000 cfu/g, or lower than 50,000 cfu/g, or lower than 40,000 cfu/g, or lower than 30,000 cfu/g, or lower than 25,000 cfu/g, or lower than 20,000 cfu/g, or lower than 15,000 cfu/g. In some embodiments, the meal does not include detectible level of E. coli. In some embodiments, the meal does not include detectible level of salmonella. In some embodiments, the meal includes yeast/mold of lower than 500/g, or lower than 400/g, or lower than 300/g, or lower than 250/g, or lower than 200/g, or lower than 150/g, or lower than 100/g, or lower than 50/g.

The wet bio-crude can be generated by any one or a combination of the following procedures described above: the lysing procedure, the separating procedure, the filtering procedure, and the clarifying procedure. The wet bio-crude can be processed as described above to further extract protein content. The wet bio-crude can be further processed by, for example, drying, to desired characteristics (e.g., a desired particle size and/or moisture content) for other applications. The dry bio-crude can be used as a power plant feedstock, a feedstock for biofuel conversion, or the like, or a combination thereof. The dry bio-crude can be further processed, e.g., by pelletization, for storage or application. The bio-crude drying can be performed using, for example, a fluid bed dryer, spin flash dryer, flash dryer, drum dryer, rotary dryer, or the like, or a combination thereof. In some embodiments, the inlet temperature (the temperature at the entrance to the dryer) is above or above 25° C., or above 50° C., or above 75° C., or above 100° C., or above 125° C., or above 150° C., or above 175° C., or above 200° C., or above 225° C., or above 250° C., or above 275° C., or above 300° C., or above 325° C., or above 350° C., or above 375° C., or above 400° C., or above 425° C., or above 450° C., or above 475° C., or above 500° C. In some embodiments, the inlet temperature is from 25° C. to 50° C., or from 50° C. to 75° C., or from 75° C. to 100° C., or from 100° C. to 125° C., or from 125° C. to 150° C., or from 150° C. to 175° C., or from 175° C. to 200° C., or from 200° C. to 225° C., or from 225° C. to 250° C., or from 250° C. to 275° C., or from 275° C. to 300° C., or from 300° C. to 325° C., or from 325° C. to 350° C., or from 350° C. to 375° C., or from 375° C. to 400° C., or from 400° C. to 425° C., or from 425° C. to 450° C., or from 450° C. to 475° C., or from 475° C. to 500° C., or above 500° C. In some embodiments, the inlet temperature is from 50° C. to 100° C., or from 100° C. to 150° C., or from 150° C. to 200° C., or from 200° C. to 250° C., or from 250° C. to 300° C., or from 300° C. to 350° C., or from 350° C. to 400° C., or from 400° C. to 450° C., or from 450° C. to 500° C., or above 500° C. In some embodiments, the outlet temperature (the temperature at the exit from the dryer) is below 300° C., or below 275° C., or below 250° C., or below 225° C., or below 200° C., or below 175° C., or below 150° C., or below 125° C., or below 100° C., or below 75° C., or below 50° C., or below 25° C. In some embodiments, the outlet temperature is from 300° C. to 275° C., or from 275° C. to 250° C., or from 250° C. to 225° C., or from 225° C. to 200° C., or from 200° C. to 175° C., or from 175° C. to 150° C., or from 150° C. to 125° C., or from 125° C. to 100° C., from 100° C. to 75° C., or from 75° C. to 50° C., or from 50° C. to 25° C., or below 25° C. In some embodiments, the outlet temperature is from 300° C. to 250° C., or from 250° C. to 200° C., or from 200° C. to 150° C., or from 150° C. to 100° C., from 100° C. to 50° C., or from 50° C. to 25° C., or below 25° C.

A fluid bed dryer can operate and dry material (e.g., the wet bio-crude) by introducing it onto a vibrating bed with heated air passing directly or indirectly to the material. The vibration and air can create a fluidized suspension of the material that can increase the surface area to be dried. This effect can make fluid bed drying an efficient and scalable solution to drying wet bio-crude to the desired characteristics.

A spin flash dryer can dry wet bio-crude into an agitated vat that causes the material to be suspended and as air pressure creates a suspension effect. Size-reduced particles can then be carried through a classifier at the top of the drying chamber carried by air flow into a collection apparatus such as a cyclone, bag-house, or the like, where the material is then collected.

A flash dryer can operate by having the wet bio-crude introduced into a closed loop. Hot air can be injected tangentially along the walls of the loop that can force the wet bio-crude to travel continuously in the loop, drying along the wall. By having the material roll along the wall driven by the air flow, a particle-size reducing effect can be created—once the size of the particles is small enough, the particles can flow freely off the air and be carried along an exhaust pipe located at the inside portion of the loop to a collection apparatus such as a cyclone, bag-house, or the like, to be collected.

A drum dryer can be a large vessel. It can be operated in either batch mode, continuous mode, or semi-continuous mode. The vessel, once activated, can tumble along an axis where heat can be applied directly into the vessel or indirectly through a heating jacket on the vessel. Hot air can be introduced directly into the vessel to dry the wet bio-crude directly; or heating oil can be introduced into the heating jacket of the vessel for indirect heating (and/or drying). The wet bio-crude can be tumbled until the moisture content (or water content) is reduced sufficiently enough and then be removed either in batch mode or continuous mode.

A rotary dryer is a long cylindrical dryer where the wet bio-crude can be introduced at one end, and either gravitationally, or pneumatically conveyed to the opposite end of the dryer. Heat can be applied either directly with hot air blowing co-currently or counter-currently into the dryer, or indirectly using heated oil in a heating jacket surrounding the outer layer of the dryer.

Merely by way of example, a spin flash dryer is used to dry the wet bio-crude. The wet bio-crude can be collected in mobile hoppers, and fed to the spin flash dryer. In the spin flash dryer, the wet bio-crude is dropped into the agitated feed vat of the spin flash dryer, and then fed to a drying chamber equipped with a spinning mixer. Hot air can flow through the wet bio-crude as the mixer breaks up any large clumps of wet bio-crude. The wet, heavy bio-crude can be kept in the drying chamber until the water content is low enough for the bio-crude to be light enough to be carried into the cyclone separator by the flow of hot air. The dry bio-crude can then be collected at the bottom of the cyclone.

In some embodiments, the wet bio-crude is subjected to the drying procedure to reduce the moisture content (or water content) to generate a dry bio-crude. The moisture content (or water content) of the dry bio-crude is below 40%, or below 30%, or below 20%, or below 10%, or below 5% by weight of the dry bio-crude. The solids content of the dry bio-crude is at least 60%, or at least 70%, or at least 80%, or at least 90%, or at least 95% by weight of the dry bio-crude.

In some embodiments, the dry bio-crude includes a protein content lower than 50%, or lower than 40%, or lower than 30%, or lower than 25%, or lower than 20%, or lower than 15%, or lower than 10%, or lower than 5% by weight of the dry bio-crude. In some embodiments, the dry bio-crude includes a protein content from 1% to 10%, or from 10% to 20%, or from 20% to 30%, or from 30% to 40%, or from 40% to 50% by weight of the dry bio-crude. In some embodiments, the dry bio-crude includes a protein content from 1% to 50%, or from 5% to 40%, or from 5% to 30%, or from 5% to 20%, or from 5% to 15%, or from 5% to 10%, or from 10% to 50%, or from 10% to 40%, or from 10% to 30%, or from 10% to 20%, or from 10% to 15% by weight of the dry bio-crude. The dry bio-crude can be further processed to meet a desired protein content.

In some embodiments, the dry bio-crude includes a fiber content lower than 50%, or lower than 40%, or lower than 30%, or lower than 20%, or lower than 15%, or lower than 10% by weight of the dry bio-crude. In some embodiments, the dry bio-crude includes a fiber content from 1% to 10%, or from 10% to 20%, or from 20% to 30%, or from 30% to 40%, or from 40% to 50% by weight of the dry bio-crude. In some embodiments, the dry bio-crude includes a fiber content from 1% to 50%, or from 5% to 40%, or from 5% to 30%, or from 5% to 20%, or from 5% to 15%, or from 5% to 10%, or from 10% to 50%, or from 10% to 40%, or from 10% to 30%, or from 10% to 20%, or from 10% to 15% by weight of the dry bio-crude. The dry bio-crude can be further processed to meet a desired fiber content.

In some embodiments, the dry bio-crude includes an ash content lower than 50%, or lower than 40%, or lower than 30%, or lower than 25%, or lower than 20%, or lower than 15%, or lower than 10%, or lower than 5% by weight of the dry bio-crude. In some embodiments, the dry bio-crude includes an ash content from 1% to 10%, or from 10% to 20%, or from 20% to 30%, or from 30% to 40%, or from 40% to 50% by weight of the dry bio-crude. In some embodiments, the dry bio-crude includes an ash content from 1% to 50%, or from 2% to 40%, or from 3% to 30%, or from 3% to 20%, or from 3% to 15%, or from 3% to 10%, or from 5% to 10%, or from 5% to 15%, or from 5% to 20% by weight of the dry bio-crude. The dry bio-crude can be further processed to meet a desired ash content.

In some embodiments, the dry bio-crude includes a fat content lower than 50%, or lower than 40%, or lower than 30%, or lower than 25%, or lower than 20%, or lower than 15%, or lower than 10%, or lower than 5% by weight of the dry bio-crude. In some embodiments, the dry bio-crude includes a fat content from 1% to 10%, or from 10% to 20%, or from 20% to 30%, or from 30% to 40%, or from 40% to 50% by weight of the dry bio-crude. In some embodiments, the dry bio-crude includes a fat content from 1% to 50%, or from 1% to 40%, or from 1% to 30%, or from 1% to 20%, or from 1% to 15%, or from 1% to 10%, or from 1% to 5%, or from 2% to 40%, or from 2% to 30%, or from 2% to 20%, or from 2% to 15%, or from 2% to 10%, or from 2% to 5%, or from 3% to 30%, or from 3% to 20%, or from 3% to 15%, or from 3% to 10%, or from 3% to 5%, or from 5% to 10%, or from 5% to 15%, or from 5% to 20% by weight of the dry bio-crude. The dry bio-crude can be further processed to meet a desired fat content.

In some embodiments, the dry bio-crude includes a carbohydrate content higher than 30%, or higher than 40%, or higher than 50%, or higher than 60%, or higher than 65%, or higher than 70%, or higher than 75%, or higher than 80%, or higher than 85% by weight of the dry bio-crude. In some embodiments, the dry bio-crude includes a carbohydrate content from 30% to 90%, or from 40% to 90%, or from 50% to 90%, or from 60% to 90%, or from 70% to 90%, or from 80% to 90%, or from 30% to 85%, or from 40% to 85%, or from 50% to 85%, or from 60% to 85%, or from 70% to 85%, or from 30% to 80%, or from 40% to 80%, or from 50% to 80%, or from 60% to 80%, or from 70% to 80% by weight of the dry bio-crude. The dry bio-crude can be further processed to meet a desired carbohydrate content.

In some embodiments, the dry bio-crude includes negligible amount of volatile matter. In some embodiments, the dry bio-crude includes volatile matter lower than 1%, or lower than 2%, or lower than 5%, or lower than 10%, or lower than 15%, or lower than 20% by weight of the dry bio-crude. In some embodiments, the dry bio-crude includes volatile matter from 1% to 5%, or from 1% to 10%, or from 1% to 15%, or from 1% to 20%, from 2% to 10%, or from 2% to 15%, or from 2% to 20%, from 5% to 10%, or from 5% to 15%, or from 5% to 20% by weight of the dry bio-crude.

In some embodiments, the dry bio-crude includes an energy content higher than 3 MJ/kg, or higher than 5 MJ/kg, or higher than 8 MJ/kg, or higher than 10 MJ/kg, or higher than 12 MJ/kg, or higher than 15 MJ/kg, or higher than 18 MJ/kg, or higher than 20 MJ/kg. The dry bio-crude can be further processed to meet a desired energy content.

Merely by way of example, the dry bio-crude produced by the process described herein include the following contents summarized in Table 3.

TABLE 3

Exemplary Contents of Dry Bio-Crude Product

| | Product A | Product B | Product C |
| --- | --- | --- | --- |
| % Solids | ≥90 | ≥88-92 | ≥95 |
| % Moisture | ≤10 | ≤12-10 | ≤5 |
| % Protein | ≤20 | from 10 to 20 | ≤15-20 |
| % Fat | ≤20 | from 5 to 20 | ≤5-10 |
| % Ash | ≤15 | from 1 to 15 | ≤5-10 |
| % Carbohydrate | ≥50 | from 60 to 90 | ≥65-70 |
| % Fiber | ≤50 | ≤40 | ≤30-35 |

TABLE 3-continued

Exemplary Contents of Dry Bio-Crude Product

|  | Product A | Product B | Product C |
| --- | --- | --- | --- |
| Energy (MJ/kg) | ≥10 | ≥10 | ≥15 |
| % Other | 10% | 5-20% | 10-15% |

Dependent on the morphology of the dryer used in the bio-crude drying procedure and/or the end-user specifications for the product, pelletization can be optionally implemented. Each dryer can produce a slightly different product and can be evaluated to determine the optimum dryer for product characteristics. These characteristics can also be weighed against the end-user specifications whether the final product need to be pelletized or not.

Merely way of example, if pelletization is implemented, then the optimally selected dryer is used to dry the wet bio-crude to a certain range of moisture content (or water content) where the dry bio-crude is introduced into small holes in a die (or whatever shape a customer or end-user desires) and is compressed via rollers.

In some embodiments, the dry bio-crude that exits the dryer and/or pelletization machine is packed and/or sealed in either an industry-standard bag or drum of varying sizes. A sealing method of industry-standard can be used to ensure proper shelf-life and shipping conditions. The bag or drum can include printed instructions or specifications regarding, for example, its intended use, shelf-life, suggested storage conditions, shipping conditions, compositions, or the like, or a combination thereof.

In some embodiments, the dry bio-crude is used as fuel feedstock. The dry bio-crude can be used as feedstock for refinery or coker. The dry bio-crude can be used for feedstock for combustion. The dry bio-crude can also be used for feedstock for fermentation.

In some embodiments, a meal (animal meal or fish meal), e.g., lemna meal if lemna is used as raw feedstock, is obtained from wet bio-crude through procedures similar to those to produce dry bio-crude. The differences in the final processing procedures for the meal (which can be fed to cattle, swine, fish, etc.) are based on specific combinations of dryers and/or pelletization apparatus. This combination is to ensure the characteristics or specific product features needed for desirable feeding purpose including, for example, moisture content (water content), shelf-life, storage, pellet size, particle size, texture, and the like, or a combination thereof. The need for low moisture content (or water content) and/or specific pelletization can be achieved via the apparatus options described above (or a combination thereof) with respect to producing the dry bio-crude.

In some embodiments, the wet bio-crude is subjected to the drying procedure to reduce the moisture content (or water content) to generate a meal. The moisture content (or water content) of the meal is below 40%, or below 30%, or below 20%, or below 10%, or below 5% by weight of the meal. The solids content of the meal is at least 60%, or at least 70%, or at least 80%, or at least 90%, or at least 95% by weight of the meal.

In some embodiments, the meal includes a protein content lower than 50%, or lower than 40%, or lower than 30%, or lower than 25%, or lower than 20%, or lower than 15%, or lower than 10%, or lower than 5% by weight of the meal on a dry weight basis. In some embodiments, the meal includes a protein content from 1% to 10%, or from 10% to 20%, or from 20% to 30%, or from 30% to 40%, or from 40% to 50% by weight of the meal. In some embodiments, the meal includes a protein content from 1% to 50%, or from 5% to 40%, or from 5% to 30%, or from 5% to 20%, or from 5% to 15%, or from 5% to 10%, or from 10% to 50%, or from 10% to 40%, or from 10% to 30%, or from 10% to 20%, or from 10% to 15% by weight of the meal. The meal can be further processed to meet a desired protein content.

In some embodiments, the meal includes a fiber content lower than 50%, or lower than 40%, or lower than 30%, or lower than 20%, or lower than 15%, or lower than 10% by weight of the meal. In some embodiments, the meal includes a fiber content from 1% to 10%, or from 10% to 20%, or from 20% to 30%, or from 30% to 40%, or from 40% to 50% by weight of the meal on a dry weight basis. In some embodiments, the meal includes a fiber content from 1% to 50%, or from 5% to 40%, or from 5% to 30%, or from 5% to 20%, or from 5% to 15%, or from 5% to 10%, or from 10% to 50%, or from 10% to 40%, or from 10% to 30%, or from 10% to 20%, or from 10% to 15% by weight of the meal. The meal can be further processed to meet a desired fiber content.

In some embodiments, the meal includes an ash content lower than 50%, or lower than 40%, or lower than 30%, or lower than 25%, or lower than 20%, or lower than 15%, or lower than 10%, or lower than 5% by weight of the meal on a dry weight basis. In some embodiments, the meal includes an ash content from 1% to 10%, or from 10% to 20%, or from 20% to 30%, or from 30% to 40%, or from 40% to 50% by weight of the meal. In some embodiments, the meal includes an ash content from 1% to 50%, or from 2% to 40%, or from 3% to 30%, or from 3% to 20%, or from 3% to 15%, or from 3% to 10%, or from 5% to 10%, or from 5% to 15%, or from 5% to 20% by weight of the meal. The meal can be further processed to meet a desired ash content.

In some embodiments, the meal includes a fat content lower than 50%, or lower than 40%, or lower than 30%, or lower than 25%, or lower than 20%, or lower than 15%, or lower than 10%, or lower than 5% by weight of the meal on a dry weight basis. In some embodiments, the meal includes a fat content from 1% to 10%, or from 10% to 20%, or from 20% to 30%, or from 30% to 40%, or from 40% to 50% by weight of the meal. In some embodiments, the meal includes a fat content from 1% to 50%, or from 1% to 40%, or from 1% to 30%, or from 1% to 20%, or from 1% to 15%, or from 1% to 10%, or from 1% to 5%, or from 2% to 40%, or from 2% to 30%, or from 2% to 20%, or from 2% to 15%, or from 2% to 10%, or from 2% to 5%, or from 3% to 30%, or from 3% to 20%, or from 3% to 15%, or from 3% to 10%, or from 3% to 5%, or from 5% to 10%, or from 5% to 15%, or from 5% to 20% by weight of the meal. The meal can be further processed to meet a desired fat content.

In some embodiments, the meal includes a carbohydrate content higher than 30%, or higher than 40%, or higher than 50%, or higher than 60%, or higher than 65%, or higher than 70%, or higher than 75%, or higher than 80%, or higher than 85% by weight of the meal. In some embodiments, the meal includes a carbohydrate content from 30% to 90%, or from 40% to 90%, or from 50% to 90%, or from 60% to 90%, or from 70% to 90%, or from 80% to 90%, or from 30% to 85%, or from 40% to 85%, or from 50% to 85%, or from 60% to 85%, or from 70% to 85%, or from 30% to 80%, or from 40% to 80%, or from 50% to 80%, or from 60% to 80%, or from 70% to 80% by weight of the meal. The meal can be further processed to meet a desired carbohydrate content.

In some embodiments, other characteristics of the meal, e.g., the particle size, texture, bacterial specification, or the like, or a combination thereof, are suitable for the intended purpose. In some embodiments, standard plate count of bacteria is lower than 100,000/g, or lower than 80,000/g, or lower than 60,000/g, or lower than 50,000/g, or lower than 40,000/g, or lower than 30,000/g, or lower than 25,000/g, or lower than 20,000/g, or lower than 15,000/g. In some embodiments, the meal does not include detectible level of *E. coli*. In some embodiments, the meal does not include detectible level of *salmonella*. In some embodiments, the meal includes yeast/mold of lower than 500/g, or lower than 400/g, or lower than 300/g, or lower than 250/g, or lower than 200/g, or lower than 150/g, or lower than 100/g, or lower than 50/g.

In some embodiments, the process recovers multiple products from industrial-scale production of a raw feedstock of a biomass of an aquatic species. The multiple products include a dry protein concentrate and at least one selected from a dry bio-crude and meal. The yield of each products can be evaluated based on the dry mass of the raw feedstock. As used herein, "dry mass" refers to the weight of the raw feedstock after it is dried in, for example, a drying apparatus. Such a drying apparatus can be, for example, an vacuum oven, or the like.

In some embodiments, the yield of the dry protein concentrate is at least 5%, or at least 10%, or at least 15%, or at least 20%, or at least 25%, or at least 30% of the dry mass of the raw feedstock. In some embodiments, the yield of the dry protein concentrate is from 5%-50%, or from 5%-40%, or from 5%-30%, or from 5%-25%, or from 5%-20%, or from 10%-50%, or from 10%-40%, or from 10%-30%, or from 10%-25%, or from 10%-20%, or from 15%-50%, or from 15%-40%, or from 15%-30%, or from 15%-25%, or from 15%-20%, or from 20%-50%, or from 20%-40%, or from 20%-30%, or from 20%-25% of the dry mass of the raw feedstock.

In some embodiments, the yield of the dry bio-crude is at least 10%, or at least 15%, or at least 20%, or at least 25%, or at least 30%, or at least 40% of the dry mass of the raw feedstock. In some embodiments, the yield of the dry bio-crude is from 5%-60%, or 5%-50%, or from 5%-40%, or from 5%-30%, or from 5%-25%, or from 5%-20%, or from 10%-60%, or from 10%-50%, or from 10%-40%, or from 10%-30%, or from 10%-25%, or from 10%-20%, or from 15%-60%, or from 15%-50%, or from 15%-40%, or from 15%-30%, or from 15%-25%, or from 15%-20%, or from 20%-60%, or from 20%-50%, or from 20%-40%, or from 20%-30%, or from 20%-25% of the dry mass of the raw feedstock.

In some embodiments, the yield of the meal is at least 10%, or at least 15%, or at least 20%, or at least 25%, or at least 30%, or at least 40% of the dry mass of the raw feedstock. In some embodiments, the yield of the meal is from 5%-60%, or 5%-50%, or from 5%-40%, or from 5%-30%, or from 5%-25%, or from 5%-20%, or from 10%-60%, or from 10%-50%, or from 10%-40%, or from 10%-30%, or from 10%-25%, or from 10%-20%, or from 15%-60%, or from 15%-50%, or from 15%-40%, or from 15%-30%, or from 15%-25%, or from 15%-20%, or from 20%-60%, or from 20%-50%, or from 20%-40%, or from 20%-30%, or from 20%-25% of the dry mass of the raw feedstock.

In some embodiments, for the total amount of protein in the multiple products, at least 30%, or at least 35%, or at least 40%, or at least 45%, or at least 50%, or at least 55%, or at least 60%, or at least 65%, or at least 70%, or at least 75%, or at least 80%, or at least 85% is in the dry protein concentrate. In some embodiments, for the total amount of protein in the multiple products, less than 70%, or less than 65%, or less than 60%, or less than 55%, or less than 50%, or less than 45%, or less than 40%, or less than 35%, or less than 30%, or less than 25%, or less than 20%, or less than 15% is in the dry bio-crude and/or meal.

Any one liquid phase (e.g., juice, filtered juice, clarified or polished juice) or solid phase (e.g., a first solid phase, second solid phase, third solid phase, wet bio-crude) generated in one procedure can be store in the storage tank before it is fed to one or more downstream procedures or apparatuses. It can help to generate a homogeneous liquid phase or solid phase for the downstream procedure(s) or apparatus(es). This can accommodate different operation schedules or modes including, for example, continuous mode, batch mode, or multiple feeding streams to one or more downstream procedure(s) and/or apparatus(es). The liquid phase in the storage tank can be maintained at a desirable temperature to reduce degradation and maintain high quality until further processing. Merely by way of example, the wet protein concentrate (or washed wet protein concentrate is stored in a chilled storage tank until further processing. The chilled storage tank can be maintained at a temperature below room temperature. In particular embodiments, the chilled storage tank is maintained at a temperature below 50° C., or below 40° C., or below 30° C., or below 25° C., or below 20° C., or below 15° C., or below 10° C., or below 5° C., or below 0° C., or below −5° C., or below −10° C.

The efficiency of the process of isolating protein from the biomass comprising an aquatic species can be further improved by any one or a combination of the following procedures.

In certain exemplary embodiments, the biomass comprising the aquatic species can be processed to extract lipid content using a solvent and or water, e.g. hexane, ethanol, or the like, or a combination thereof, as a pre-treatment before the process of isolating protein or post-treatment. In other exemplary embodiments, the biomass including the aquatic species can be processed to remove components of the biomass that can such as lipids. This procedure can be applied to the wet biomass immediately before drying, or it can be used with the juice resulting from the separating of it from the raw feedstock biomass (or dewatered biomass). The procedure can be performed by adding a solvent or water to the material, followed by the addition of an acid (hydrochloric, nitric, or other). The material is then mixed, in certain embodiments under conditions of elevated temperature or pressure. In other embodiments, the mixing is carried out at room temperature and atmospheric pressure. The mixture is then introduced to a decanting apparatus. In this apparatus, the mixture is spun at high speed, and the liquid therein is forced through holes to separate the solid mass from the liquid.

In certain exemplary embodiments, the pH value of any one or more of the following: the feedstock comprising the lysed biomass, the juice generated by the separating procedure, the filtered juice generated by the filtering procedure, or the clarified juice generated by the clarifying procedure, can be changed. In specific exemplary embodiments, the pH value of the feedstock comprising the lysed biomass can be increased to above 7.0, or above 7.5, or above 8.0, or above 8.5, or above 9.0, or above 9.5, or above 10.0. The pH of the feedstock can be increased by, for example, the addition of NaOH or other agents known to those of skill in the art. Similarly, the pH value of the filtered juice can be increased. The change in the pH value can be maintained throughout the rest of the process of protein isolation. The change in the pH value can be neutralized after the procedure in which the changed pH value is desirable.

The residence time during any part of the process of isolating protein can be optimized to increase the efficiency of the process. In certain exemplary embodiments, the residence time can be chosen to increase the recovery of soluble proteins in unclarified juice after passage through a filter press.

In further exemplary embodiments procedures employed to improve the efficiency of the process include diluting the lysed biomass with water to increase the recovery of soluble protein content in unclarified juice after passage through a filter press, sonicating the lysed biomass to increase recovery of soluble protein content in un-clarified juice after passage through a filter press, subjecting the lysed biomass to carbohydrase enzymes individually or in combination, subjecting any of the solid phases generated in the processes described above to protease enzymes individually or in combination to reduce protein and/or ash content and to increase carbohydrate content, performing chromatographic processes, and solubilizing non-water soluble protein (by, for example, pH manipulation) in any of the solid phases generated in the protein recovery processes described above.

Embodiments of the invention also provide systems of recovering multiple products from biomass of an aquatic species; such systems can include, for example: a lysing unit for lysing the biomass to generate a lysed biomass; a separating unit for separating the lysed biomass to generate a juice and a solid phase; a unit for forming a wet protein concentrate using the juice; a protein drying unit for drying the wet protein concentrate to generate a dry protein concentrate; and a unit for drying a wet bio-crude to generate at least one product selected from a dry bio-crude and carbohydrate-rich meal, wherein the wet bio-crude can include the solid phase; and wherein the multiple products can include products selected from, for example, the dry protein concentrate, dry bio-crude, carbohydrate-rich meal, and the like, and wherein at least about 50% of the protein in the multiple products is in the dry protein concentration.

Summarized in Table 4 are exemplary apparatuses that can be included in the units described above.

TABLE 4

Exemplary apparatuses

| | Option |
|---|---|
| Lysing unit | Colloid mill, Knife mill, Ball mill, Hammer mill, Grinding mill, Puree machine, Filter press |
| Separating unit | Belt press, Decanter centrifuge, Fan press, Rotary press, Screw press, Filter press, Finisher press |
| Unit for forming wet protein concentrate | Vibratory separator, Vibrating screen filter, Circular vibratory separator, Linear/inclined motion shaker, Decanter centrifuge, Filter press, High-speed disc stack centrifuge, Microfiltration, Ultra-filtration, Heat precipitator, Acid precipitation, Settling tank, Clarifier |
| Protein drying unit | Spray dryer, Drum dryer, Flash dryer |

It is understood that exemplary apparatuses for each unit are listed for illustration purposes only, and this is not intended to limit the scope of the application. A specific combination of these or other apparatuses or units can be configured in such a system for the intended use based on the teachings in the application.

EXAMPLES

The following non-limiting examples are provided to further illustrate embodiments of the present application. It should be appreciated by those of skill in the art that the techniques disclosed in the examples that follow represent approaches discovered by the inventors to function well in the practice of the application, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the application.

Example 1

Exemplary Method of Processing Lemnae

An exemplary method of processing lemnae is described herein. The process was tested by experiments.

During harvest, an automated skimmer system withdrew equal amounts of a micro-crop, e.g., lemnae, from designated areas in a growth system including ponds (bioreactors), and a biomass-containing slurry (also referred to as a raw feedstock) was transferred via a pumping system onto an inclined vibrating screen. The biomass slurry was collected by the screen and conveyed to a knife-style hammer mill where the wet biomass fronds were lysed to expose the internal water and protein. The protein-laden juice from these fronds was then extracted by compression in a belt press and a screw press in series. The wet bio-crude ejected from the screw press was collected for drying in a spin flash dryer, while the juice was filtered using a vibratory separator. The filtered juice included fine particulate solids which were removed by centrifugation. The protein in the centrifuged juice was then coagulated by reducing the pH value of the centrifuged juice, or heat-coagulated using a heat exchanger, to generate a broth comprising a wet protein concentrate. The wet protein concentrate was then separated using a high-speed multi-disk stack centrifuge. The supernatant liquid was discarded, while the wet protein concentrate was dried using a spray dryer. The dried product was packaged.

Although not carried out in this example, the lemnae biomass can be further treated to reduce the amount of ash, lipids, or other undesirable components in the final product.

After washing, the lemnae were homogenized, mixed, juiced, clarified by centrifugation, filtered, and the solution was exposed to a low pH to precipitate the proteins and generate a broth comprising a wet protein concentrate. The broth was centrifuged to generate a pellet comprising the wet protein concentrate. The pellet was serially washed and clarified by centrifugation, and then dried to generate the dry protein concentrate.

The dry protein concentrate generated in this manner included 50% to 80% protein by weight.

The biomass slurry harvested from a growth system was pumped to the process building where it was dewatered and pressed through a number of stages to extract its internal juice. Large solid particles (first solid phase) were then filtered out of the juice using a vibratory separator (vibrating screen filter).

a. Preparation i. Inclined Vibrating Screen

The biomass slurry was hydraulically conveyed to a process building by pumping the biomass with a large portion of water into the process building. The biomass was separated from the water by an inclined vibrating screen. The water flowed through the screen and was pumped back into the ponds (bioreactors), while the biomass was conveyed down the screen by low amplitude vibration. The screen deposited the wet biomass into the hopper of an inclined auger. This feed auger used an Archimedes' screw to feed the fresh biomass into the hopper of a knife-style hammer mill (knife mill) at a constant rate. An added benefit of using the feed auger was that it allowed excess water to drain off of the wet biomass as a result of the inclination of the auger.

ii. Knife Mill

The knife mill employed a horizontal rotating shaft on which blades were mounted. The rotor was spun at high speed while the biomass slurry was fed via a small feed hopper built internally. The biomass slurry was lysed and expelled through a screen at the bottom of the mill. This mill sheared the biomass fronds to expose the internal cell structure, allowing more internal water and protein to be removed.

iii. Belt Press

The belt press was the primary pressing stage for the lysed biomass. The lysed biomass was pumped from a hopper between two perforated belt filters. These belts were passed through a series of rollers. As the belts passed through the rollers, internal juice was expelled. The juice comprised water as well as water-soluble compounds, such as soluble protein and minerals. Once through the press, the first solid phase was scraped into the secondary pressing stage.

iv. Screw Press

The screw press was the secondary pressing stage for the first solid phase of the lysed biomass. It used the mechanical compression of a screw to squeeze out at least part of the remaining internal juice from the first solid phase. After passing through the screw press, the pressed solids (also referred to as a wet bio-crude) were collected in large mobile hoppers for drying.

v. Vibratory Separator

The juice flowed from the screw press into a 10 to 200 micron vibrating screen filter. Here, large particles that passed through the screw press were filtered. The solids (mash), also referred to as a second solid phase, were recycled back to the screw press, while the filtered juice was sent for protein purification. The recycling of the second solid phase allowed further juice to be pressed from the second solid phase.

b. Protein Purification

Once filtered through a vibrating screen, the filtered juice was then purified to isolate a concentrated protein. Centrifugation and coagulation were employed in this purification.

i. Centrifuge (Clarification)

The filtered juice was pumped through a high speed multi-disk stack centrifuge to remove smaller particles that were not removed in the vibratory separator. This step also removed a large portion of the carbohydrates as well as fiber. The third solid phase ejected from the centrifuge was added back to the screw press so that protein losses were reduced. The centrifuged juice (also referred to as clarified juice) was then pumped into a chilled storage tank before further processing.

ii. Protein Coagulation

The proteins in the centrifuged juice were coagulated by reducing the pH. The pH was lowered to less than 5 by using either hydrochloric or sulfuric acid. This acid treating process forced at least a part of the protein to coagulate and precipitate, generating a broth comprising a wet protein concentrate.

Alternatively, the centrifuged juice was pumped at a regulated flow rate into a precipitator containing a series of plate heat exchangers. In the heating zone of the precipitator the centrifuged juice was heated to anywhere from 40° C. to 90° C. The centrifuged juice, now considered broth, was then quickly cooled to a temperature between 10° C. and 40° C. This heating and cooling forced the protein to coagulate and precipitate out of the centrifuged juice to generate a broth comprising a wet protein concentrate.

iii. Centrifuge (Protein Separation)

The wet protein concentrate was separated from the remaining portion of the broth. The broth was passed through a high speed multi-disk stack centrifuge for separation of the wet protein concentrate from the supernatant liquid, referred to as "liquor." Inside the centrifuge, the liquor was forced to the top of the centrifuge by centripetal force and was pumped out, while the denser protein wet concentrate was collected at the bottom and was periodically ejected from the centrifuge. The wet protein concentrate was then washed with water to remove impurities and centrifuged again. The wet protein concentrate from this second centrifugation was chilled in storage to reduce degradation and maintain high quality until it was dried.

c. Drying

The wet bio-crude and wet protein concentrate were conveyed to the drying process to reduce their water content to 8-12%. The wet bio-crude was dried using a spin flash dryer, while the protein wet concentrate was dried using a spray dryer. Once dried, the wet protein concentrate is referred to as a dry protein concentrate.

i. Bio-Crude Drying

The wet bio-crude from the screw press was collected in mobile hoppers. The wet bio-crude was then introduced into the spin flash dryer by being dropped into the agitated feed vat of the spin flash dryer. The wet bio-crude was fed from the feed vat to a drying chamber equipped with a spinning mixer. Hot air flowed through the wet bio-crude as the mixer broke up any large clumps. The wet, heavy bio-crude was kept in the drying chamber until the water content (also referred to as moisture content) was low enough for the material to be light enough to be carried into the cyclone separator by the flow of hot air. The dry bio-crude was then collected at the bottom of the cyclone.

ii. Protein Drying

The wet protein concentrate was pumped from chilled storage into a spray dryer. The spray dryer used a high-speed centrifugal atomizer to spray a fine mist into a heated drying chamber. The fine mist created more surface area, thus increasing the drying efficiency. The water evaporated as the small particles fall to the bottom. The dry protein concentrate, also referred to as protein dry meal, was then collected with the use of a cyclone separator and baghouse combination.

iii. Packaging

The dry bio-crude and dry protein concentrate exited the dryers and were packed in a variety of bag sizes and sealed after being analyzed for moisture content.

This is understood that some steps described above are optional, and devices other than those specified in the example can be use to achieved the same or similar functions. Some additional exemplary methods of processing are described elsewhere in the application.

Example 2

Protein Isolation

A process for isolating protein from lemnae is described in this example. The process was tested by experiments.

During harvest, an automated skimmer system periodically withdrew equal amounts of a micro-crop, e.g. lemnae, from designated areas in a growth system comprising ponds (bioreactors), and a biomass-containing slurry (also referred to as a raw feedstock) was transferred via a pumping system onto an inclined vibrating screen. The biomass slurry was collected and conveyed to a knife-style hammer mill where the wet biomass fronds were lysed to expose the internal water and protein. The protein-laden juice from these fronds was then be extracted by compression in a belt press and a screw press in series. The wet bio-crude ejected from the screw press was collected for drying in a spin flash dryer, while the juice was filtered using a vibratory separator. The filtered juice comprised fine particulate solids which were removed by centrifugation. The protein in the centrifuged juice was then heat-coagulated using a heat exchanger to generate a broth comprising a wet protein concentrate. The wet protein concentrate was then separated using a high-speed multi-disk stack centrifuge. The supernatant liquid was discarded, while the wet protein concentrate was dried using a spray dryer. The dried product was packaged.

a. Preparation i. Inclined Vibrating Screen

The biomass slurry was hydraulically conveyed to a process building by pumping the biomass with a large portion of water into the process building. The biomass was separated from the water by an inclined vibrating screen. The water flowed through the screen and was pumped back into the ponds, while the biomass was conveyed down the screen by low-amplitude vibration. The screen dumped the wet biomass into the hopper of an inclined auger. This feed auger employed an Archimedes' screw to feed the fresh biomass into the hopper of a knife-style hammer mill (knife mill) at a constant rate. An added benefit of the feed auger was that it allowed excess water to drain off of the wet biomass due to the inclination of the auger.

ii. Knife Mill

The knife mill employed a horizontal rotating shaft on which blades were mounted. The rotor was spun at high speed while the biomass slurry was fed via a small feed hopper built internally. The biomass slurry was lysed and expelled through a screen at the bottom of the mill. This mill sheared the biomass fronds to expose the internal cell structure, allowing more internal water and protein to be removed.

iii. Belt Press

The belt press was the primary pressing stage for the lysed biomass. The lysed biomass was pumped from a hopper between two perforated belt filters. These belts were passed through a series of rollers. As the belts passed through the rollers, internal juice was expelled. The juice comprised water as well as water-soluble compounds, such as soluble protein and minerals. Once through the press, the first solid phase was scraped into the secondary pressing stage.

iv. Screw Press

The screw press was the secondary pressing stage for the first solid phase of the lysed biomass. It used the mechanical compression of a screw to squeeze out at least part of the remaining internal juice from the first solid phase. After passing through the screw press, the pressed solids (also referred to as a wet bio-crude) were collected in large mobile hoppers for drying.

v. Vibratory Separator

The juice flowed from the screw press into a 10-200 micron vibrating screen filter. Here large particles that passed through the screw press were filtered. The solids (mash), also referred to as a second solid phase, were recycled back to the screw press, while the filtered juice was sent for protein purification. The recycling of the second solid phase allowed further juice to be pressed from the second solid phase.

b. Protein Purification

Once filtered through a vibrating screen, the filtered juice was then purified to isolate a concentrated protein. Centrifugation and coagulation were employed in this purification.

i. Centrifuge (Clarification)

The filtered juice was pumped through a high speed multi-disk stack centrifuge to remove smaller particles that were not removed in the vibratory separator. This step can also remove a large portion of the carbohydrates as well as fiber. The third solid phase ejected from the centrifuge was added back to the screw press so that protein losses were reduced. The centrifuged juice (also referred to as clarified juice) was then pumped into a chilled storage tank before further processing.

ii. Protein Coagulation

The centrifuged juice was pumped at a regulated flow rate into a precipitator containing a series of plate heat exchangers. In the heating zone of the precipitator the centrifuged juice was heated anywhere from 80° C. to 85° C. The centrifuged juice, now considered broth, was then quickly cooled to 10° C. to 40° C. This heating and cooling forced the protein to coagulate and precipitate out of the centrifuged juice to generate a broth comprising a wet protein concentrate.

iii. Centrifuge (Protein Separation)

The wet protein concentrate was separated from the remaining portion of the broth. The broth was run through a high speed multi-disk stack centrifuge for separation of the wet protein concentrate from the supernatant liquid referred to as liquor. Inside the centrifuge, the liquor was forced to the top of the centrifuge by centripetal force and was pumped out, while the denser protein wet concentrate was collected at the bottom and was periodically ejected from the centrifuge. The wet protein concentrate was then washed with water to remove impurities and centrifuged again. The wet protein concentrate from this second centrifugation was chilled in storage to reduce degradation and maintain high quality until it was dried.

c. Drying

The wet bio-crude and wet protein concentrate were conveyed to the drying process to reduce their water content to 8-12%. The wet bio-crude was dried using a spin flash dryer, while the protein wet concentrate was dried using a spray dryer. Once dried, the wet protein concentrate is referred to as a dry protein concentrate.

i. Bio-Crude Drying

The wet bio-crude from the screw press was collected in mobile hoppers. The wet bio-crude was then introduced into the spin flash dryer by being dropped into the agitated feed vat of the dryer. The wet bio-crude was fed to a drying chamber equipped with a spinning mixer. Hot air flowed through the wet bio-crude as the mixers broke up any large clumps. The wet, heavy bio-crude was kept in the drying chamber until the water content (also referred to as moisture content) was low enough for the material to be light enough to be carried into the cyclone separator by the flow of hot air. The dry bio-crude was then collected at the bottom of the cyclone.

ii. Protein Drying

The wet protein concentrate was pumped from chilled storage into a spray dryer. The spray dryer used a high-speed centrifugal atomizer to spray a fine mist into a heated drying chamber. The fine mist created more surface area, therefore increasing the drying efficiency. The water evaporated as the small particles fall to the bottom. The dry protein concentrate, also referred to as protein dry meal, was then collected with the use of a cyclone separator and baghouse combination.

iii. Packaging

The dry bio-crude and dry protein concentrate exited the dryers and was packed in a variety of bag sizes and sealed after being analyzed for moisture content.

Example 3

Flow Diagram of Exemplary Process of Protein Isolation

Figure 2:
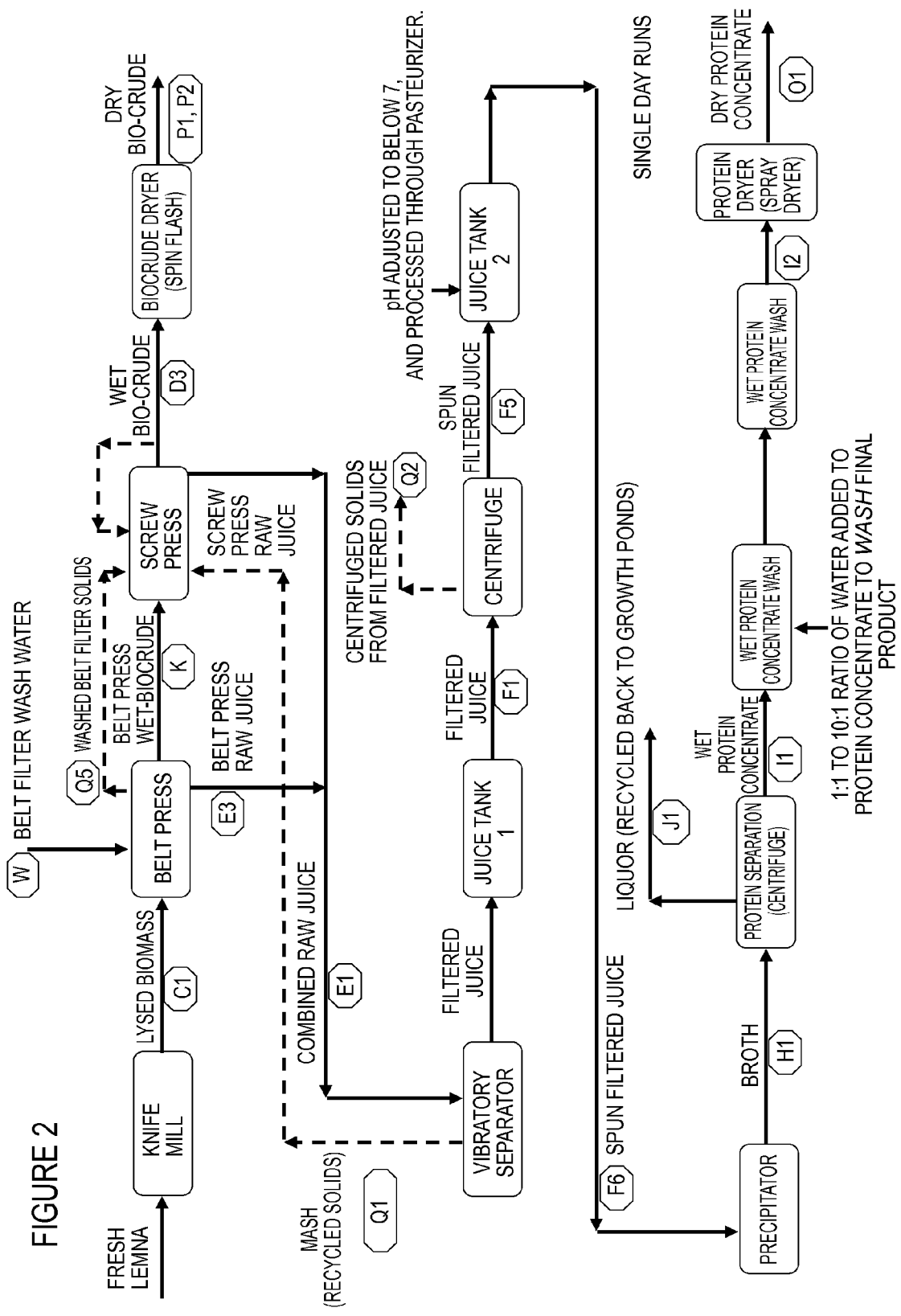
FIG. 2 is a flow diagram illustrating an exemplary process of isolating protein from fresh lemna.

FIG. 2 shows a flow diagram of an exemplary process of isolating protein from an aquatic species, e.g., fresh lemna.

Fresh lemna (also referred to as biomass slurry or raw feedstock) are conveyed to a knife mill where the wet biomass fronds are lysed to expose the internal water and protein. The lysed biomass is conveyed to a belt press in which the lysed biomass is pressed to generate a first solid phase (identified in the Figure as "Belt Press Wet Bio-Crude") and a juice (identified in the Figure as "Belt Press Raw Juice"). The first solid phase is conveyed to a screw press for further pressing to generate a second juice (identified in the Figure as "Screw Pres Raw Juice") and a wet bio-crude. The first solid phase remaining in the belt press is flushed using water (identified in the Figure as "Belt Filter Wash Water"). The washed belt filter solids obtained thereby are fed to the screw press for further pressing. The wet bio-crude ejected from the screw press is collected for drying using a biocrude dryer (a spin flash dryer) to generate a dry bio-crude. The belt press raw juice and the screw press raw juice are combined to form a combined raw juice and fed to a vibratory separator in which the combined raw juice is filtered to generate a mash comprising recycled solids) and filtered juice. The mash is fed to a screw press for further pressing. The filtered juice is stored in juice tank 1. Juice Tank 1 is a chilled storage tank. Filtered juice from juice tank 1 is clarified using a centrifuge to generate centrifuged solids from the filtered juice and a spun filtered juice (also referred to as a "clarified juice"). The centrifuged solids from the filtered juice are fed to a screw press for further pressing. The centrifuged solids from the filtered juice are used as a wet bio-crude. The spun filtered juice is stored in juice tank 2, and the pH thereof is adjusted to below 7.0. The spun filtered juice is then processed in a precipitator to cause heat-induced protein coagulation, generating a broth comprising a wet protein concentrate. In other embodiments, the protein in the spun filtered juice is coagulated by acid treatment, a combination of acid and thermal treatment. In order to separate the protein from the remaining part of the broth, the broth is centrifuged to generate a liquor and a wet protein concentrate. The liquor is recycled back to the growth ponds (also referred to as bioreactors). In other embodiments, the liquor is discarded. The wet protein concentrate is washed or diluted by adding water to the wet protein concentrate to form a wet protein concentrate wash. The ratio of wet protein concentrate to water is 1:1 to 1:10 by weight. The resulting wet protein concentrate wash is dried using a protein dryer (spray dryer) to generate a dry protein concentrate. The dry protein concentrate is packaged for further use or analysis.

In FIG. 2, each dotted line indicates a recycled mass stream, while each letter or letter/number combination within a hexagon indicates a sampling location or a material ID.

Example 4

Dry Protein Concentrate Yield and Wet Bio-Crude Yield

Fresh lemna was processed following the process shown in FIG. 2 and described in Example 2 over a period of approximately one month.

Figure 3:
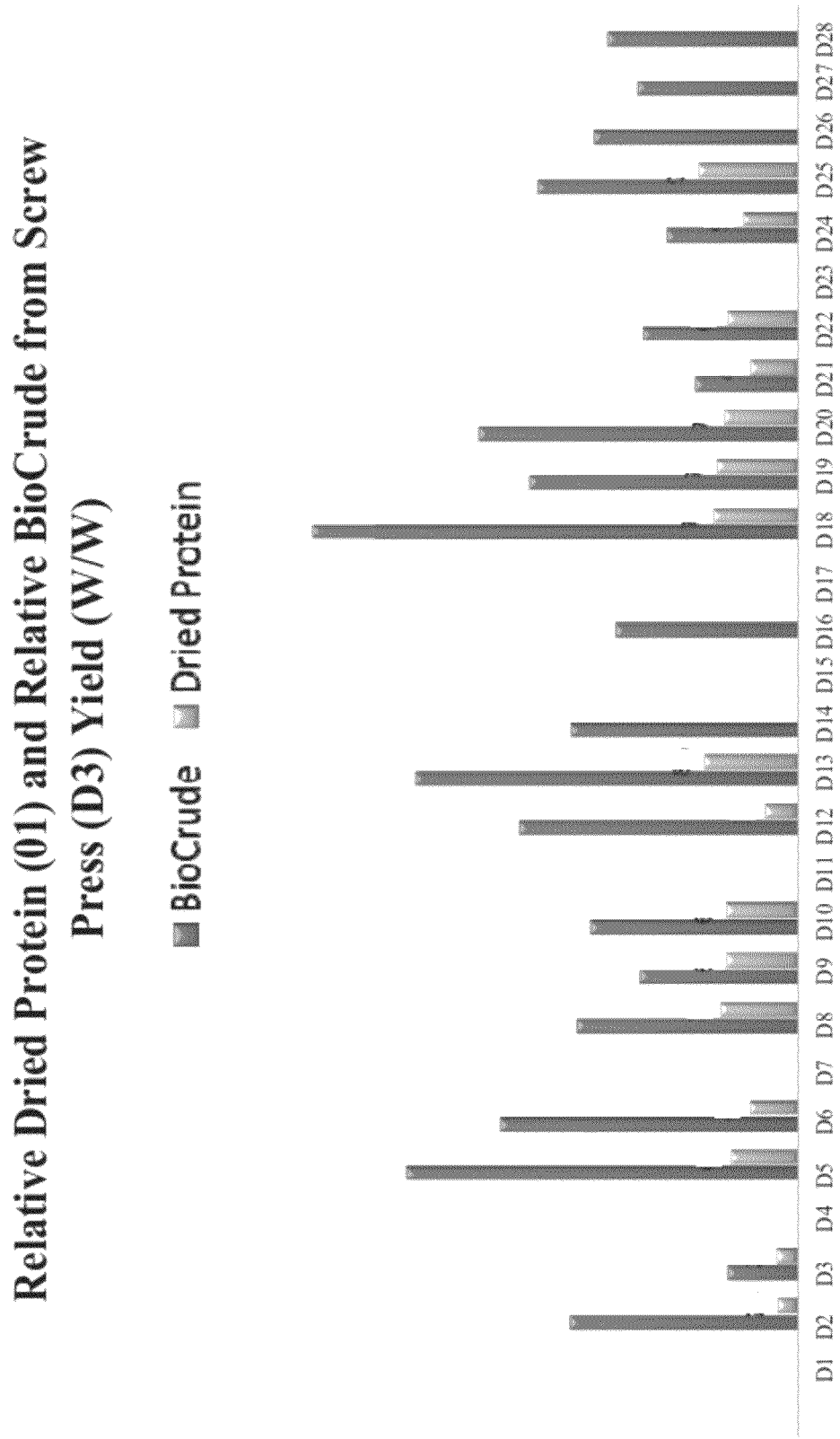
FIG. 3 is a bar graph showing the relative yield of dried protein (dry protein concentrate) and the relative yield of bio-crude from a screw press.

FIG. 3 shows the yield of wet bio-crude (labeled "BioCrude") sampled at D3 of FIG. 2, and the yield of dry protein concentrate (labeled "Dried Protein") sampled at O1 of FIG. 2. As used herein and described elsewhere in the application, axis labels, such as D1, D2, D3, and so on, indicate lot numbers of the samples analyzed.

The results are expressed as the ratio of the mass of bio-crude or dry protein concentrate to that of the fresh lemna processed to obtain these products. The horizontal axis indicates the lot IDs. For each pair of columns for the same lot ID, the left column is the result for the bio-crude, while the right column is that for the dried protein.

Relative data are shown in FIG. 3. This graph illustrates that a significantly higher portion of solids remains in the biocrude stream compared to the protein stream.

Example 5

Wet and Dry Protein Concentrate Yield

Figure 4:
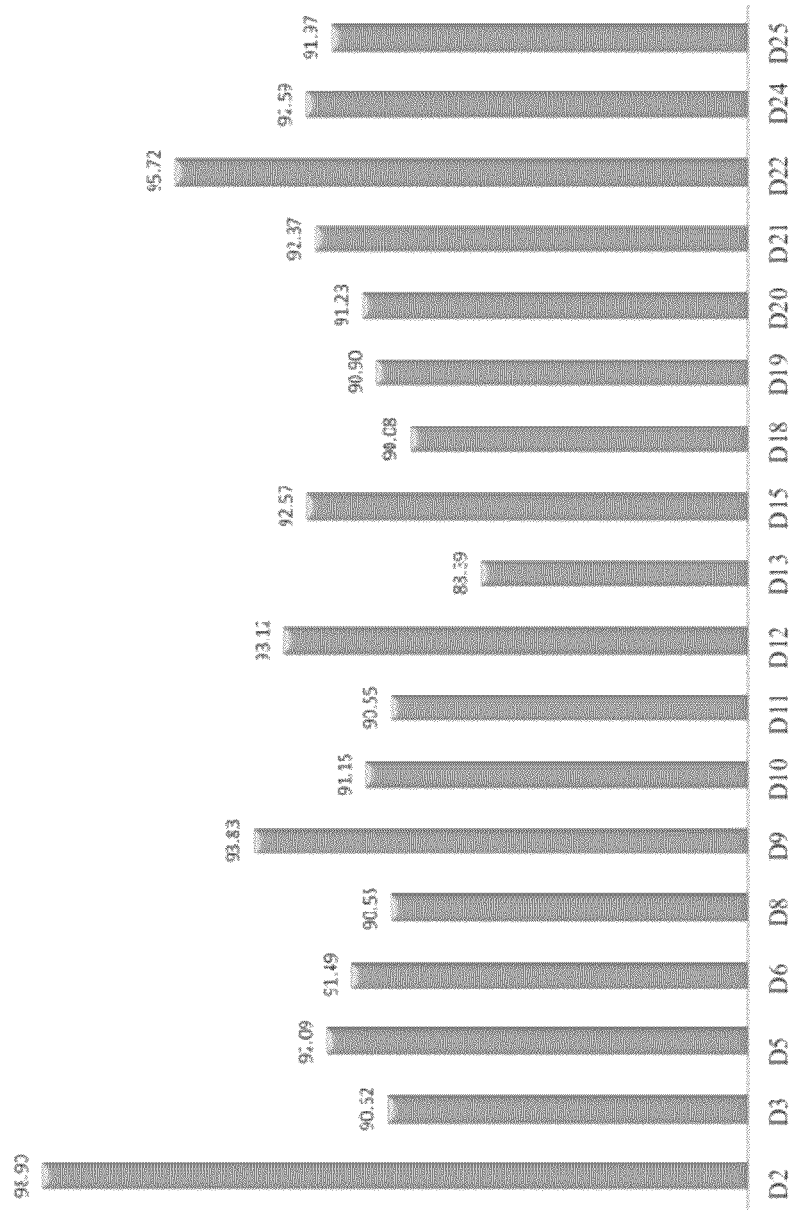
FIG. 4 is a bar graph showing an example of moisture content of wet protein concentrate generated in a process as shown in FIG. 2.

FIG. 4 shows the moisture content (water content) of the wet protein concentrate at point I1 in the process shown in FIG. 2 and carried out in Example 4. The results are expressed as a percentage ratio of the mass of the water to that of the wet protein concentrate. The horizontal axis indicates the Lot ID numbers.

Figure 5:
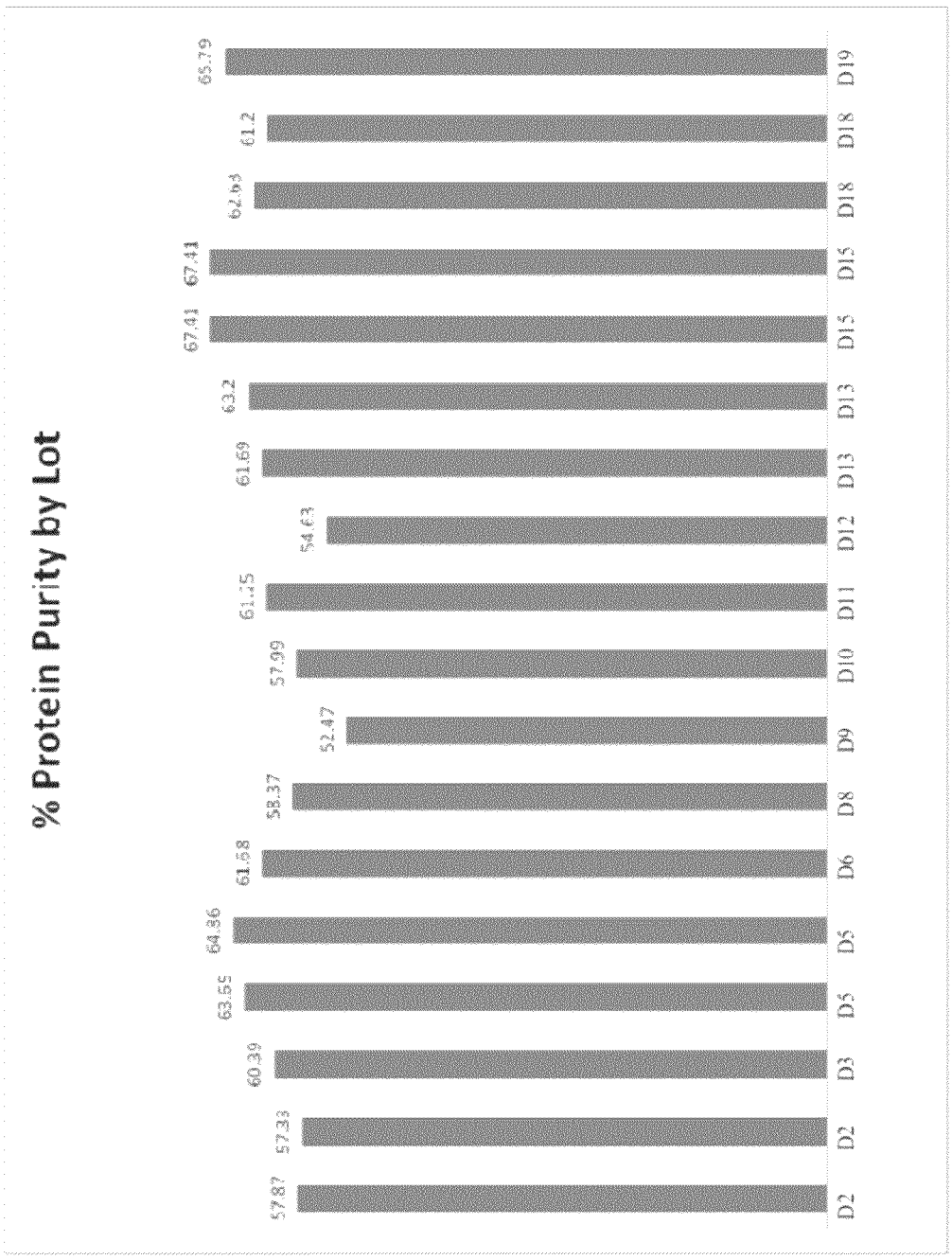
FIG. 5 is a bar graph showing protein purity by lot generated in the process shown in FIG. 2.

FIG. 5 shows the protein purity by lot generated in the same process. The results are expressed as a percentage ratio of the mass of protein to that of the dry protein concentrate. The horizontal axis indicates the Lot ID numbers.

FIG. 5 shows that the protein purity of the generated dry protein concentrate showed the range of 52-67% for this time period.

Example 6

Wet and Dry Bio-Crude Yield

Figure 6:
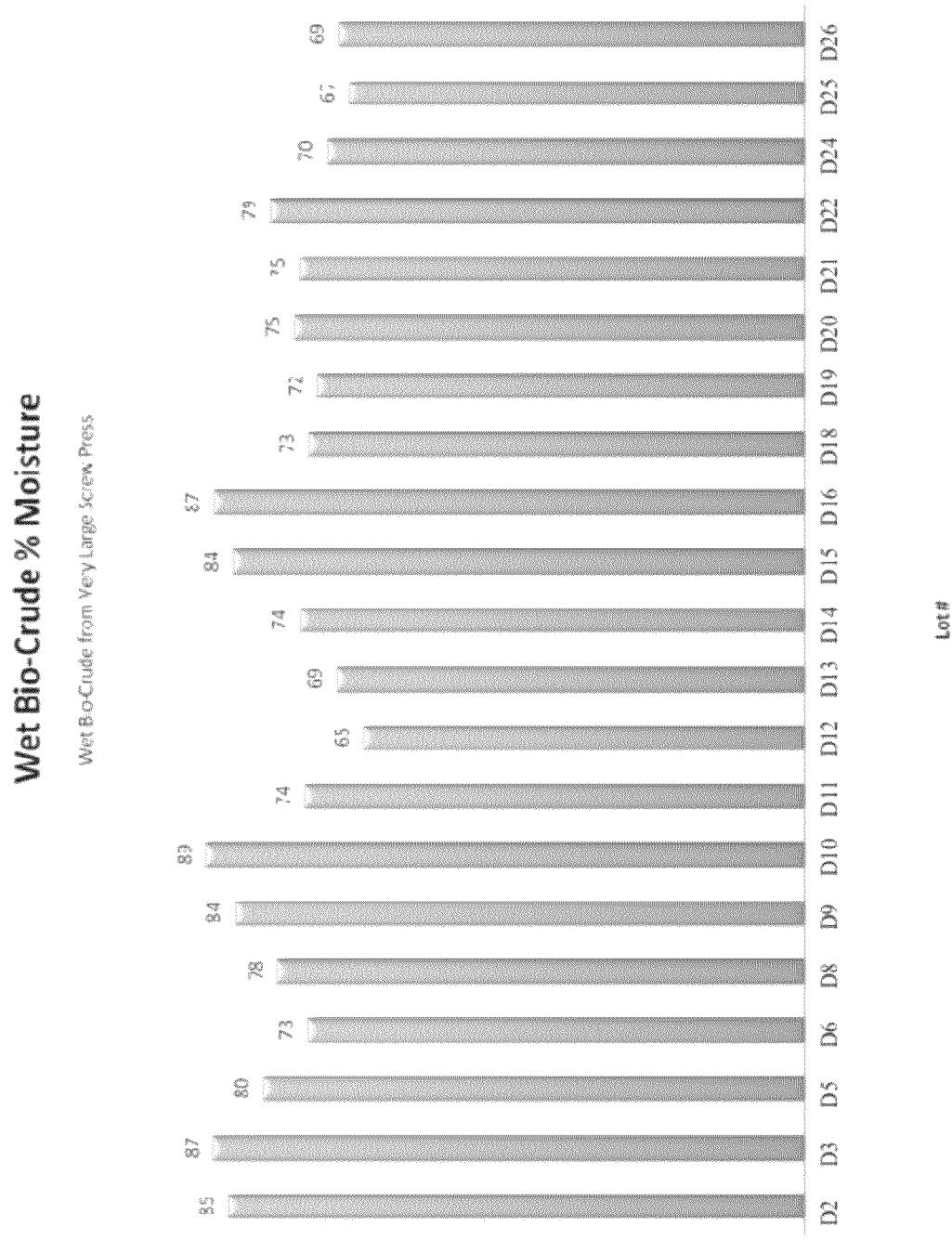
FIG. 6 is a bar graph showing moisture content of wet bio-crude generated in the process shown in FIG. 2.

FIG. 6 shows the moisture content (water content) of the wet bio-crude obtained from the screw press and sampled at point D3 in FIG. 2. The results are expressed as a percentage ratio of the mass of water to the total mass of the wet bio-crude. The horizontal axis indicates the Lot ID numbers.

Figure 7:
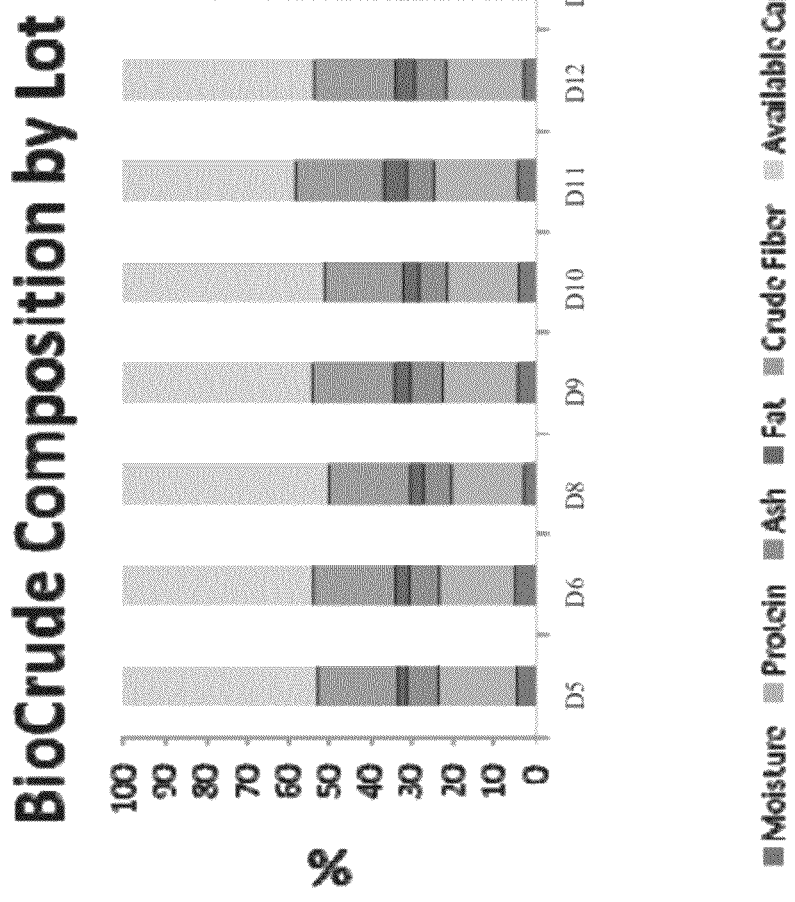
FIG. 7 is a bar graph showing compositions by lot of the dry bio-crude generated in the process shown in FIG. 2.

FIG. 7 shows the composition by lot of the dry bio-crude generated in the process shown in FIG. 2. The results are expressed as a percentage ratio of the mass of an individual component to the total mass of the dry bio-crude. The horizontal axis indicates the Lot ID numbers. In each column corresponding to one lot, from bottom to top, the first band shows moisture content; the second band shows protein content; the third band shows ash content; the fourth band shows fat content; the fifth band shows crude fiber content; and the sixth band shows the available carbohydrates.

FIG. 7 shows that the dry bio-crude was rich in carbohydrates, in the form of available carbohydrates and crude fiber.

Example 7

Wet and Dry Bio-Crude Yield

Figure 8:
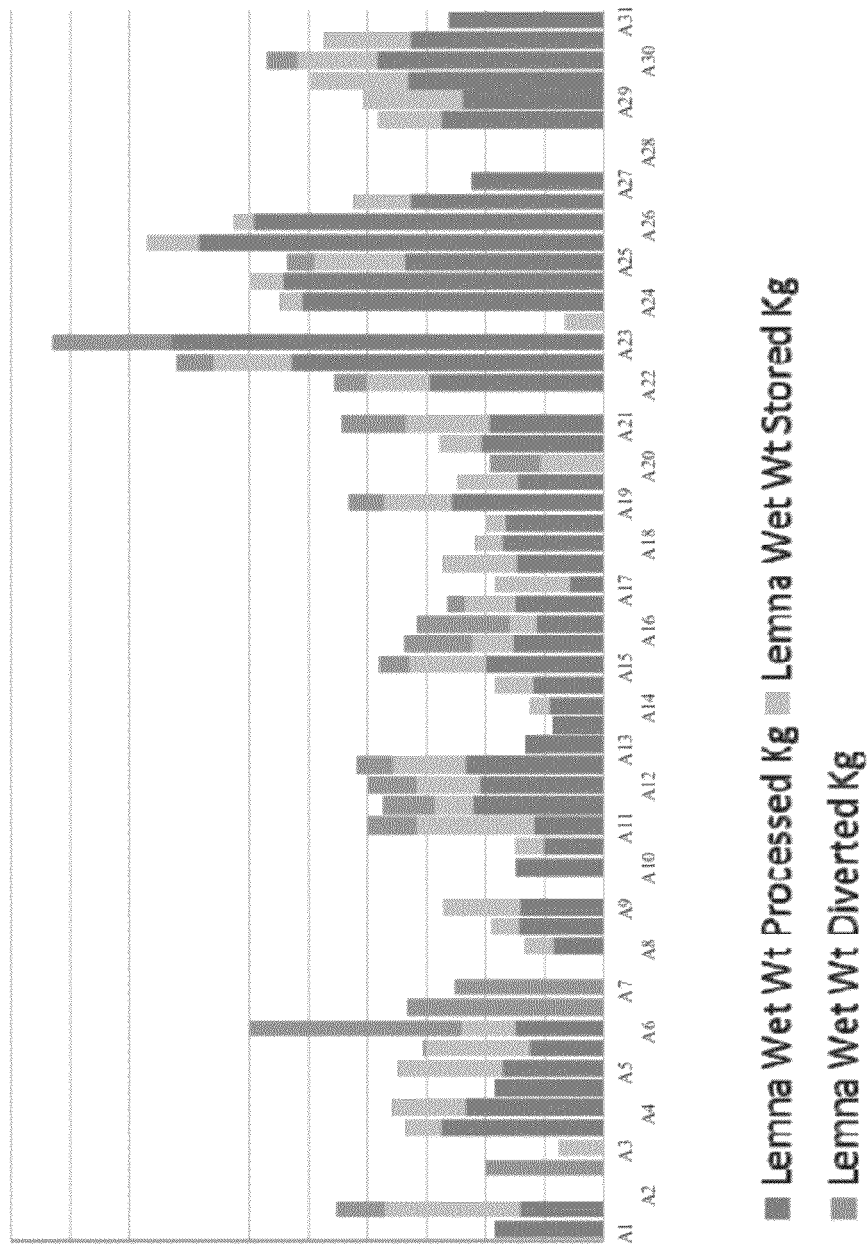
FIG. 8 is a bar graph showing the relative performance of a pilot farm over various episodes.

FIG. 8 shows the *Lemna* harvest volume of a pilot plant over two months. The dark grey band shows the weight of the wet lemna which was processed soon after harvesting; the light grey band shows the weight of wet lemna which was stored for later processing; and a band in medium grey shows the weight of wet lemna which was diverted for offsite processing.

Example 8

Solid Split in Unit Operations

Figure 9:
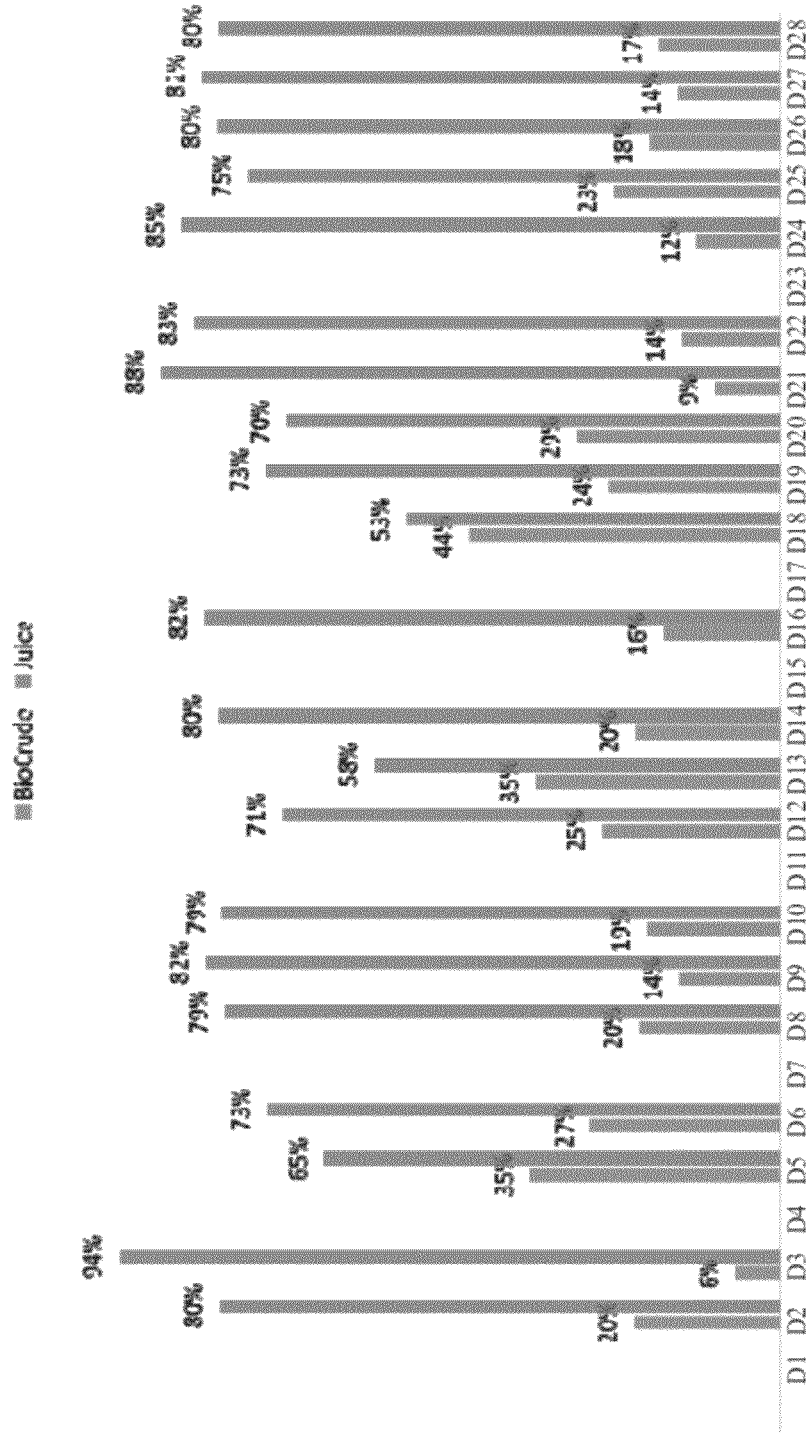
FIG. 9 is a bar graph showing an example of the solid split after fresh lemna was lysed and pressed as described in FIG. 2.

FIG. 9 shows an example of the solid split after the fresh lemna obtained as described above was lysed and pressed as described in FIG. 2. The pressing was carried out by a belt press and a screw press in series. The belt was flushed using belt filter wash water, and the washed belt filter solids were recycled to the screw press. The results are expressed as a percentage ratio of the mass of the solids in the BioCrude (corresponding to the wet bio-crude (D3) of FIG. 2) or in the juice (corresponding to the combined raw juice (E1) of FIG. 2) to that of the solids in the lysed biomass (at C1 in FIG. 2). These figures, and the figures relating to the solid split in various product streams in subsequent examples, were obtained by drying samples of both the biocrude and the juice to obtain the weight of solids therein. These numbers were added to obtain the assumed amount of solids in the lysed biomass. The horizontal axis indicates the Lot ID numbers. For each pair of columns for the same Lot ID, the left-hand column shows the amount of solids in the bio-crude, while the right-hand column shows the amount of solids in the juice. The average bio-crude solid mass was 23.5% of the mass of the lysed biomass, of which 21% was wet bio-crude, while 2.5% was solids washed off of the belt filter. The solids in the juice comprised, on average, 76.5% of the solids in the lysed biomass.

Figure 10:
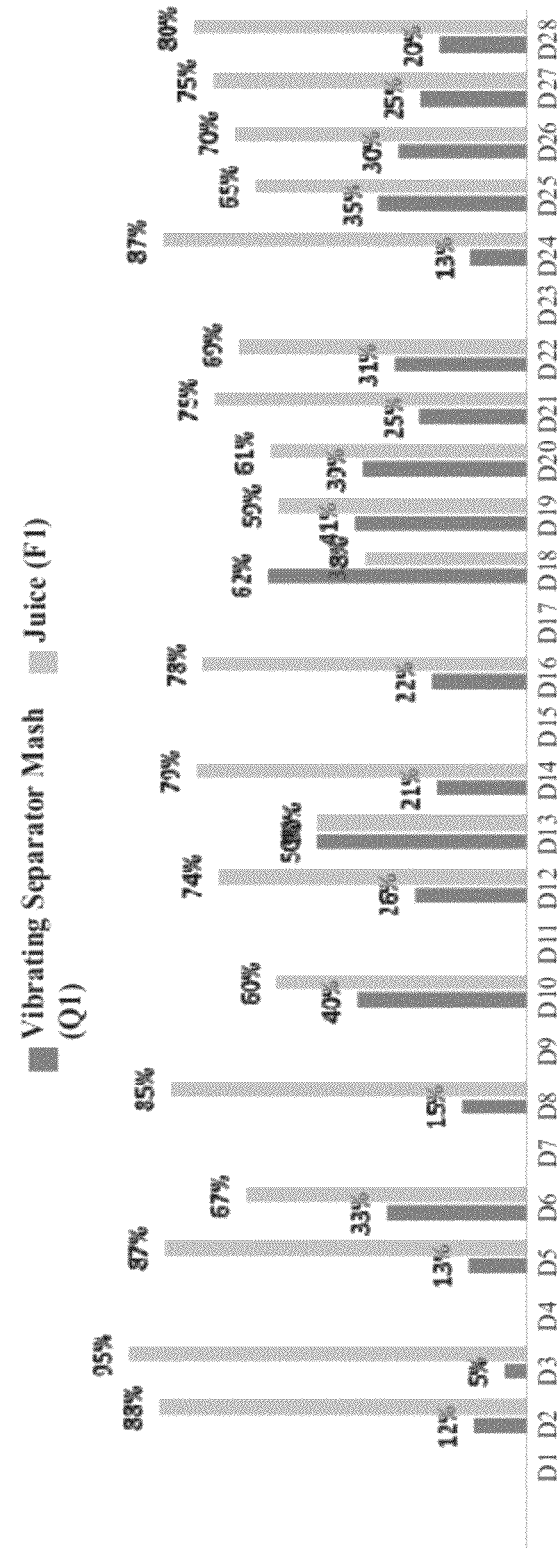
FIG. 10 is a bar graph showing an example of the solid split after combined raw juice was passed through a vibratory separator as shown in FIG. 2.

FIG. 10 shows an example of the solid split after the combined raw juice passed through the vibratory separator as shown in FIG. 2. The results are expressed as a percentage ratio of the mass of the solids in the mash (Q1, corresponding to "Mash (Recycled Solids)" (Q1) of FIG. 2) or in the juice (F1, corresponding to the "Filtered Juice" from juice tank 1 of FIG. 2) to that of the solids in the combined raw juice (E1) of FIG. 2. The horizontal axis indicates the Lot ID numbers. For each pair of columns for the same Lot ID, the left-hand column shows the result for the mash (Q1), while the right-hand column shows the results for the juice (F1).

FIG. 10 shows an example test result of the solids split for the vibrating separator.

Figure 11:
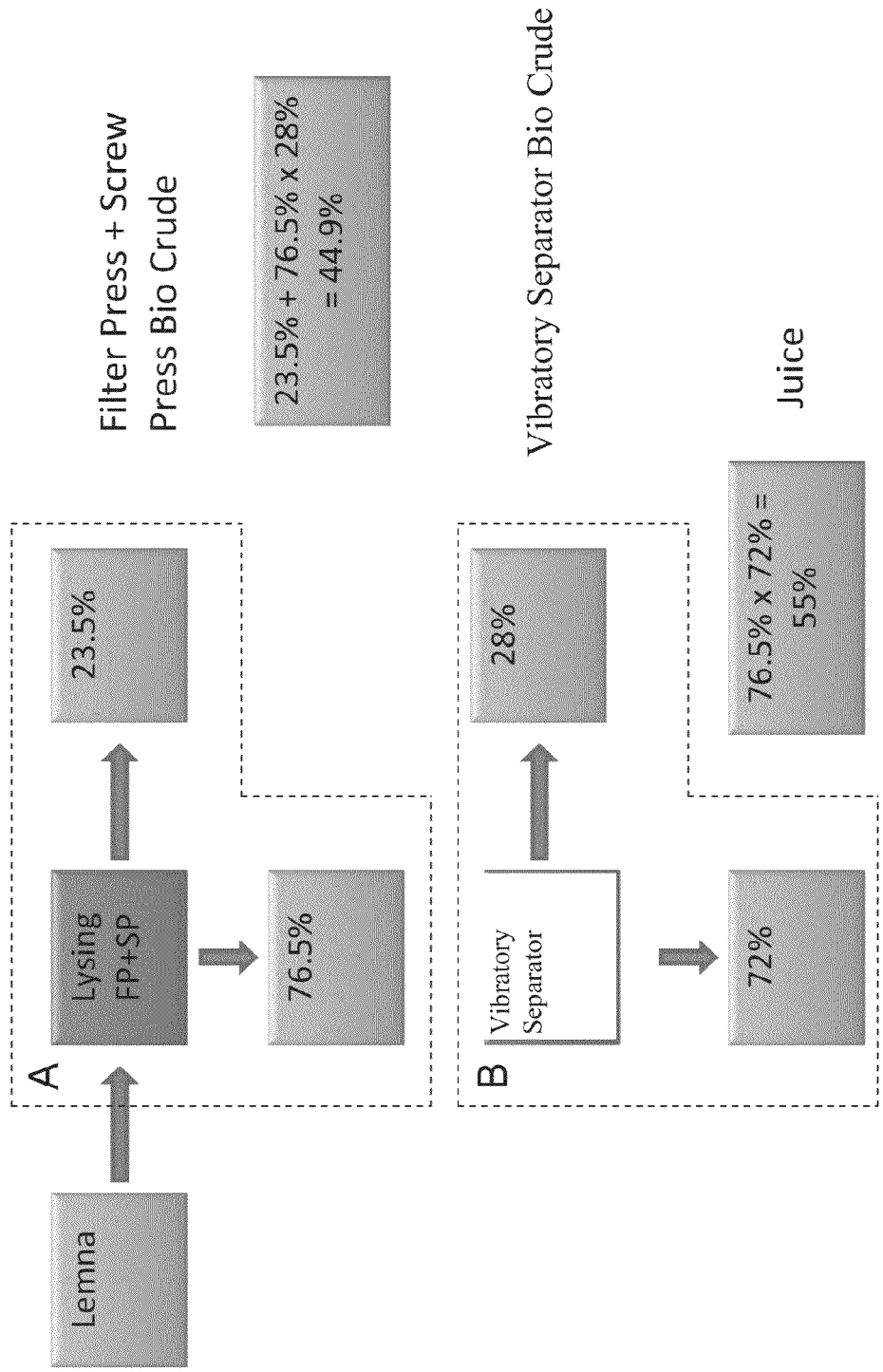
FIG. 11 shows an example calculation the material split using results shown in FIG. 10 and FIG. 11.

FIG. 11 shows an exemplary calculation of how one would calculate material split from FIG. 9 and FIG. 10. The area bounded by a dotted line and marked "A" corresponds to the results shown in FIG. 9; while the area bounded by a dotted line and marked "B" corresponds to the results shown in FIG. 10. In A, after lysing and pressing by a belt filter press (FP) and a screw press (SP), on average the solids in the bio-crude (corresponding to the "Wet Bio-Crude" (D3) of FIG. 2) comprised 23.5% of the solids in the fresh lemna biomass, while on average the solids in the juice (corresponding to the "Combined Raw Juice" (E1) of FIG. 2) comprised 76.5% of the solids in the fresh lemna biomass. In B, after passage through the vibratory separator in the second dewatering stage, on average the mash (Q1, corresponding to the "Mash (Recycled Solids)" of FIG. 2) comprised 28% of the solids in the combined raw juice, while on average the solids in the filtered juice (F1, corresponding to the "Filtered Juice" from juice tank 1 in FIG. 2) comprised 72% of the solids in the combined raw juice. Accordingly, on average the combined wet bio-crude, comprising both the wet bio-crude obtained after passage through the filter press and screw press and the recycled solids obtained after filtration of the combined raw juice using the vibratory separator, comprised 44.9% of the solids in the fresh lemna biomass, while on average the solids in the filtered juice comprised 55% of the solids in the fresh lemna biomass.

Figure 12:
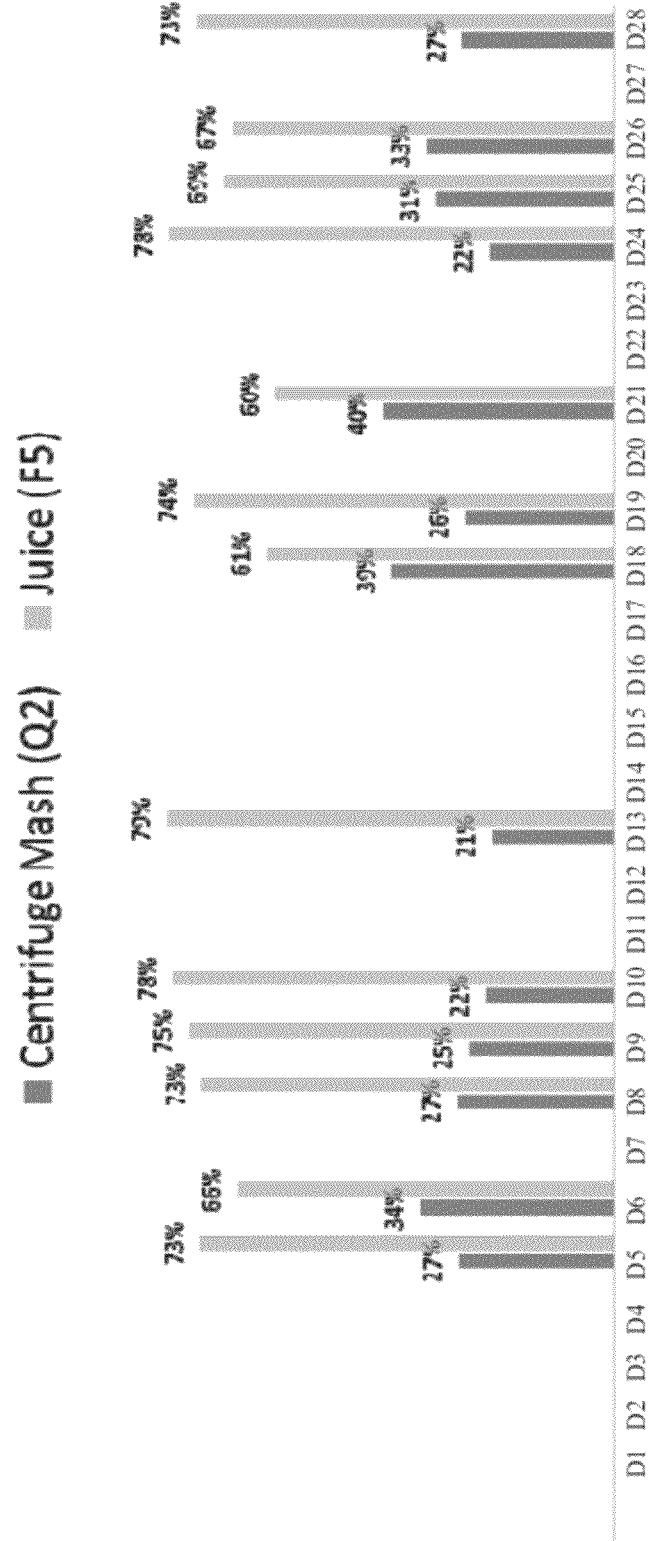
FIG. 12 is a bar graph showing an example test of the solid split after filtered juice went through clarification by centrifuge as shown in FIG. 2.

FIG. 12 shows the solid split after the filtered juice underwent clarification by centrifuge as shown in FIG. 2. The results are expressed as a percentage ratio of the mass of the solids in the centrifuged solids (Q2, corresponding to the "Centrifuged Solids from Filtered Juice" of FIG. 2) or in the juice (F5, corresponding to the "Spun Filtered Juice" of FIG. 2) to that of the solids in the filtered juice (F1) of FIG. 2. The horizontal axis indicates the Lot ID numbers. For each pair of columns for the same Lot ID, the left-hand column shows the result for the centrifuge mash (centrifuged solids, Q2), while the right-hand column shows that for the juice (F5).

FIG. 12 shows an example test of solid split of the clarification centrifuge.

Figure 13:
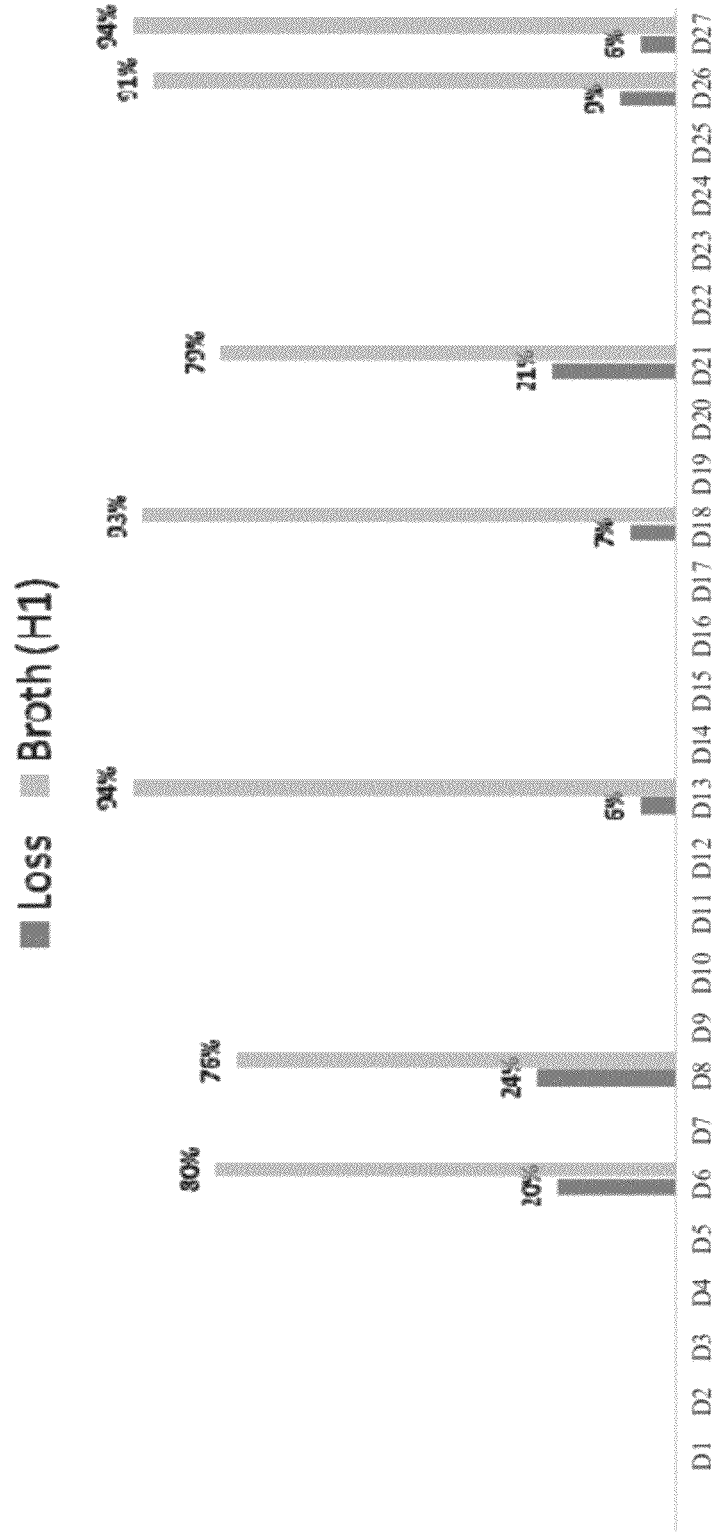
FIG. 13 is a bar graph showing an sample test of the solid split after spun filtered juice was precipitated for protein coagulation.

FIG. 13 shows an example test result of the solid split after the spun filtered juice was passed through the precipitator for protein coagulation. The results are expressed as a percentage ratio of the (calculated) lost solid mass ("Loss") or the mass of the solids in the broth (at H1 in FIG. 2) to that of the solids in the spun filtered juice before precipitation (F6 in FIG. 2). The horizontal axis indicates the Lot ID numbers. For each pair of columns for the same Lot ID, the left column indicates the lost mass, while the right column indicates the mass of the precipitator broth (H1).

FIG. 13 illustrates that the majority of solids are passed through the precipitator for further processing.

The solid split resulting from the protein separation by centrifuge was also assessed. In this example (step 6, FIG. 15) the solids in the liquor (liquid supernatant) included 70% of the solid mass of the broth before centrifugation, while the solids in the wet protein concentrate obtained from the pellet included 30% of the solids in the broth.

Figure 14:
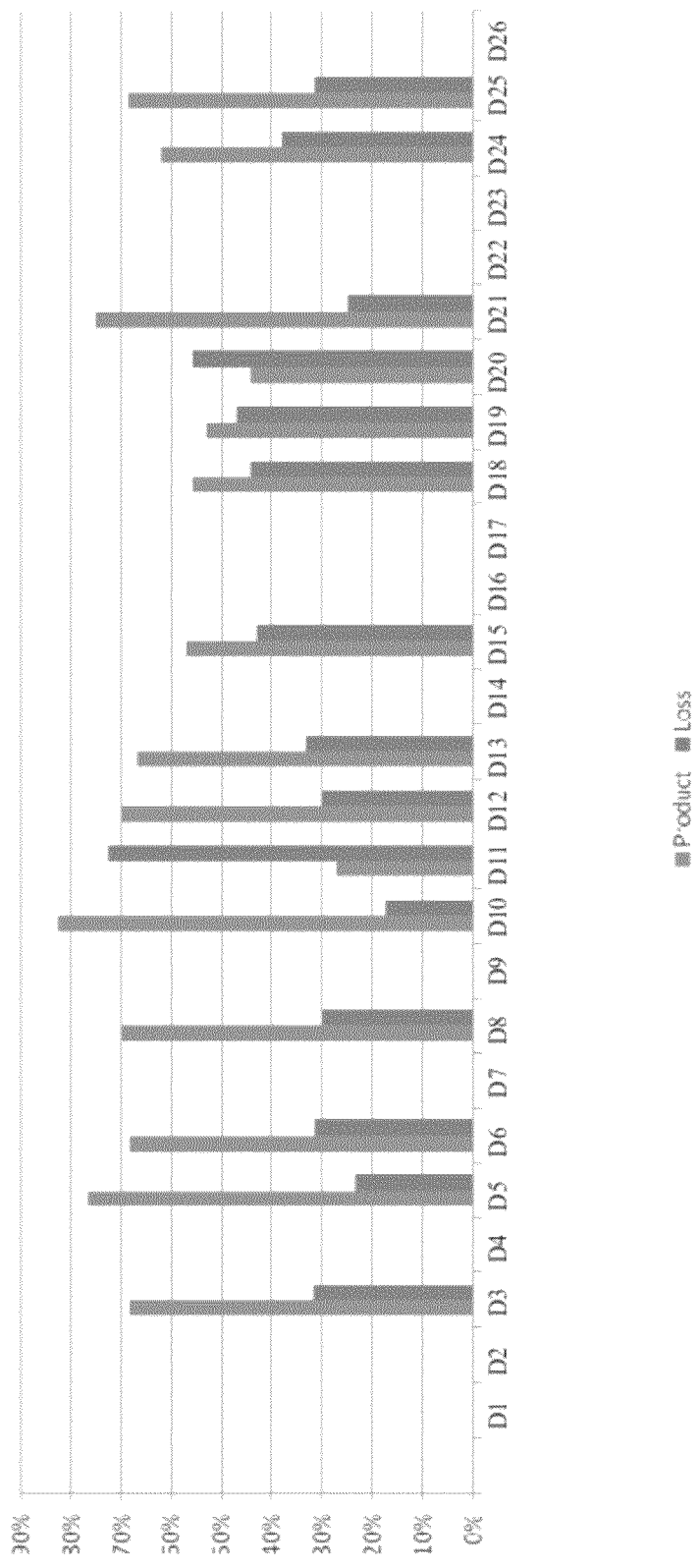
FIG. 14 is a bar graph showing an example of the product capture efficiency of a spray dryer as shown in FIG. 2.

FIG. 14 shows an example of product capture as it relates to the efficiency of the protein dryer. FIG. 14 shows that, on average, the dry protein concentrate comprised 63% of the solids mass of the wet protein concentrate, while on average 37% of the solids mass of the wet protein concentrate was lost in the drying procedure.

As an example, Table 5 summarizes the results shown in FIG. 9 through FIG. 14.

TABLE 5

Solid Split Summary

| Unit Operation | Step # | Solid Mass in Juice (Protein Pathway) | Solid Mass in Solid Product (Other/ BioCrude Pathway) | Total |
|---|---|---|---|---|
| Knife Mill | Step1 | 100.0% | 0.0% | 100% |
| Belt + Screw Press + Belt Filter | Step2 | 76.5% | 23.5% | 100% |
| Vibratory Separator | Step3 | 72.0% | 28.0% | 100% |
| Clarification Centrifuge | Step4 | 71.0% | 29.0% | 100% |
| Protein Precipitator | Step5 | 87.0% | 13.0% | 100% |
| Separation Centrifuge | Step6 | 30.0% | 70.0% | 100% |
| Spray Dryer | Step7 | 63.0% | 37.0% | 100% |

Figure 15:
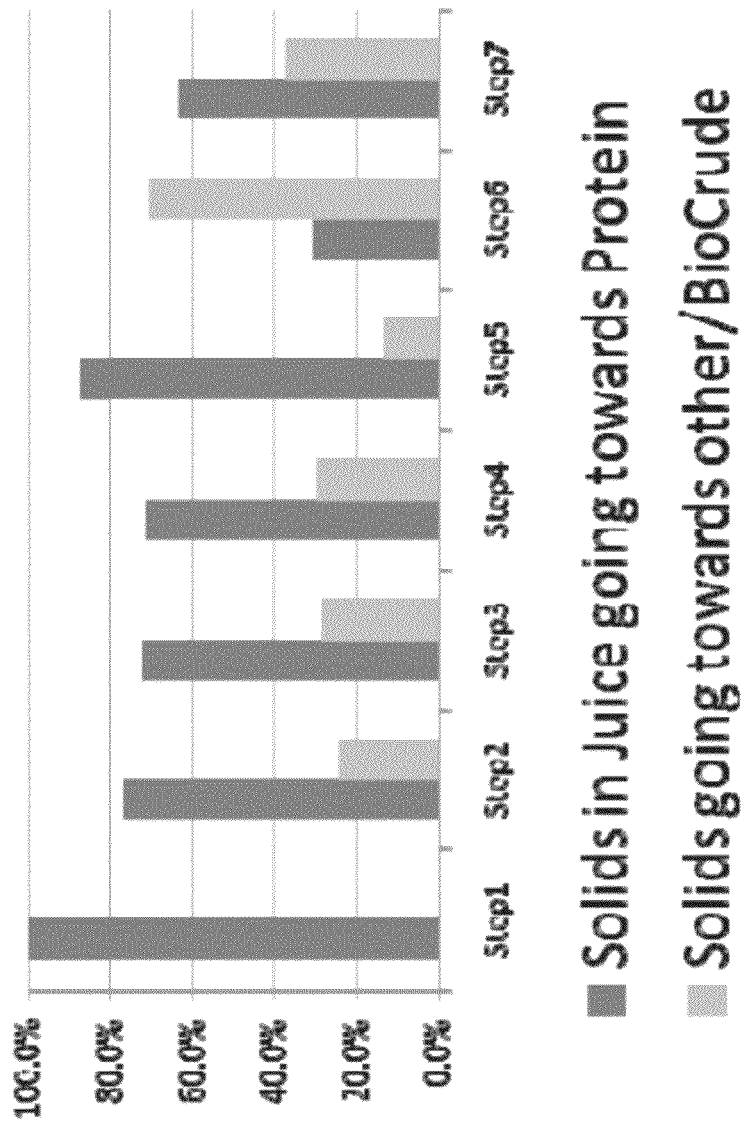
FIG. 15 is a bar graph showing an example of the solid split after each unit operation.

FIG. 15 shows an example of the results summarized in Table 5. For each pair of columns for the same step, the left-hand column indicates the proportion of the pre-treatment solid mass in the resulting juice going towards protein, while the right-hand column shows the proportion of the pre-treatment solid mass in the resulting solids going towards other/BioCrude.

Figure 16:
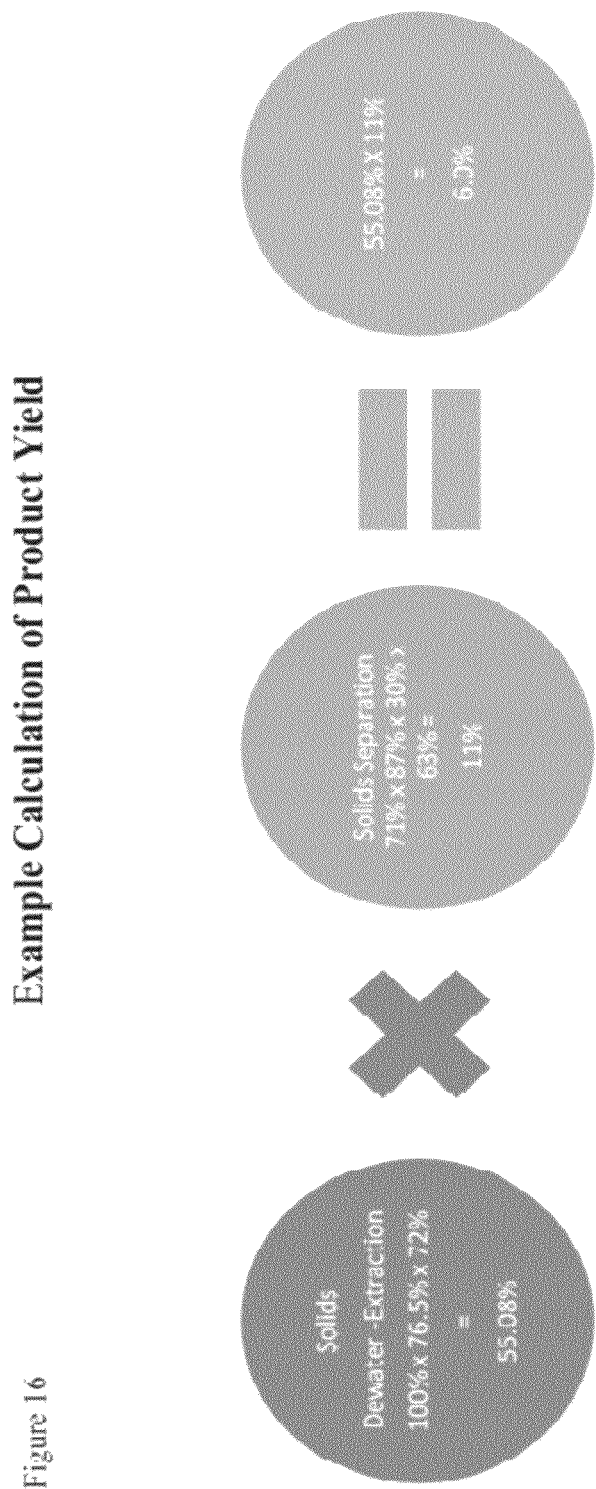
FIG. 16 illustrates how to calculate protein yield (dry protein concentrate) based on the mass flow of solids through the unit operations.

FIG. 16 illustrates an example of how to calculate protein production yield. Steps 1 through 3 of Table 5 and FIG. 15 comprise the "Solids Dewater-Extraction" in FIG. 16, while Steps 4 through 7 of Table 5 and FIG. 15 comprise the "Solids Separation" in FIG. 16. In this example, the dry protein concentrate obtained averaged 6% of the solid mass in the lemna biomass. This is confirmed by the amounts of dried protein obtained experimentally, as shown in FIG. 3.

Example 9

Flow Diagram of Exemplary Process of Protein Isolation

Figure 17:
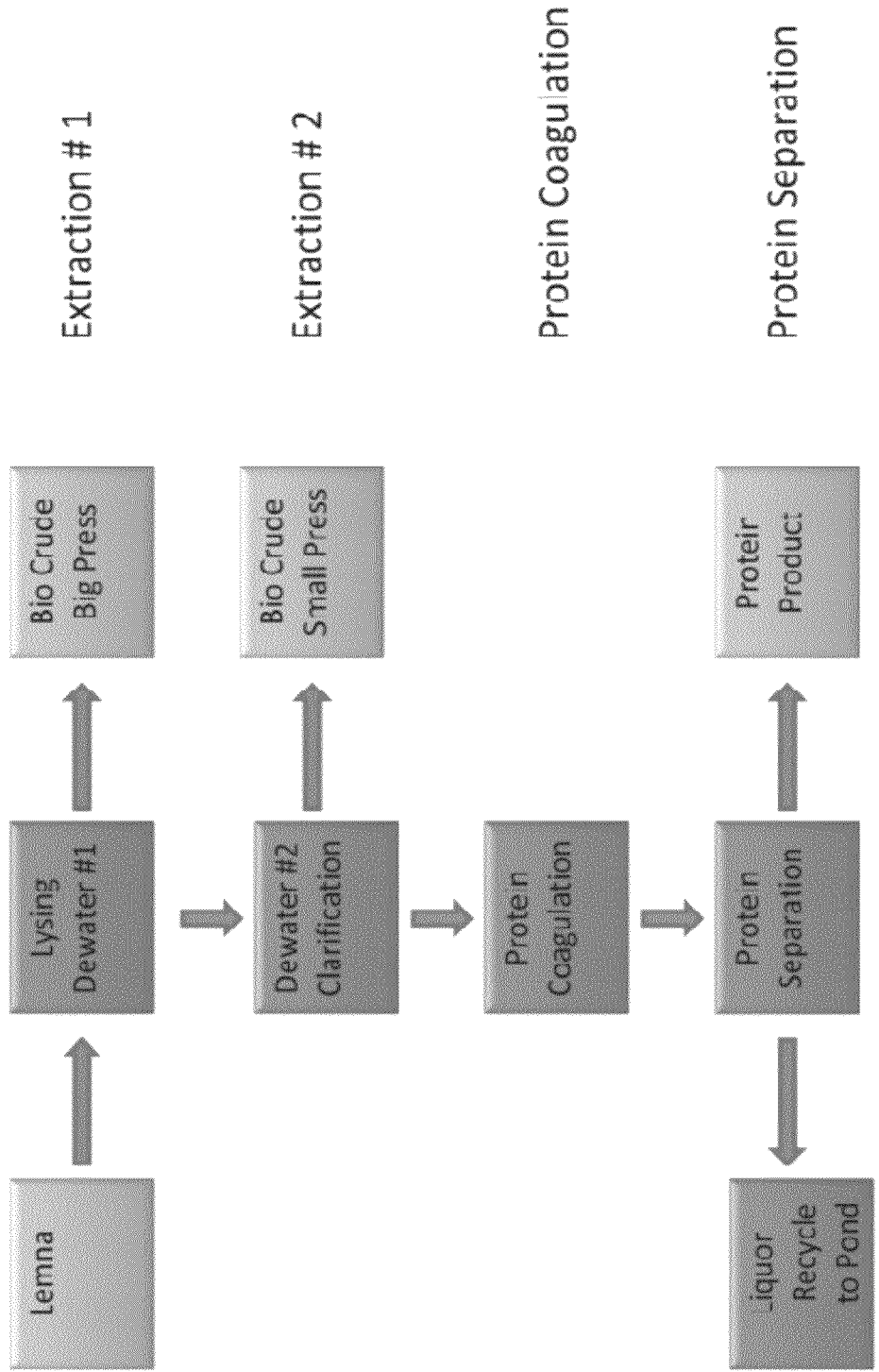
FIG. 17 is a flow diagram illustrating an exemplary process of isolating protein from lemna.

FIG. 17 shows a flow diagram of an exemplary process of isolating protein from lemna.

In overview, this process comprises the lysing and/or pressing of a lemna biomass (also referred to as biomass slurry or raw feedstock) to generate a juice and a bio-crude ("Bio Crude Big Press;" the process is termed "Lysing Dewater #1" and "Extraction #1"); filtering and/or clarifying the juice to generate another juice and further bio-crude ("Bio Crude Small Press;" the process is termed "Dewater #2 Clarification" or "Extraction #2"); coagulating protein from the filtered or clarified juice to generate a protein-containing broth (termed "Protein Coagulation"); and separating the broth to generate a protein product and a liquor (termed "Protein Separation"). The liquor is recycled to a pond (bioreactor).

Figure 18:
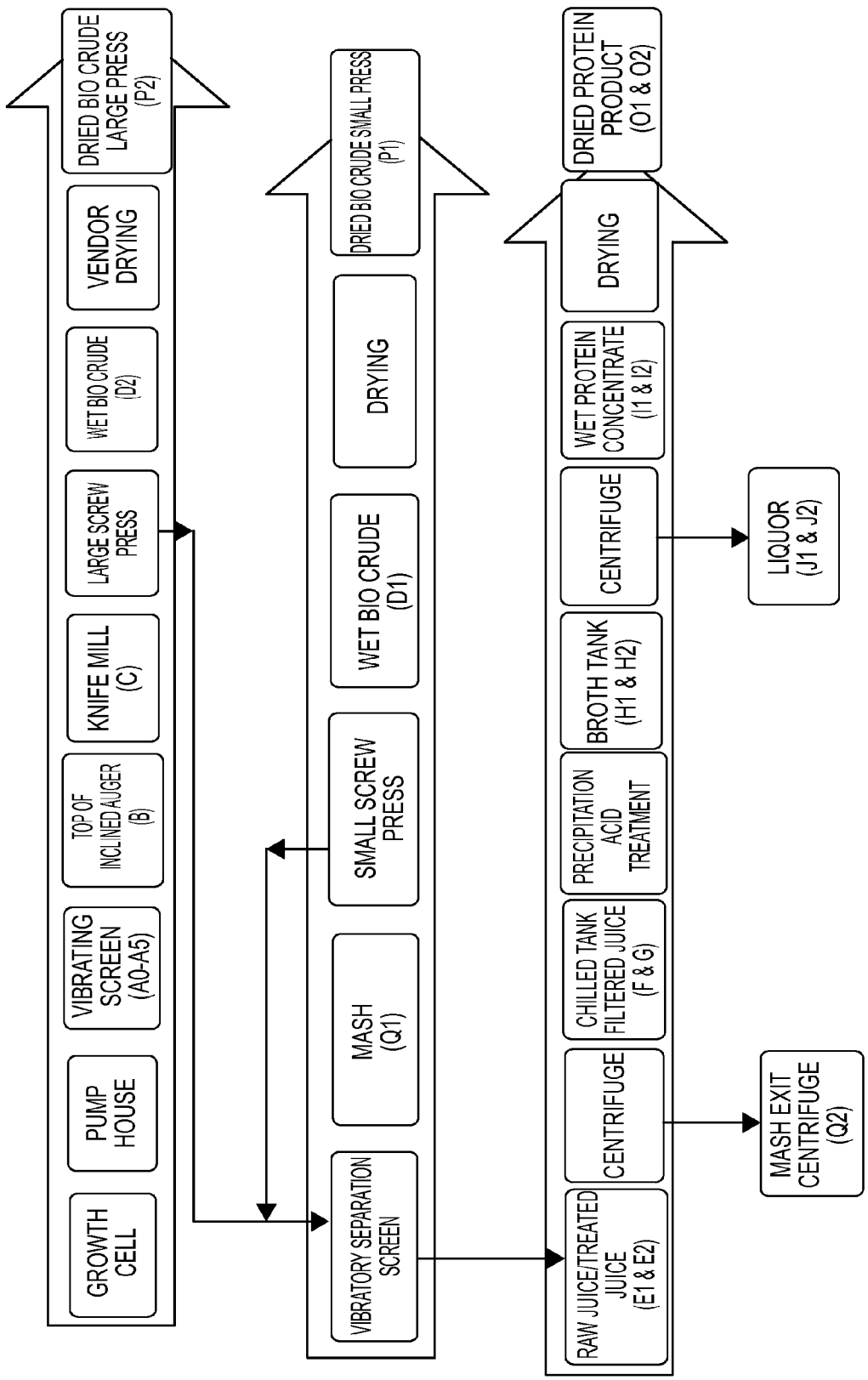
FIG. 18 is a more detailed flow diagram of that shown in FIG. 17 illustrating an exemplary process of isolating protein from lemna.

FIG. 18 contains a more detailed flow diagram depicting the exemplary process for isolating protein from lemna shown in FIG. 17.

As shown in FIG. 18, lemna are cultured in a growth system as described above. The biomass slurry comprising harvested lemna (also referred to as raw feedstock) is transferred via a pumping system (e.g., Pumping House) onto a vibrating screen (A0-A5), and then to the top of an inclined auger (B). From the top of the inclined auger (B), the biomass slurry is conveyed to a knife mill (C) where the wet biomass fronds are lysed to expose the internal water and protein. The lysed biomass is conveyed to a large screw press in which the lysed biomass is pressed to generate wet bio-crude (D2) and a juice. The wet bio-crude (D2) is dried ("Vendor Drying") to generate a dried bio-crude (termed a "Dried Bio Crude Large Press") (P2), while the juice is filtered using a vibratory separator to generate a mash (recycled solids, Q1) and a juice (termed "RawJuice/Treated juice") (E1 & E2). The mash (Q1) is conveyed to a small screw press for further pressing to generate a second juice and further wet bio-crude (D1). This wet bio-crude (D1) is dried by spin flash drying to generate a dried bio-crude (termed "Dried Bio Crude Small Press") (P1), while the second juice is conveyed to the vibratory separator for filtering. The raw or treated juice (E1 & E2) exiting the screen is clarified using a centrifuge to generate a mash ("Mash Exit Centrifuge") (Q2) and a clarified juice. This step is also termed "Centrifuge #1." The clarified juice is stored in a chilled tank, where it is termed "Chilled Tank Filtered Juice" (F&G). The clarified juice then passes through a precipitator or an acid treatment for coagulating the proteins, to generate a broth comprising a wet protein concentrate. The broth is stored in a broth tank (H1 & H2). In order to separate the protein from the remaining part of the broth, the broth is centrifuged to generate a liquor (J1 & J2) and a wet protein concentrate (I1 & I2). This step is also termed "Centrifuge #2." The liquor is recycled back to a growth pond (bioreactor) or discarded. The wet protein concentrate is washed or diluted using water. The wet protein concentrate is dried by spray drying to generate a dried protein product (dry protein concentrate, O1 & O2). The dried protein product is packaged for further use or analysis.

Example 10

Solid Split in Unit Operations

Lemna is processed following the process shown in FIG. 17 and FIG. 18 and described in Example 9.

Figure 19:
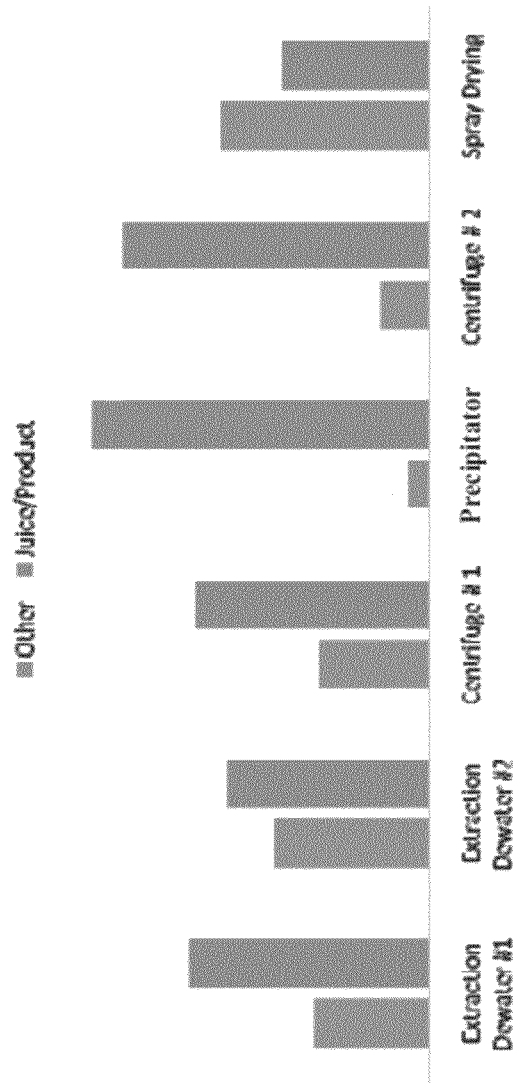
FIG. 19 is a bar graph showing the relative solid split by unit operation in the process shown in FIG. 17 and FIG. 18.

FIG. 19 shows the relative solid recovery by unit operation in the process shown in FIG. 17 and FIG. 18. The results are illustrated as a percentage ratio of the mass of the solids in the juice or protein product (raw juice or treated juice E1 & E2, clarified juice, or broth) or in other outputs (mash, wet bio-crude, liquor, etc.) to that of the solids in the initial starting material of each individual unit operation. The horizontal axis indicates the unit operations. "Extraction Dewater #1" corresponds to "Extraction #1" of FIG. 17; "Extraction Dewater #2" corresponds to "Extraction #2" of FIG. 17; "Precipitation" corresponds to the protein coagulation process in a precipitator of FIG. 18; while the processes termed "Centrifuge #1," "Centrifuge #2," and "Spray Drying" refer to the same processes as those shown in FIG. 18. For each pair of columns for the same Lot ID, the left-hand column shows the biocrude stream and the right hand column shows the protein stream.

Figure 20:
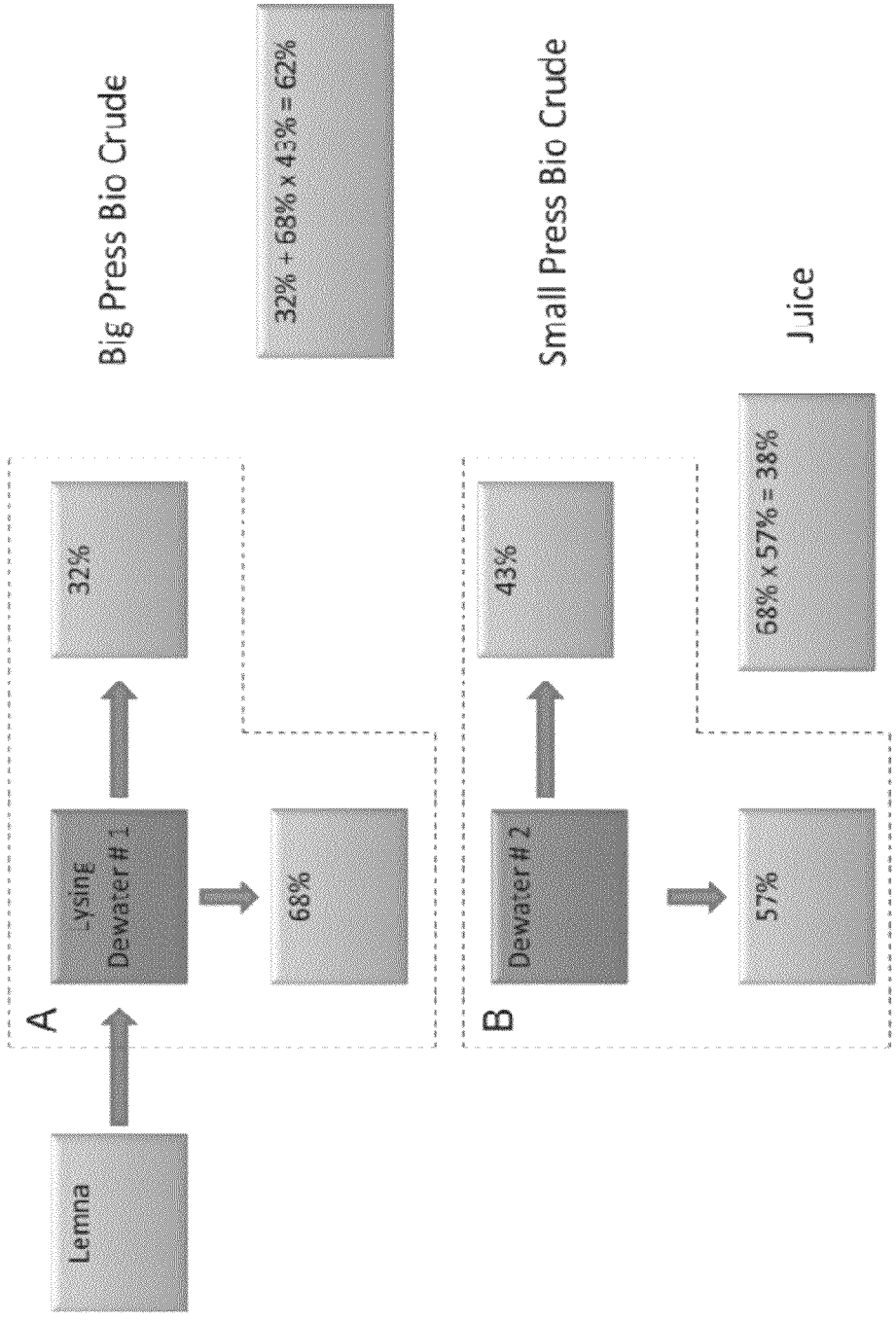
FIG. 20 shows an example of how to calculate the material split following Extraction Dewater #1 and Extraction Dewater #2 shown in FIG. 19.

FIG. 20 shows an example of the solid split resulting from the Extraction Dewater #1 and Extraction Dewater #2 processes, summarized in FIG. 19. The area encircled by a dotted line and labeled "A" corresponds to the Extraction Dewater #1 process, and the area encircled by a dotted line and labeled "B" corresponds to the Extraction Dewater #2 process. FIG. 20 shows that in this example, after the Extraction Dewater #1 and Extraction Dewater #2 processes, averagely 62% of the solids in the lemna biomass is present in the bio-crude, including the "Big Press Bio Crude" and "Small Press Bio Crude" (also referred to as Bio Crude Small Press), while 38% of the solids in the original lemna biomass is present in the juice.

Figure 21:
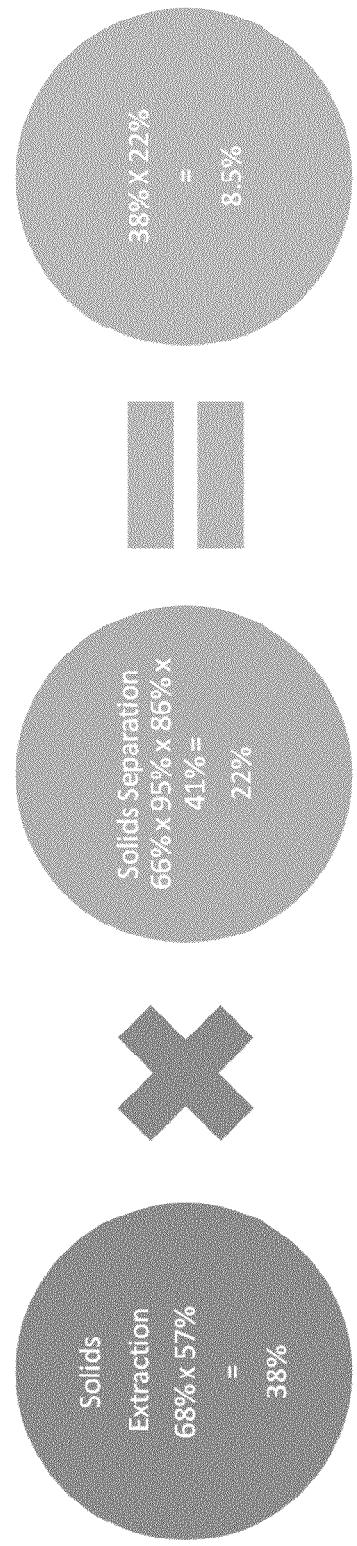
FIG. 21 illustrates an example of how to calculate yield (dry protein concentrate) based on the mass flow of solids through the unit operations.

FIG. 21 provides and example of how to calculate product yield of dry protein concentrate based on the mass flow through the unit operations. The "Solids Extraction" of the Figure comprises the Extraction Dewater #1 and Extraction Dewater #2 processes of FIG. 19, while the "Solids Separation" of the Figure comprises the "Centrifuge #1," "Precipitation," "Centrifuge #2," and "Spray Drying" processes of FIG. 19. The dry protein concentrate averages 8.5% of the original lemna biomass by weight.

Example 11

Protein Recovery in Unit Operations

Lemna biomass is processed in accordance with the processes shown in FIG. 17 and FIG. 18 and described in Example 9.

Figure 22:
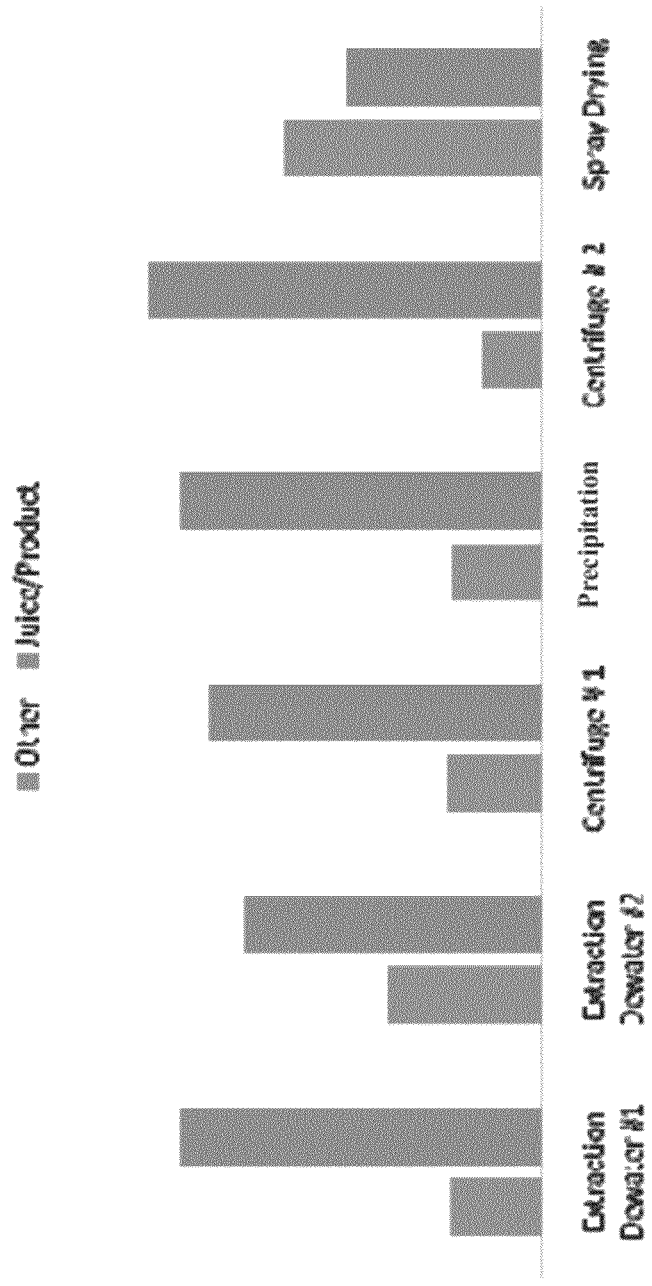
FIG. 22 is a bar graph showing the relative protein recovery by unit operation in the process shown in FIG. 17 and FIG. 18.

FIG. 22 shows the protein recovery by unit operation in the processes shown in FIG. 17 and FIG. 18. The results are expressed as a percentage ratio of the mass of the protein or protein-containing juice or of the other outputs that lead to bio-crude or other outputs (mash, wet bio-crude, liquor, etc.) to the mass of the composition forming the input of that individual unit operation. The horizontal axis indicates the individual unit operations. "Extraction Dewater #1" corresponds to "Extraction #1" of FIG. 17; "Extraction Dewater #2" corresponds to "Extraction #2" of FIG. 17; "precipitator" corresponds to the protein coagulation process in a precipitator depicted in FIG. 18; and "Centrifuge #1," "Centrifuge #2" and "Spray Drying" correspond to the analogous processes in FIG. 18, respectively. For each pair of columns corresponding to the same Lot ID number, the left-hand column shows is the results for the bio-crude and other products, while the right-hand column shows the results for the protein and protein-containing juice. For example, the initial input to the Extraction Dewater #1 process is lemna biomass; FIG. 22 shows that after the biomass goes through the Extraction Dewater #1 process, on average the bio-crude ("Bio Crude Big Press") comprises 20% of the mass of the input biomass, while on average the resulting juice comprised 80% of the lemna biomass.

Figure 23:
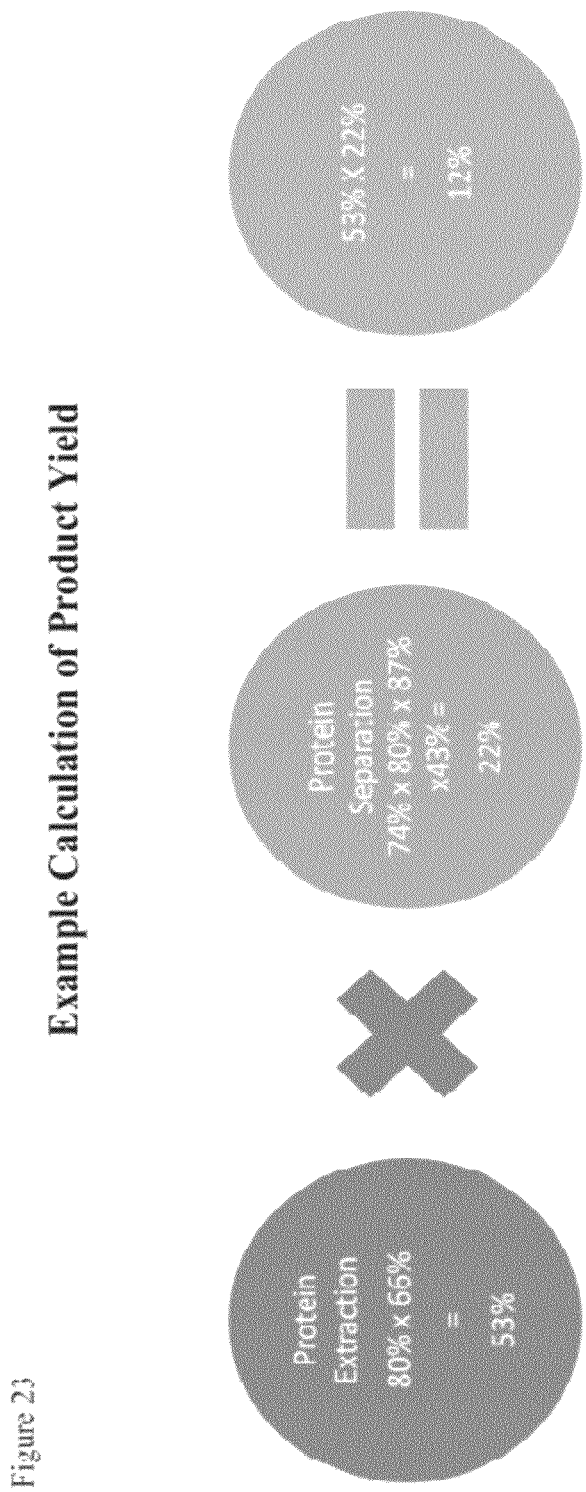
FIG. 23 illustrates provides an example of how to calculate protein yield based on the mass flow of protein through the unit operations.

FIG. 23 illustrates how to calculate the protein yield based on the mass flow through the unit operations. In this figure, "Protein Extraction" comprises the Extraction Dewater #1 and Extraction Dewater #2 processes of FIG. 22, while "Protein Separation" comprises the Centrifuge #1, Precipitation, Centrifuge #2 and Spray Drying processes of that figure. The protein yield is, on average, 12% of the lemna biomass by weight.

Example 12

Solid Split in Unit Operations

*Lemna* biomass was processed in accordance with the processes shown in FIG. 17 and FIG. 18 and described in Example 9.

Figure 24:
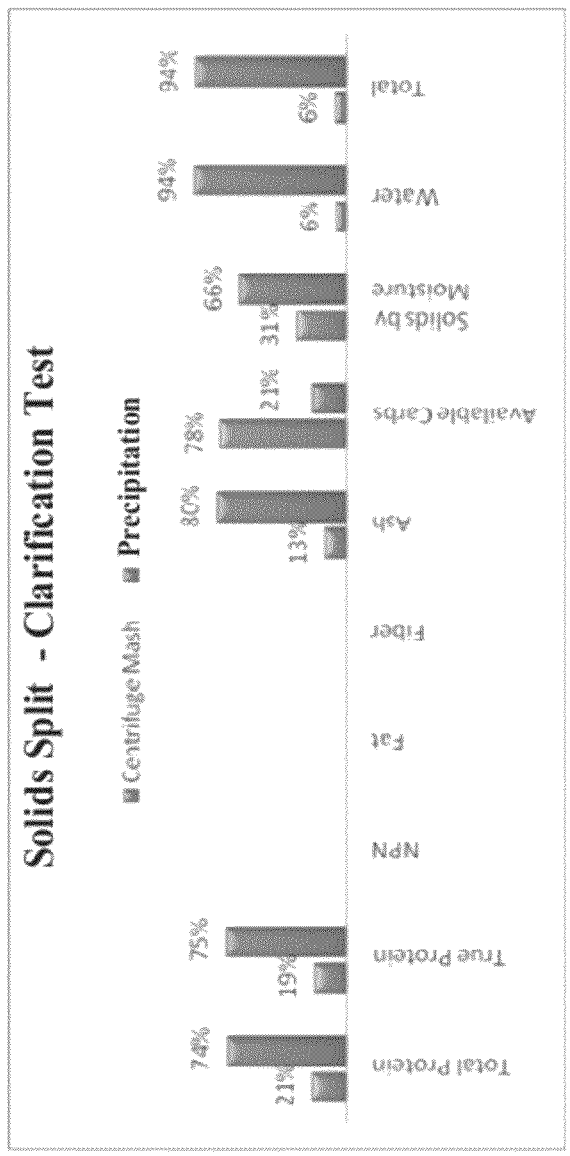
FIG. 24 is a bar graph showing the solid split after raw juice/treated juice (E1 & E2) went through clarification by centrifuge.

FIG. 24 shows the solid split after the raw or treated juice (E1 & E2) underwent clarification by centrifuge. This clarification corresponds to the first centrifuge process in FIG. 18, which generates a mash (in FIG. 18, the "Mash Exit Centrifuge" (Q2)) and a filtered juice. The "Mash Exit Centrifuge" (Q2) of FIG. 18 corresponds to the "Centrifuge Mash" for which composition data are provided in FIG. 24, while the filtered juice of FIG. 18 corresponds to the broth before precipitation for which data is also shown in FIG. 24. The results are expressed as a percentage ratio of the mass of an individual component of the centrifuge mash or of the broth before precipitation to that of the same component in the material subjected to the clarification process, which in this case was raw or treated juice (E1 & E2). The horizontal axis indicates the components. For each pair of columns for the same component, the left-hand column shows the results for the centrifuge mash, while the right-hand column shows the results the broth before precipitation.

Figure 25:
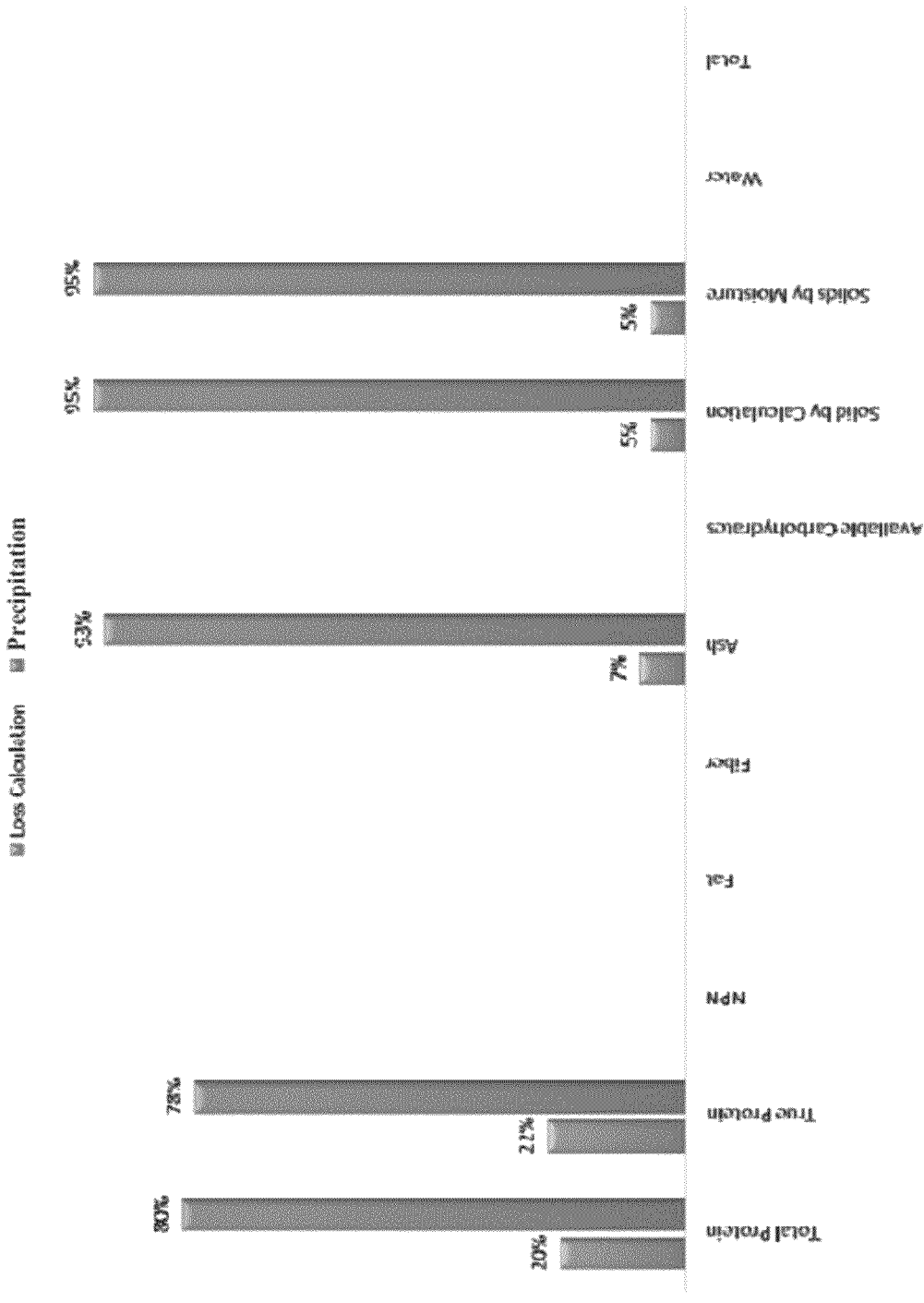
FIG. 25 is a bar graph showing the solid split after clarified juice was pasteurized for protein coagulation.

FIG. 25 shows the solid split after the filtered juice underwent precipitation for protein coagulation. The precipitation of this figure corresponds to the process of heat-induced protein coagulation the precipitator of FIG. 18. "Loss Calculation" indicates the calculated amount of solids lost in the precipitation procedure, while "Broth After Precipitation" indicates the broth obtained after the precipitation procedure. The results are expressed as a percentage ratio of the mass of an individual component in the loss calculation or in the broth after precipitation to that of the same component in the material that was pasteurized procedure, which was the broth before precipitation, the composition of which was shown in FIG. 24. The horizontal axis indicates the various components. For each pair of columns for the same component, the left-hand column shows the results for the calculated loss, while the right-hand column shows the amount of the component in the broth after precipitation.

Figure 26:
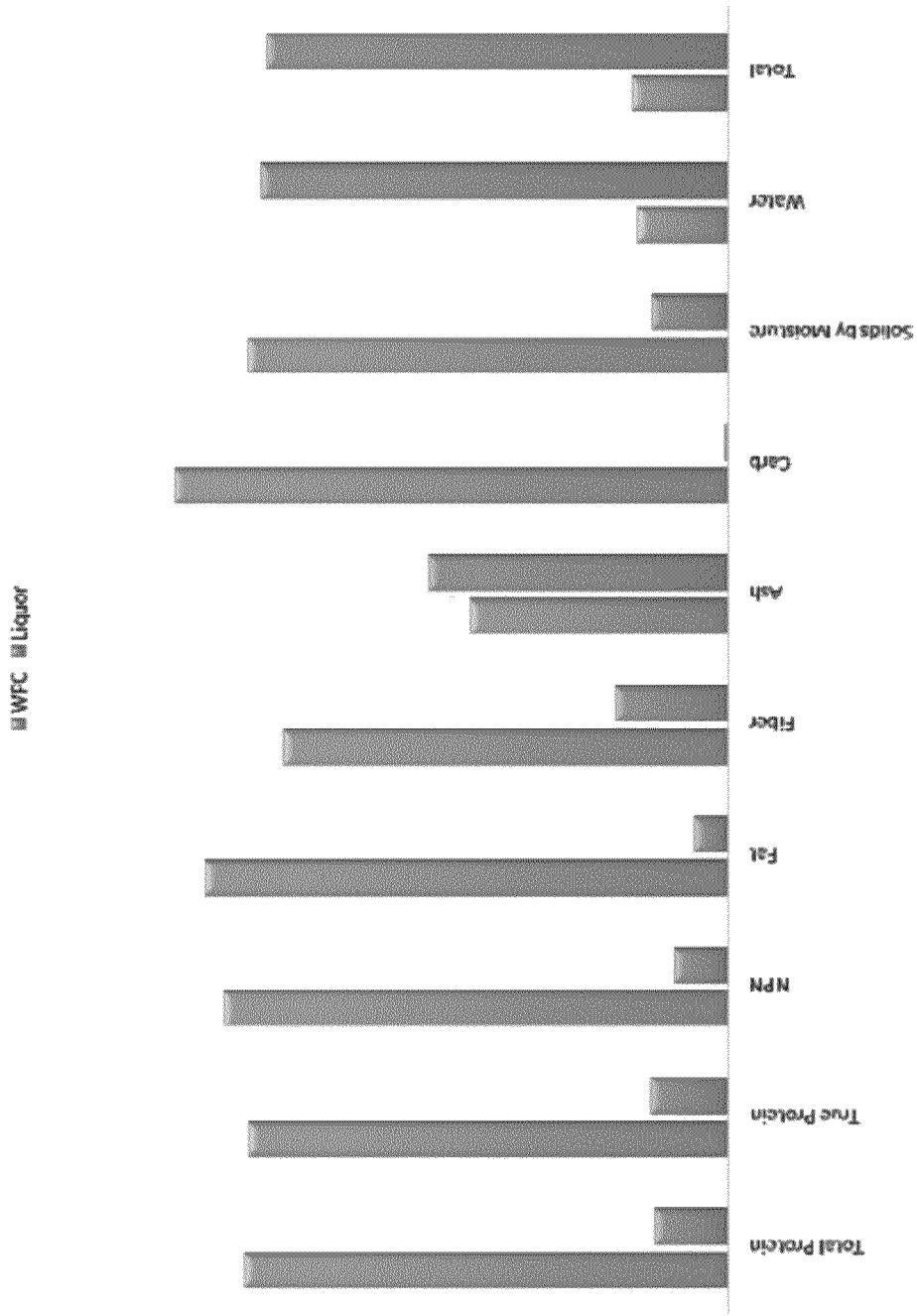
FIG. 26 is a bar graph showing the relative solid split after broth generated during protein coagulation was passed through a centrifuge for protein separation.

FIG. 26 shows the solid split after the broth resulting from the protein coagulation process was centrifuged to separate out the proteins (this corresponds to the Centrifuge #2 process in FIG. 18). "WPC" refers to the wet protein concentrate obtained after the liquor is removed from the broth after precipitation. The results are expressed as a percentage ratio of the mass of an individual component in the WPC or in the liquor to that of the same component in the material subjected to the Centrifuge #2 process, which was the broth after precipitation of FIG. 25. The horizontal axis indicates the various components. For each pair of columns for the same component, the left-hand column shows the amount of the component in the WPC, while the right-hand column shows the amount of the component in the liquor.

Figure 27:
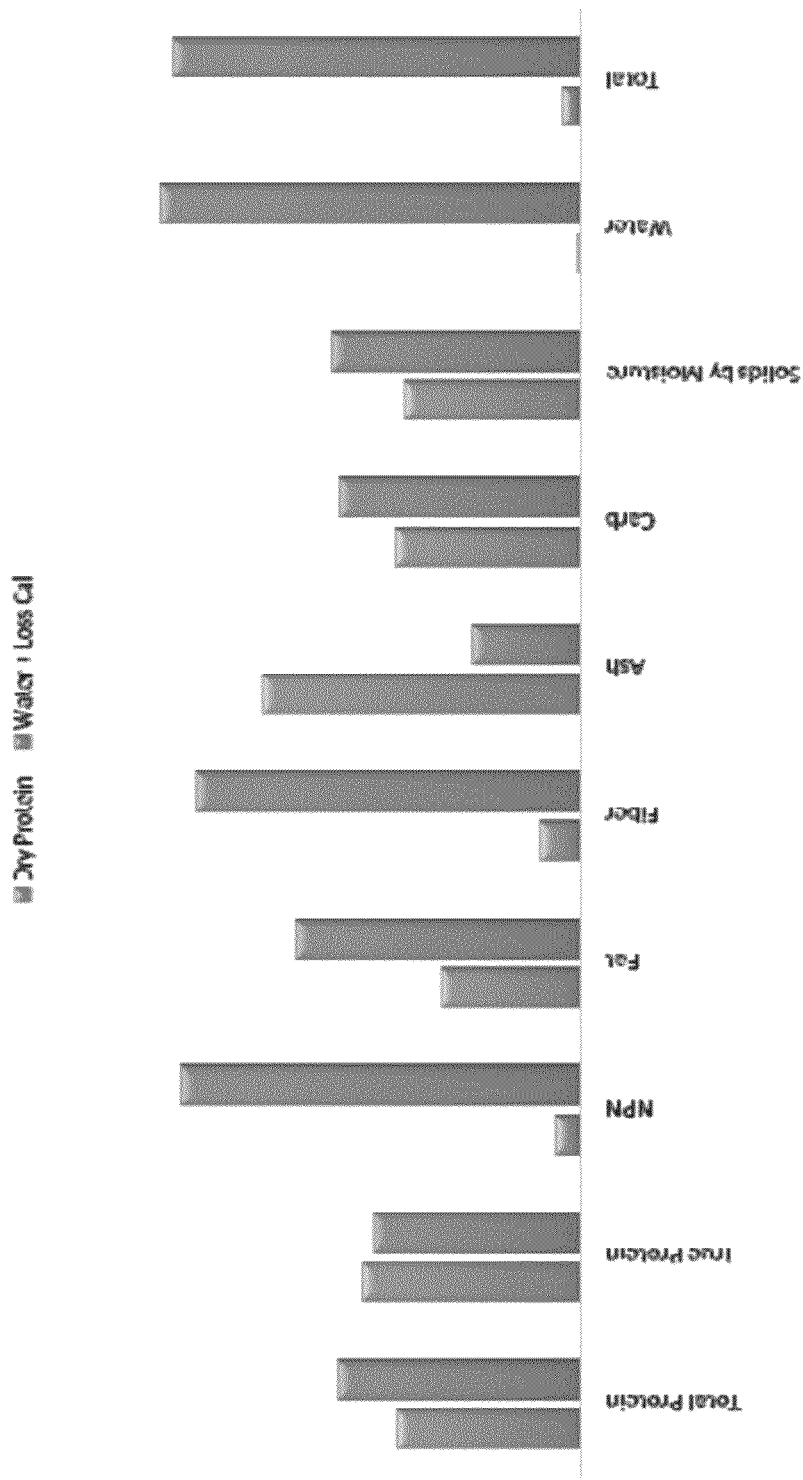
FIG. 27 is a bar graph showing the relative solid split after wet protein concentrate was dried by spray drying.

FIG. 27 shows the solid split after the wet protein concentrate was spray-dried. Spray drying the WPC generated by the second centrifugation generated a dry protein concentrate ("Dry Protein"). Some solid mass was lost ("Water+Loss Ca"). The results are expressed as a percentage ratio of the mass of an individual component in the dry protein or in the lost mass to that of the same component in the material that was spray-dried, which was the wet protein concentrate obtained from the second centrifugation. The horizontal axis indicates the various components. For each pair of columns for the same component, the left-hand column shows the amount of the component in the Dry Protein, while the right-hand column shows the amount of the component in the lost mass.

Figure 28:
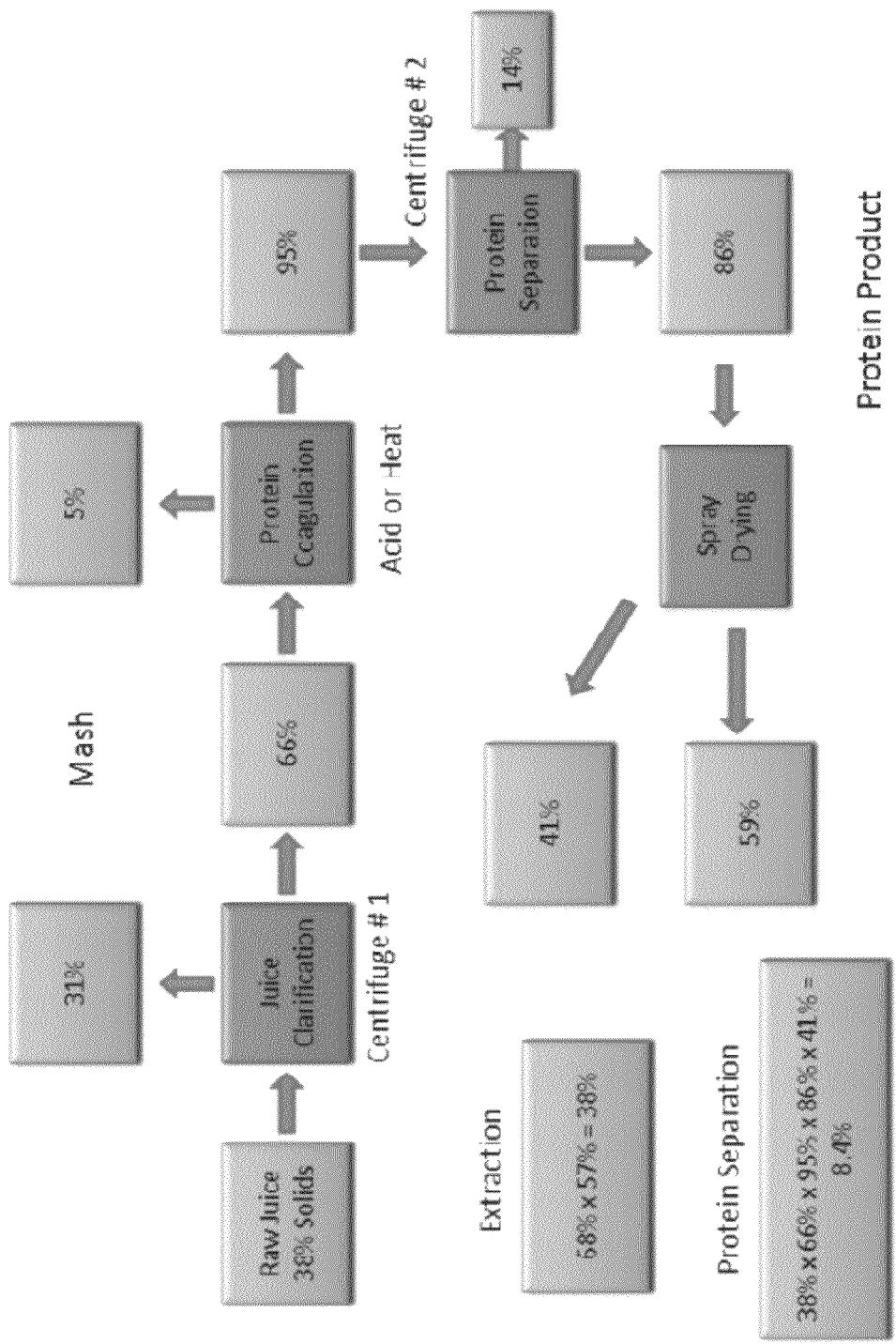
FIG. 28 shows a test protocol scenario with examples of the mass flow of the solids shown in FIG. 24-FIG. 27.

FIG. 28 shows a summary of the mass flow related to the results shown in FIG. 24-FIG. 27. After the extraction of the solids from the biomass (including Extraction #1 and/or Extraction #2 shown in FIG. 17), 38% of the solids in the original biomass remained in the raw juice. The raw juice contained, on average, 38% of the solids in the original lemna biomass. The raw juice was subjected to centrifugation (Centrifuge #1 in FIG. 28) to clarify the juice. This generated a mash (solid pellet) comprising, on average, 31% of the solids in the raw juice, and a juice (supernatant) comprising, on average, 66% of the solids in the raw juice. The juice was heat- or acid-treated to coagulate the proteins, generating a broth. On average, 5% of the solids present in the juice before treatment were lost in the process of the treatment, while on average 95% of the solids present in the juice before treatment remained in the broth after treatment. This treated broth was then centrifuged (Centrifuge #2) in order to separate the proteins; in this process, on average, 14% of the solids in the broth were lost, while 86% of the solids in the broth remained in the protein product (wet protein concentrate). The protein product was spray dried, in the course of which, on average, 41% of the solids in the wet protein concentrate were lost, while 59% of the solids in the wet protein concentrate remained in the final protein product (dry protein concentrate). Accordingly, on average, 8.4% of the solids in the lemna were converted to the final protein product (dry protein concentrate). This result agrees with that shown in FIG. 21.

Example 13

Process Flow Diagram and Sampling Points

Figure 29:
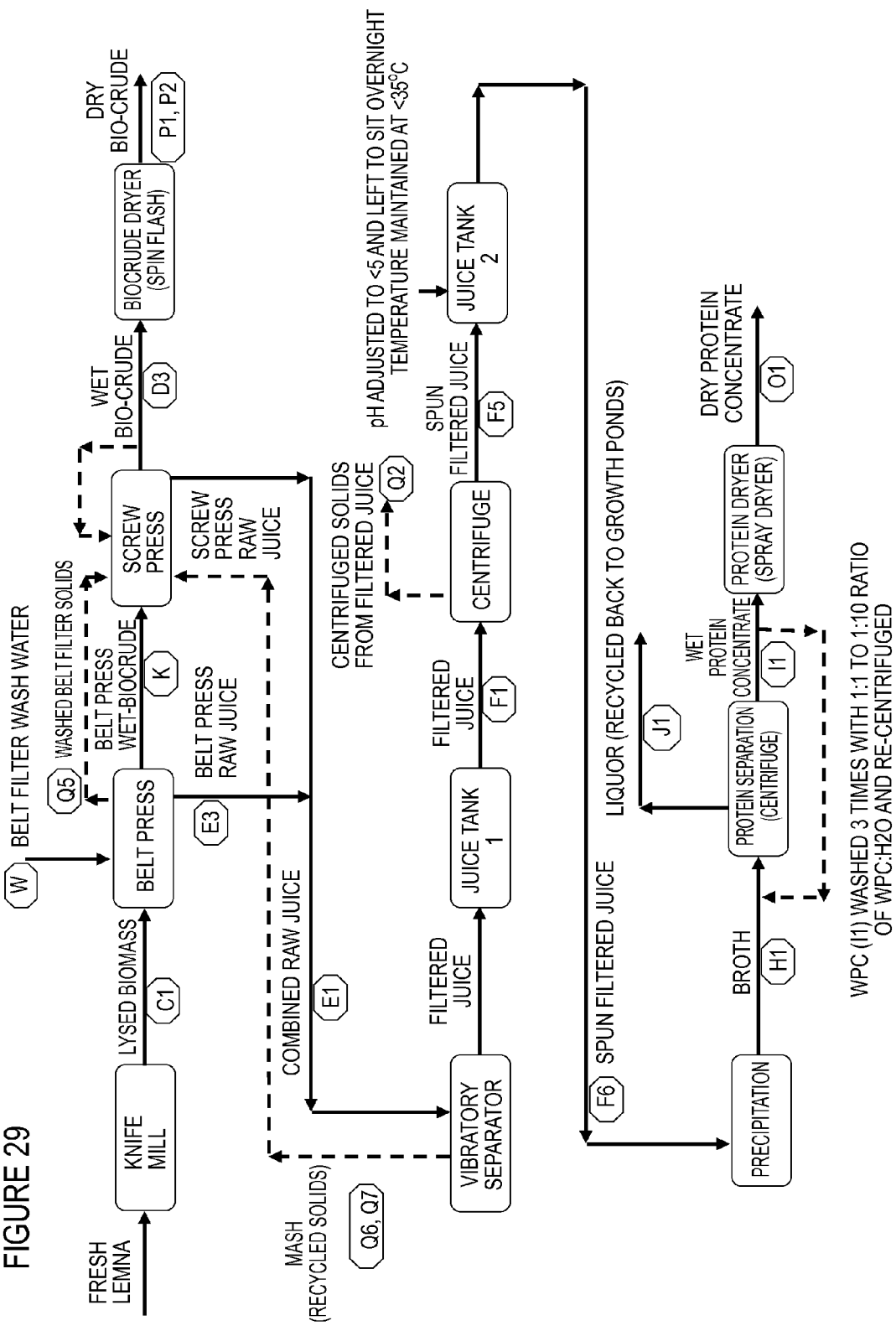
FIG. 29 is a flow diagram illustrating an exemplary process of isolating protein and other products from fresh lemna.

FIG. 29 shows a flow diagram of an exemplary process of isolating protein from an aquatic species, e.g., fresh lemna. The process was tested by experiments.

Fresh lemna (also referred to as biomass slurry or raw feedstock) are conveyed to a knife mill where the wet biomass fronds are lysed to expose the internal water and protein. The lysed biomass is conveyed to a belt press with belt filter wash water, and the lysed biomass is pressed to generate a first solid phase (identified in the Figure as "Belt Press Wet-Biocrude") and a juice (identified in the Figure as "Belt Press Raw Juice"). The first solid phase is conveyed to a screw press to generate a second juice (identified in the Figure as "Screw Pres Raw Juice") and a wet bio-crude. The first solid phase remaining in the belt press is flushed using water (identified in the Figure as "Belt Filter Wash Water"). The washed belt filter solids obtained thereby are fed to the screw press for further pressing. The wet bio-crude ejected from the screw press is collected for drying using a biocrude dryer (a spin flash dryer) to generate a dry bio-crude. The belt press raw juice and the screw press raw juice are combined to form a combined raw juice and fed to a vibratory separator in which the combined raw juice is filtered to generate a mash comprising recycled solids and filtered juice. The mash is fed to a screw press for further pressing. The filtered juice is stored in juice tank 1. Juice tank 1 is a storage tank, preferably chilled. Filtered juice from juice tank 1 is clarified using a centrifuge to generate centrifuged solids from the filtered juice and a spun filtered juice (also referred to as a "clarified juice"). The centrifuged solids from the filtered juice are fed to a screw press for further pressing. The centrifuged solids from the filtered juice are used as a wet bio-crude. The spun filtered juice is stored in juice tank 2, and the pH thereof is adjusted to below 5 and left to sit overnight. The temperature is maintained at below 35° C. The spun filtered juice is processed in a precipitator to cause heat-induced protein coagulation, generating a broth comprising a wet protein concentrate. The broth is centrifuged to generate a liquor and a wet protein concentrate. The liquor is recycled back to the growth ponds (also referred to as bioreactors). In other embodiments, the liquor is discarded. The wet protein concentrate ("WPC") is washed three times after being diluted by adding water to the wet protein concentrate to form a wet protein concentrate wash. The ratio of wet protein concentrate to water is 1:1 to 1:10 by weight. The resulting wet protein concentrate wash is dried using a protein dryer (spray dryer) to generate a dry protein concentrate.

In FIG. 29, each solid arrow indicates the process stream, each dotted arrow indicates a recycled mass stream, while each letter or letter/number combination within a hexagon indicates a sampling location or a material ID. The notations "pH adjusted to <5 and left to sit overnight," "Temperature maintained at <35° C.," and "WPC (I1) washed 3 times with (1:1 to 1:10 WPC:H2O) and re-centrifuged" are revisions made to the process.

Example 14

Process Flow Diagram

Figure 30:
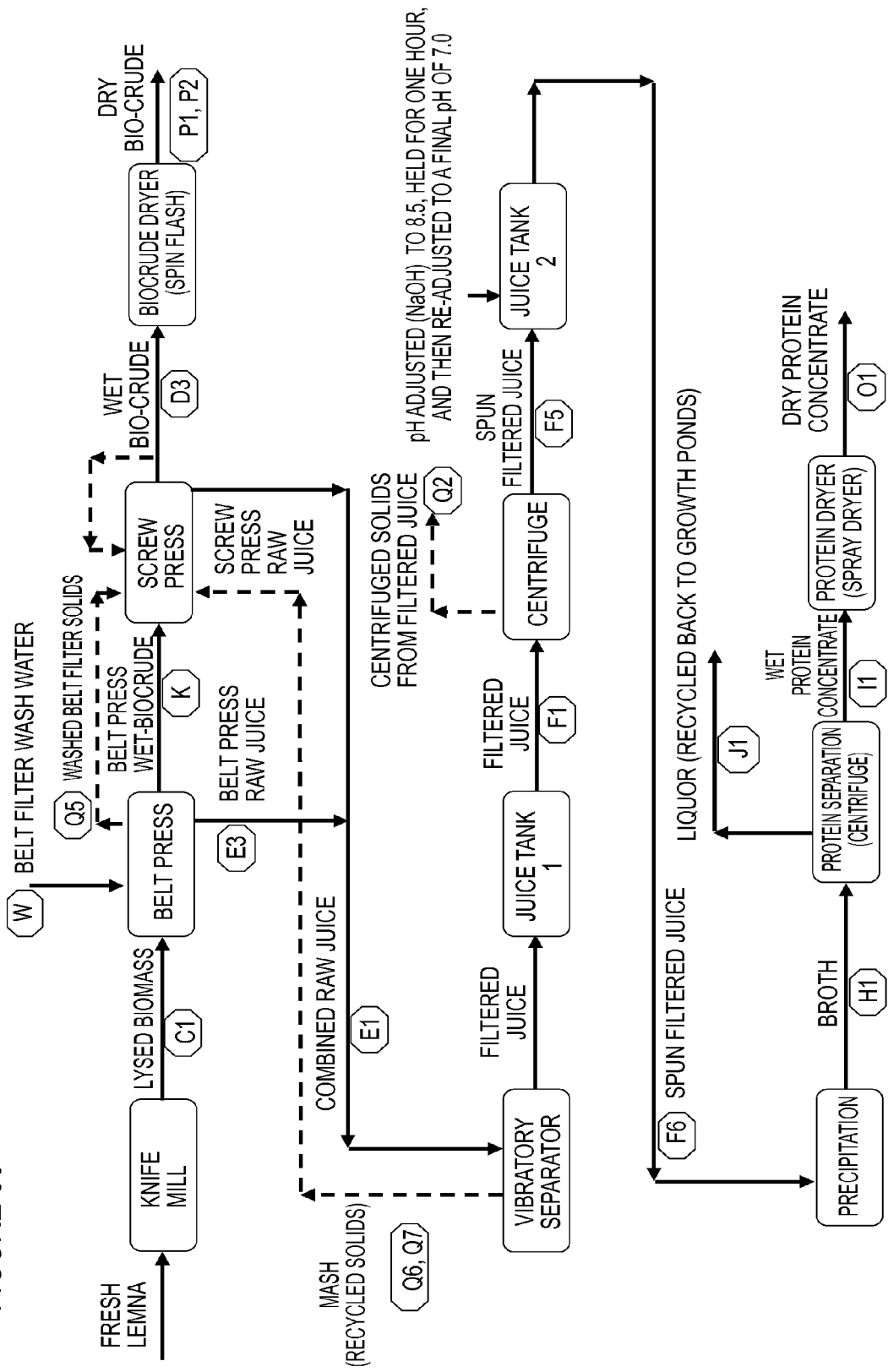
FIG. 30 is a flow diagram illustrating an exemplary process of isolating protein from fresh lemna.

FIG. 30 shows a flow diagram of an exemplary process of isolating protein from an aquatic species, e.g., fresh lemna. The process was tested by experiments.

Fresh lemna (also referred to as biomass slurry or raw feedstock) are conveyed to a knife mill where the wet biomass fronds are lysed to expose the internal water and protein. The lysed biomass is conveyed to a belt press in which the lysed biomass is pressed to generate a first solid phase (identified in the Figure as "Belt Press Wet Bio-Crude") and a juice (identified in the Figure as "Belt Press Raw Juice"). The first solid phase is conveyed to a screw press for further pressing to generate a second juice (identified in the Figure as "Screw Pres Raw Juice") and a wet bio-crude. The first solid phase remaining in the belt press is flushed using water (identified in the Figure as "Belt Filter Wash Water"). The washed belt filter solids obtained thereby are fed to the screw press for further pressing. The wet bio-crude ejected from the screw press is collected for drying using a biocrude dryer (a spin flash dryer) to generate a dry bio-crude. The belt press raw juice and the screw press raw juice are combined to form a combined raw juice and fed to a vibratory separator in which the combined raw juice is filtered to generate a mash comprising recycled solids) and filtered juice. The mash is fed to a screw press for further pressing. The filtered juice is stored in juice tank 1. Filtered juice from juice tank 1 is clarified using a centrifuge to generate centrifuged solids from the filtered juice and a spun filtered juice (also referred to as a "clarified juice"). The centrifuged solids from the filtered juice are fed to a screw press for further pressing. The centrifuged solids from the filtered juice are used as a wet bio-crude. The spun filtered juice is stored in juice tank 2, and the pH thereof is adjusted to 8.5, held at pH of 8.5 for one hour, then re-adjusted to a final pH of 7.0. The spun filtered juice is then processed in a precipitator to cause heat-induced protein coagulation, generating a broth comprising a wet protein concentrate. In other embodiments, the protein in the spun filtered juice is coagulated by acid treatment, a combination of acid and thermal treatment. In order to separate the protein from the remaining part of the broth, the broth is centrifuged to generate a liquor and a wet protein concentrate. The liquor is recycled back to the growth ponds (also referred to as bioreactors). In other embodiments, the liquor is discarded. The wet protein concentrate is washed or diluted by adding water to the wet protein concentrate to form a wet protein concentrate wash. The resulting wet protein concentrate wash is dried using a protein dryer (spray dryer) to generate a dry protein concentrate. The dry protein concentrate is packaged for further use or analysis.

In FIG. 30, each solid arrow indicates the process stream, each dashed arrow indicates a recycled mass stream, and each letter or letter/number combination within a hexagon indicates a sampling location or a material ID. The notation "pH Adjustment (NaOH) to 8.5, held for one hour, and then re-adjusted to a final pH of 7.0" indicates a revision to the process.

Example 15

Process Flow Diagram

Figure 31:
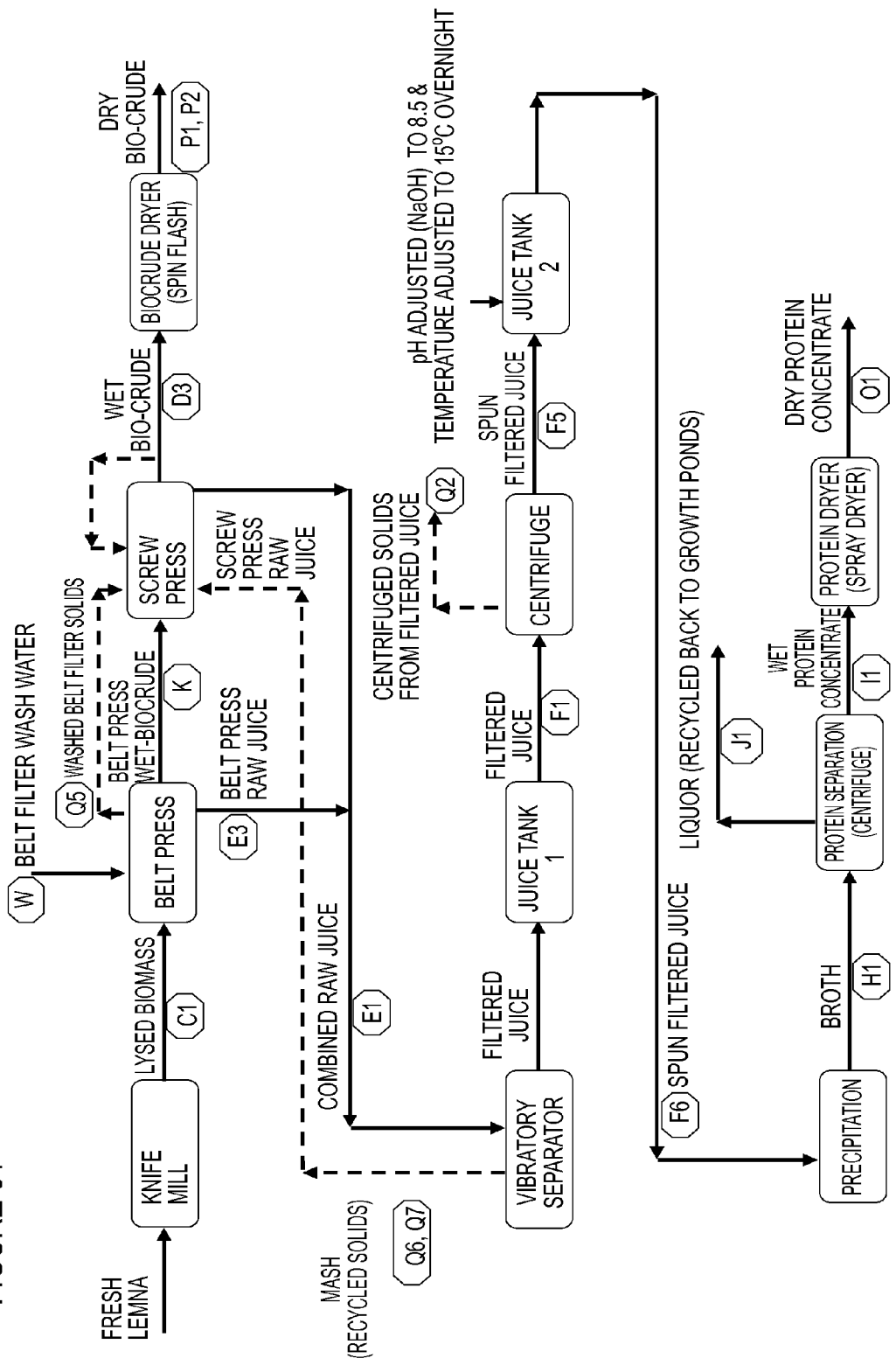
FIG. 31 is a flow diagram illustrating an exemplary process of isolating protein from fresh lemna.

FIG. 31 shows a flow diagram of an exemplary process of isolating protein from an aquatic species, e.g., fresh lemna. The process was tested by experiments.

Fresh lemna (also referred to as biomass slurry or raw feedstock) are conveyed to a knife mill where the wet biomass fronds are lysed to expose the internal water and protein. The lysed biomass is conveyed to a belt press in which the lysed biomass is pressed to generate a first solid phase (identified in the Figure as "Belt Press Wet Bio-Crude") and a juice (identified in the Figure as "Belt Press Raw Juice"). The first solid phase is conveyed to a screw press for further pressing to generate a second juice (identified in the Figure as "Screw Press Raw Juice") and a wet bio-crude. The first solid phase remaining in the belt press is flushed using water (identified in the Figure as "Belt Filter Wash Water"). The washed belt filter solids obtained thereby are fed to the screw press for further pressing. Some of the wet bio-crude ejected from the screw press is recycled back into the screw press. The wet bio-crude ejected from the screw press is collected for drying using a biocrude dryer (a spin flash dryer) to generate a dry bio-crude. The belt press raw juice and the screw press raw juice are combined to form a combined raw juice and fed to a vibratory separator in which the combined raw juice is filtered to generate a mash comprising recycled solids) and filtered juice. The mash is fed to a screw press for further pressing. The filtered juice is stored in juice tank 1. Juice Tank 1 is a chilled storage tank. Filtered juice from juice tank 1 is clarified using a centrifuge to generate centrifuged solids from the filtered juice and a spun filtered juice (also referred to as a "clarified juice"). The centrifuged solids from the filtered juice are fed to a screw press for further pressing. The centrifuged solids from the filtered juice are used as a wet bio-crude. The spun filtered juice is stored in juice tank 2, and the pH thereof is adjusted to 8.5, and the temperature is adjusted to 15° C. overnight. The spun filtered juice is then processed in a precipitator to cause heat-induced protein coagulation, generating a broth comprising a wet protein concentrate. In other embodiments, the protein in the spun filtered juice is coagulated by acid treatment, a combination of acid and thermal treatment. In order to separate the protein from the remaining part of the broth, the broth is centrifuged to generate a liquor and a wet protein concentrate. The liquor is recycled back to the growth ponds (also referred to as bioreactors). In other embodiments, the liquor is discarded. The wet protein concentrate is washed or diluted by adding water to the wet protein concentrate to form a wet protein concentrate wash. The ratio of wet protein concentrate to water is 4:1 by weight. The resulting wet protein concentrate wash is dried using a protein dryer (spray dryer) to generate a dry protein concentrate. The dry protein concentrate is packaged for further use or analysis.

The lemna, belt filter wash water, wet bio-crude, dry bio-crude, pH adjustment and temperature adjustment, wet protein concentrate, and dry protein concentrate are measured values. The lysed biomass, belt press wet-biocrude, belt press raw juice, screw press raw juice, combined raw juice, and broth are calculated values. The filtered juice, spun filtered juice, and liquor are material for which volume is taken and mass is calculated based on density. The washed belt filter solids and mash (recycled solids) are recycled material. The centrifuged solids from filtered juice are weighed and discarded material.

In FIG. 31, each black arrow indicates a process stream; each dashed arrow indicates recycled material; each dotted arrow indicates material weighed and discarded; each letter or letter/number combination within a hexagon indicates a sampling location or a material ID the Fresh *Lemna*, Belt Filter Wash Water, Wet Bio-Crude, Dry Bio-Crude, Wet Protein Concentrate, and Dry Protein Concentrate are measured values; the Lysed Biomass, Belt Press Wet-Biocrude, Belt Press Raw Juice, Screw Press Raw Juice, Combined Raw Juice, and Broth indicate calculated values; Filtered Juice, Spun Filtered Juice, Liquor (Recycled back to Growth Ponds) indicate mass values calculated from measured volume and known density; Washed Belt Filter Solids and Mash (Recycled Solids) indicate recycled material; and Centrifuged Solids from Filtered Juice indicates material weighed and discarded.

Example 16

Process Flow Diagrams

Figure 32:
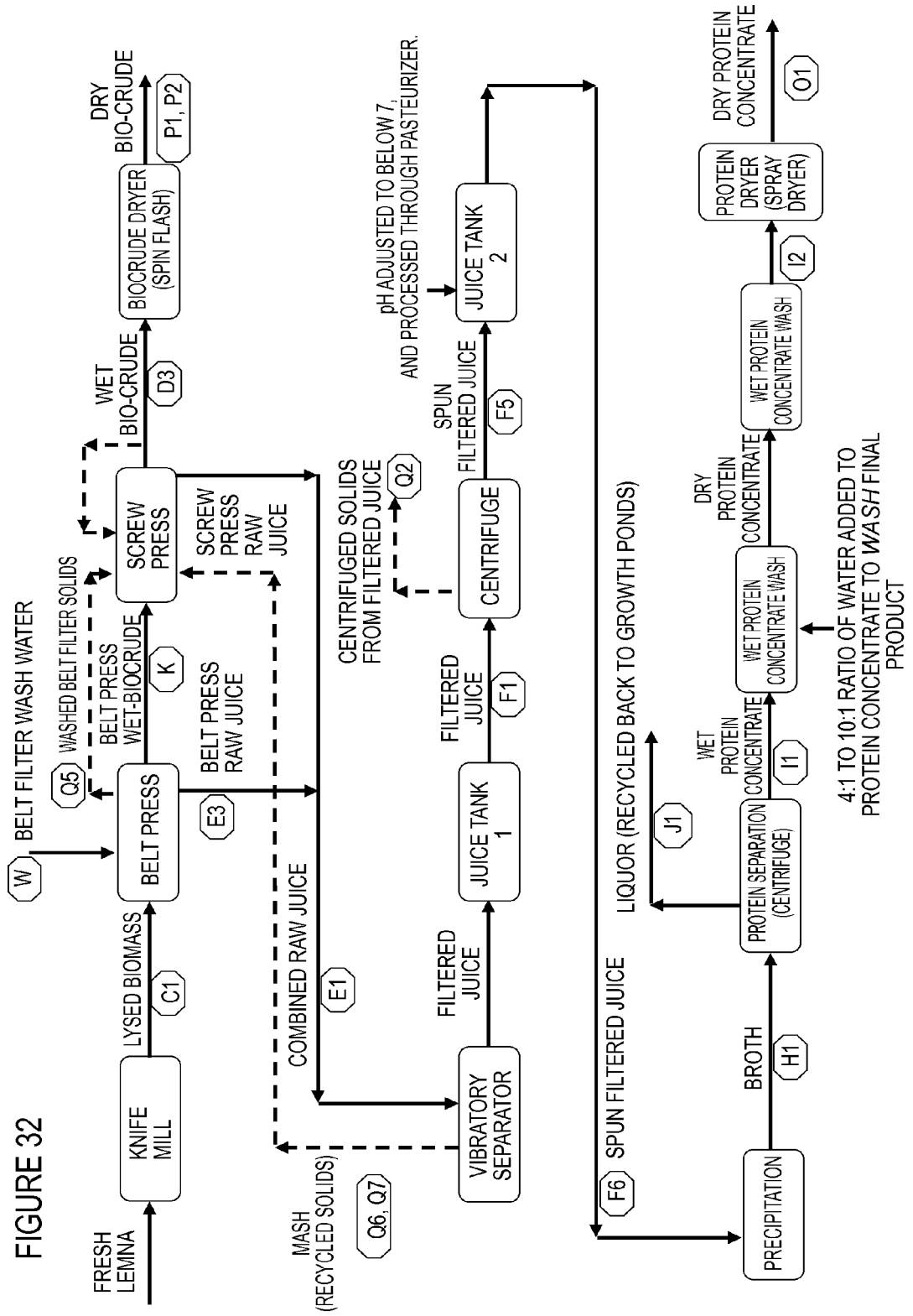
FIG. 32 is a flow diagram illustrating an exemplary process of isolating protein from fresh lemna with optional pH adjustment and wet protein wash.

FIG. 32 shows a flow diagram of an exemplary process of isolating protein from an aquatic species, e.g., fresh lemna, with optional pH adjustment and wet protein wash. The process was tested by experiments.

Fresh lemna (also referred to as biomass slurry or raw feedstock) are conveyed to a knife mill where the wet biomass fronds are lysed to expose the internal water and protein. The lysed biomass is conveyed to a belt press in which the lysed biomass is pressed to generate a first solid phase (identified in the Figure as "Belt Press Wet Bio-Crude") and a juice (identified in the Figure as "Belt Press Raw Juice"). The first solid phase is conveyed to a screw press for further pressing to generate a second juice (identified in the Figure as "Screw Press Raw Juice") and a wet bio-crude. The first solid phase remaining in the belt press is flushed using water (identified in the Figure as "Belt Filter Wash Water"). The washed belt filter solids obtained thereby are fed to the screw press for further pressing. Some of the wet bio-crude ejected from the screw press is recycled back into the screw press. The wet bio-crude ejected from the screw press is collected for drying using a biocrude dryer (a spin flash dryer) to generate a dry bio-crude. The belt press raw juice and the screw press raw juice are combined to form a combined raw juice and fed to a vibratory separator in which the combined raw juice is filtered to generate a mash comprising recycled solids and filtered juice. The mash is fed to a screw press for further pressing. The filtered juice is stored in juice tank 1. Juice Tank 1 is a chilled storage tank. Filtered juice from juice tank 1 is clarified using a centrifuge to generate centrifuged solids from the filtered juice and a spun filtered juice (also referred to as a "clarified juice"). The centrifuged solids from the filtered juice are taken for sampling. The centrifuged solids from the filtered juice are used as a wet bio-crude. The spun filtered juice is stored in juice tank 2, and the pH thereof is adjusted to below 7. The spun filtered juice is then processed in a precipitator to cause heat-induced protein coagulation, generating a broth comprising a wet protein concentrate. In other embodiments, the protein in the spun filtered juice is coagulated by acid treatment, a combination of acid and thermal treatment. In order to separate the protein from the remaining part of the broth, the broth is centrifuged to generate a liquor and a wet protein concentrate. The liquor is recycled back to the growth ponds (also referred to as bioreactors). In other embodiments, the liquor is discarded. The wet protein concentrate is washed by adding water to the wet protein concentrate to form a wet protein concentrate wash and wash out impurities in the final product. The ratio of wet protein concentrate to water is 4:1 to 10:1 by weight. The resulting wet protein concentrate wash is dried using a protein dryer (spray dryer) to generate a dry protein concentrate. The dry protein concentrate is packaged for further use or analysis.

In FIG. 32, each black arrow indicates a process stream; each dashed arrow indicates recycled material; the notation "pH Adjustment to below 7, and processed through "precipitator," "Single Day Runs," "Broth," "Wet Protein Concentrate Wash," "I2," and "4:1 ratio of Water added to Protein Concentrate to Wash Final Product" are revisions made to the process; "Day 1 Sampling," "Day 2 Sampling," and "Temperature adjusted to 15° C. Overnight" are parameters removed from the process; and each letter or letter/number combination within a hexagon indicates a sampling location or a material ID.

Example 17

Process Flow Diagram

Figure 33:
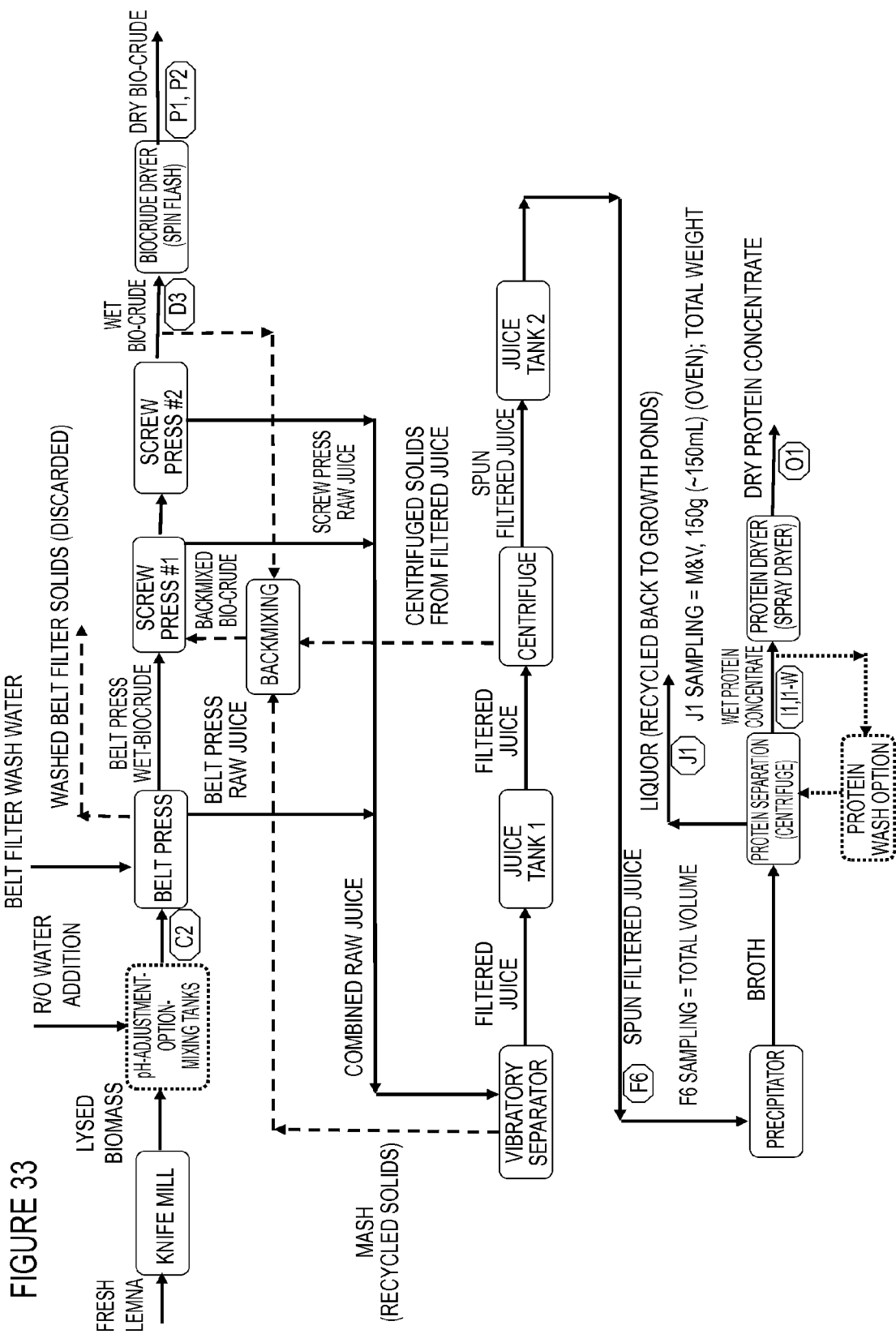
FIG. 33 is a flow diagram illustrating an exemplary process of isolating protein from fresh lemna with backmixing and optional protein wash as well as producing other products (e.g., bio-crude).

FIG. 33 shows a flow diagram of an exemplary process of isolating protein from an aquatic species, e.g., fresh lemna, with backmixing and optional protein wash. The process was tested by experiments.

Fresh lemna (also referred to as biomass slurry or raw feedstock) are conveyed to a knife mill where the wet biomass fronds are lysed to expose the internal water and protein. The lysed biomass is conveyed to mixing tanks to which R/O water is added. The ratio of water to biomass is 1:1. The lysed biomass is conveyed to a belt press in which the lysed biomass is pressed to generate a first solid phase (identified in the Figure as "Belt Press Wet Bio-Crude"), a juice (identified in the Figure as "Belt Press Raw Juice"), and skimmed-out solids (identified in the Figure as "Belt Press Filter Solids"). The first solid phase is conveyed to screw press #1 to generate a second juice (identified in the Figure as "Screw Press Raw Juice") and a wet bio-crude. The biocrude is conveyed to screw press #2 for further pressing to generate a juice (identified in the Figure as "Screw Press Raw Juice") and a wet bio-crude. The first solid phase remaining in the belt press is flushed using water (identified in the Figure as "Belt Filter Wash Water"). The washed belt filter solids obtained thereby are discarded. Some of the wet bio-crude ejected from screw press #1 and screw press #2 is fed to the backmixing container. The wet bio-crude ejected from screw press #2 is collected for drying using a biocrude dryer (a spin flash dryer) to generate a dry bio-crude. The belt press raw juice and the screw press raw juice from screw press #1 and screw press #2 are combined to form a combined raw juice and fed to a vibratory separator in which the combined raw juice is filtered to generate a mash comprising recycled solids and filtered juice. The mash is fed to the backmixing container. The filtered juice is stored in juice tank 1. Juice tank 1 is a chilled storage tank. Filtered juice from juice tank 1 is clarified using a centrifuge to generate centrifuged solids from the filtered juice and a spun filtered juice (also referred to as a "clarified juice"). The centrifuged solids from the filtered juice are fed to the backmixing container. The spun filtered juice is stored in juice tank 2. The spun filtered juice is then processed in a precipitator to cause heat-induced protein coagulation, generating a broth comprising a wet protein concentrate. In other embodiments, the protein in the spun filtered juice is coagulated by acid treatment, a combination of acid and thermal treatment. In order to separate the protein from the remaining part of the broth, the broth is centrifuged to generate a liquor and a wet protein concentrate. The liquor is recycled back to the growth ponds (also referred to as bioreactors). In other embodiments, the liquor is discarded. The wet protein concentrate is optionally washed or diluted by adding water to the wet protein concentrate to form a wet protein concentrate wash. The ratio of wet protein concentrate to water is 4:1 by weight. The resulting wet protein concentrate wash is dried using a protein dryer (spray dryer) to generate a dry protein concentrate. The dry protein concentrate is packaged for further use or analysis.

In FIG. 33, each black arrow indicates a process stream, each dotted line and arrow indicates optional process steps, each dashed arrow indicates recycled material, and each letter or letter/number combination within a hexagon indicates a sampling location or a material ID.

Example 18

Process Flow Diagram

Figure 34:
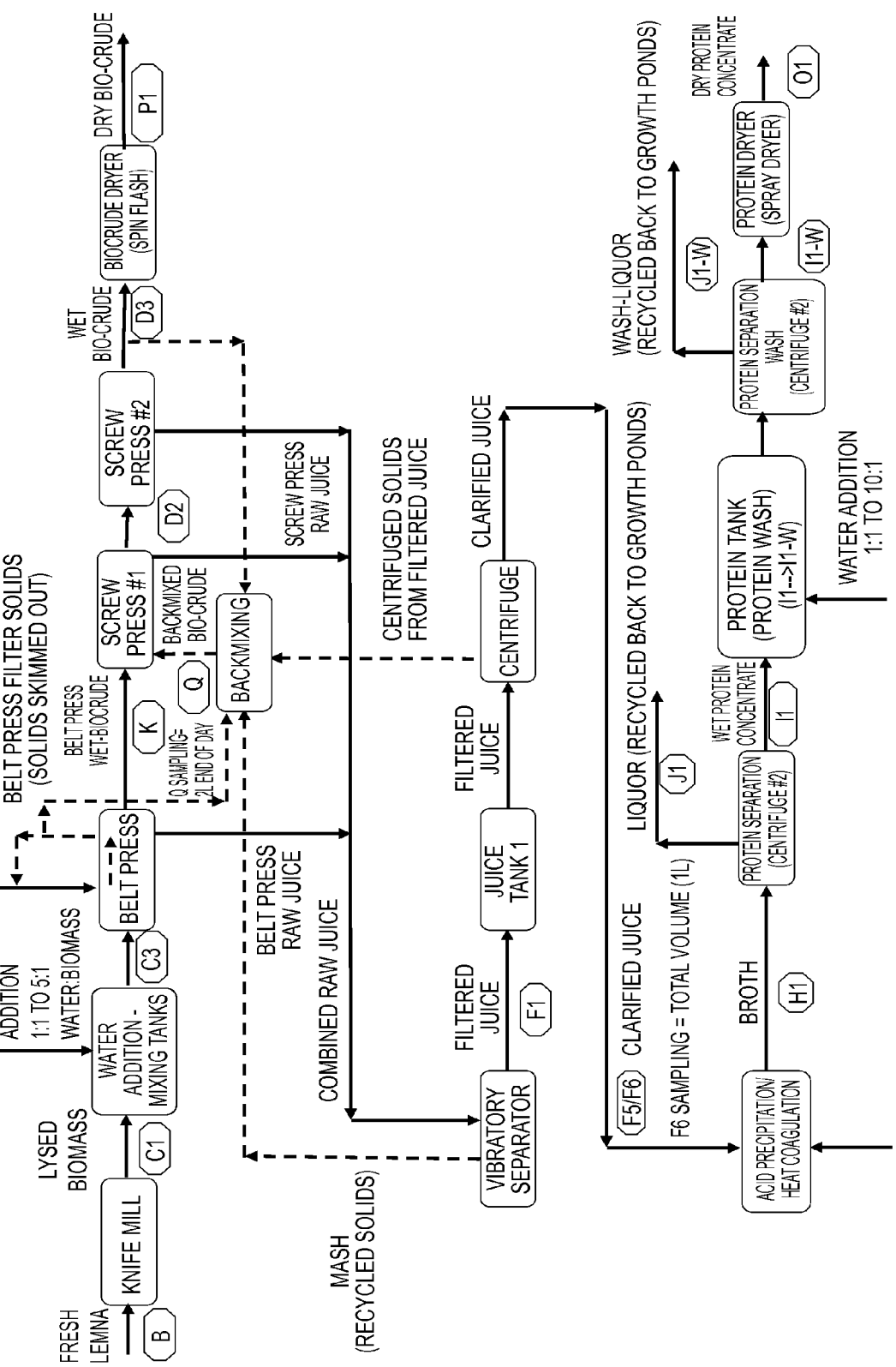
FIG. 34 is a flow diagram illustrating an exemplary process of isolating protein from fresh lemna with backmixing and water addition to mixing tanks.

FIG. 34 shows a flow diagram of an exemplary process of isolating protein from an aquatic species, e.g., fresh lemna, with backmixing and water addition to mixing tanks. The process was tested by experiments.

Fresh lemna (also referred to as biomass slurry or raw feedstock) are conveyed to a knife mill where the wet biomass fronds are lysed to expose the internal water and protein. The lysed biomass is conveyed to mixing tanks to which R/O water is added. The ratio of water to biomass is 1:1 to 5:1. The lysed biomass is conveyed to a belt press in which the lysed biomass is pressed to generate a first solid phase (identified in the Figure as "Belt Press Wet Bio-Crude"), a juice (identified in the Figure as "Belt Press Raw Juice"), and skimmed-out solids (identified in the Figure as "Belt Press Filter Solids"). The first solid phase is conveyed to screw press #1 and screw press #2 for further pressing to generate a second juice (identified in the Figure as "Screw Press Raw Juice") and a wet bio-crude. The first solid phase remaining in the belt press is flushed using water (identified in the Figure as "Belt Filter Wash Water"). The washed belt filter solids obtained thereby are fed to the backmixing container. Some of the wet bio-crude ejected from the screw press is fed to the backmixing container. The wet bio-crude ejected from screw press #2 is collected for drying using a biocrude dryer (a spin flash dryer) to generate a dry bio-crude. The belt press raw juice and the screw press raw juice from screw press #1 and screw press #2 are combined to form a combined raw juice and fed to a vibratory separator in which the combined raw juice is filtered to generate a mash comprising recycled solids and filtered juice. The mash is fed to the backmixing container. The filtered juice is stored in juice tank 1. Juice tank 1 is a chilled storage tank. Filtered juice from juice tank 1 is clarified using a centrifuge to generate centrifuged solids from the filtered juice and a spun filtered juice (also referred to as a "clarified juice"). The centrifuged solids from the filtered juice are fed to the backmixing container. The protein in the spun filtered juice is coagulated by acid treatment, a combination of acid addition and/or heat coagulation. In order to separate the protein from the remaining part of the broth, the broth is centrifuged to generate a liquor and a wet protein concentrate. The liquor is recycled back to the growth ponds (also referred to as bioreactors). In other embodiments, the liquor is discarded. The wet protein concentrate is washed or diluted by adding water (1:1 to 10:1) to the wet protein concentrate to form a wet protein concentrate wash. The resulting wet protein concentrate wash is dried using a protein dryer (spray dryer) to generate a dry protein concentrate. The dry protein concentrate is packaged for further use or analysis.

In FIG. 34, each black arrow indicates a process stream, each dashed arrow indicates recycled material, and each letter or letter/number combination within a hexagon indicates a sampling location or a material ID.

Example 19

Process Flow Diagram

Figure 35:
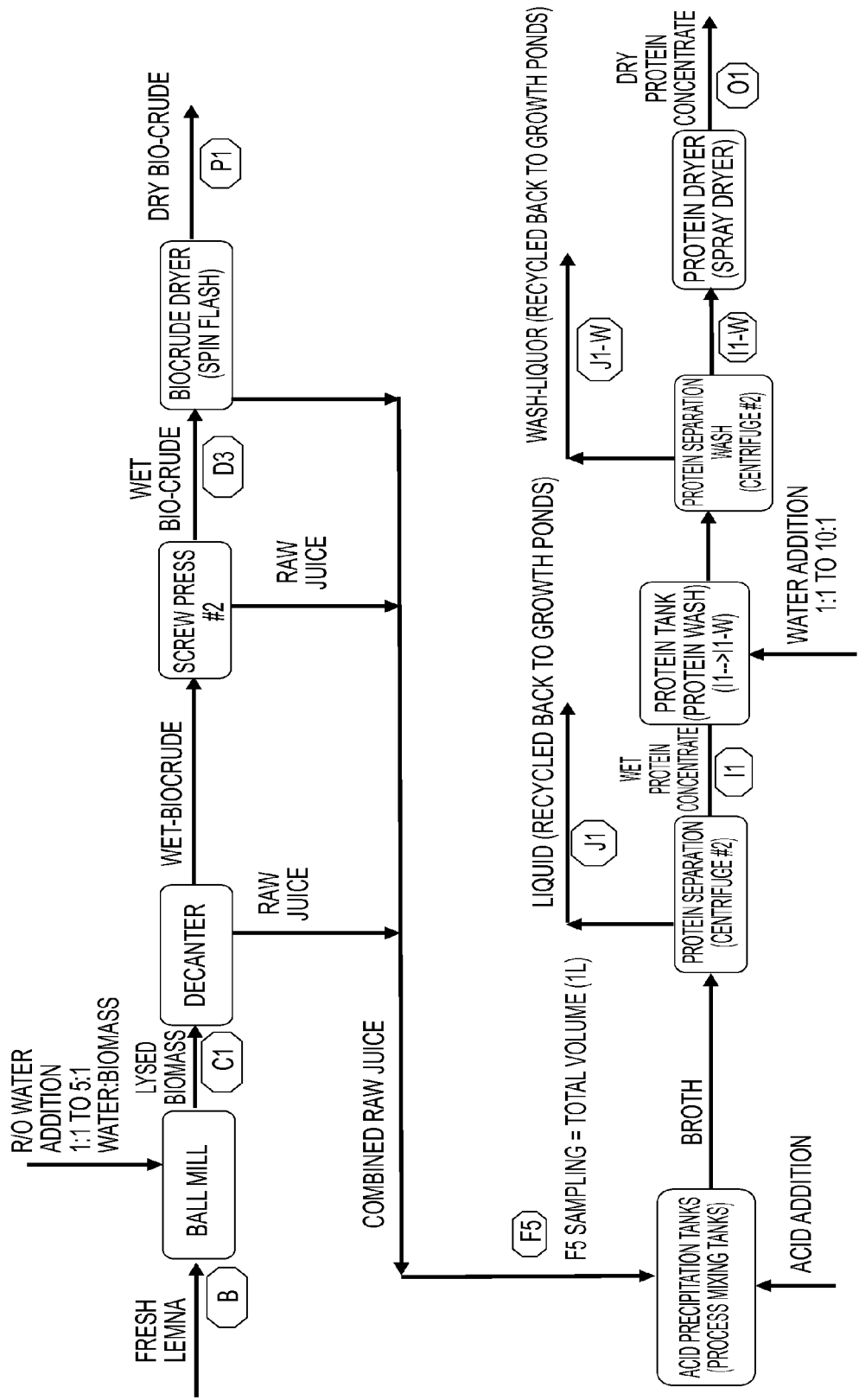
FIG. 35 is a flow diagram illustrating an exemplary process of isolating protein and other products from fresh lemna with ball mill and decanter.

FIG. 35 shows a flow diagram of an exemplary process of isolating protein from an aquatic species, e.g., fresh lemna, with a ball mill and decanter. The process was tested by experiments.

Fresh lemna (also referred to as biomass slurry or raw feedstock) are conveyed to a ball mill to which R/O water is added where the wet biomass fronds are lysed to expose the internal water and protein. The ratio of water to biomass is 1:1 to 5:1. The lysed biomass is conveyed to a decanter in which the lysed biomass is pressed to generate a first solid phase (identified in the Figure as "Wet Bio-Crude") and a juice (identified in the Figure as "Raw Juice"). The first solid phase is conveyed to screw press #2 for further pressing to generate a second juice (identified in the Figure as "Raw Juice") and a wet bio-crude. The wet bio-crude ejected from screw press #2 is collected for drying using a biocrude dryer (a spin flash dryer) to generate a dry bio-crude. The raw juice from screw press #1 and raw juice from screw press #2 are combined to form a combined raw juice and fed to acid preparation tanks (process mixing tanks) in which the protein in the spun filtered juice is coagulated by $H_2SO_4$ acid addition. In order to separate the protein from the remaining part of the broth, the broth is centrifuged in centrifuge #1 to generate a liquor and a wet protein concentrate. The liquor is recycled back to the growth ponds (also referred to as bioreactors). In other embodiments, the liquor is discarded. The wet protein concentrate is washed by adding a known amount of water (1:1 to 10:1) to the wet protein concentrate to form a wet protein concentrate wash. The protein is separated in centrifuge #2 to generate a wash-liquor, which is recycled back to the growth ponds (also referred to as bioreactors). In other embodiments, the wash liquor is discarded. The resulting wet protein concentrate wash is dried using a protein dryer (spray dryer) to generate a dry protein concentrate. The dry protein concentrate is packaged for further use or analysis.

In FIG. 35, each black arrow indicates a process stream, each dashed arrow indicates recycled material, and each letter or letter/number combination within a hexagon indicates a sampling location or a material ID.

Example 20

Process Flow Diagram of Pilot Commercial Unit to Grow and Harvest *Lemna*

Figure 36:
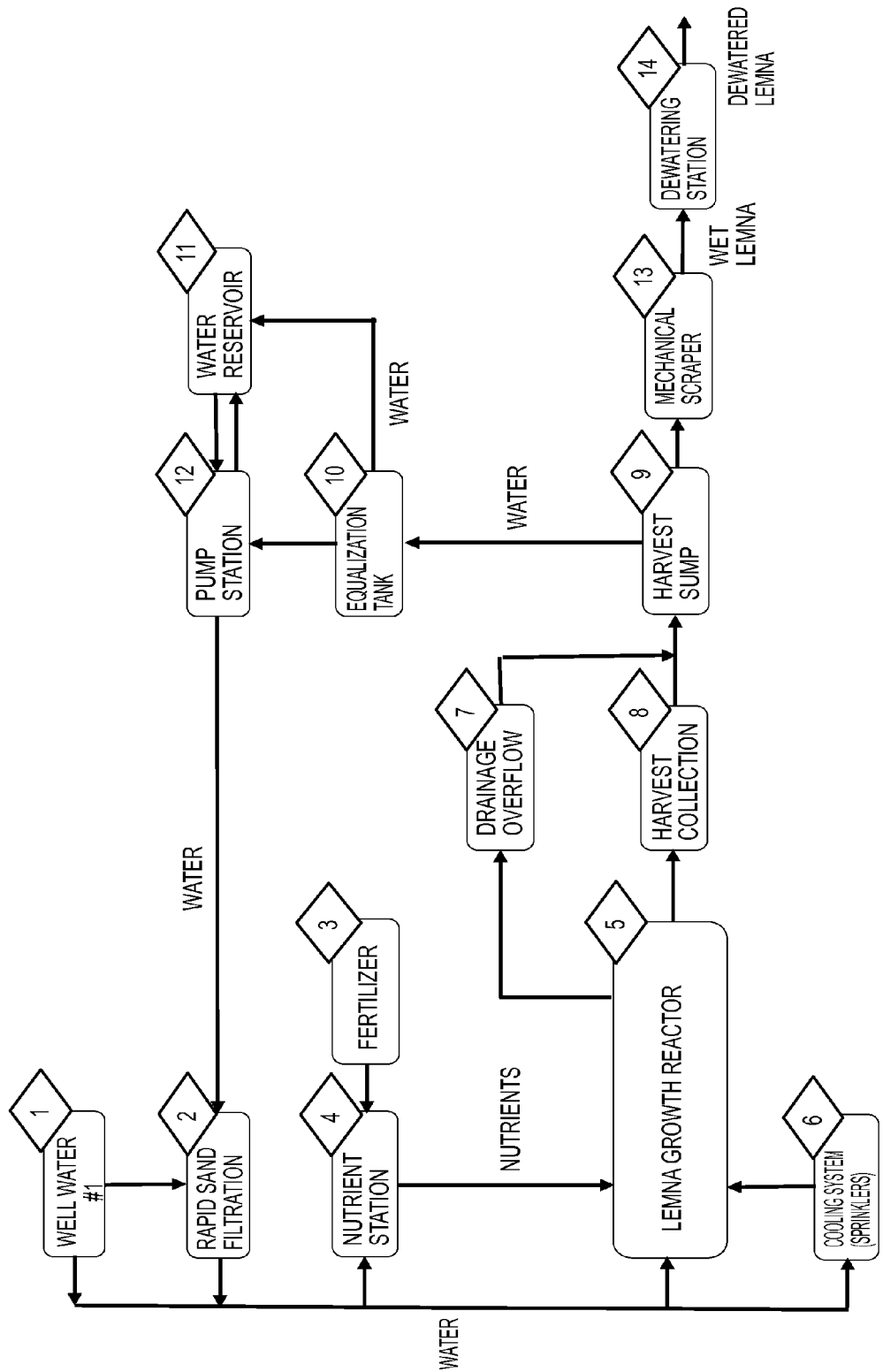
FIG. 36 is a flow diagram illustrating an exemplary process of growing and harvesting fresh lemna.

FIG. 36 shows a flow diagram of an exemplary process of growing and harvesting an aquatic species, e.g., fresh lemna. The process was tested by experiments.

The bioreactors, also referred to as "growth reactors" are filled with well water that meets appropriate specifications for acceptable water quality and then the properly balanced nutrition. Smaller ponds are designed and sized to adequately serve as "feeder" ponds to the larger bioreactors. The smaller ponds are first inoculated and grown to high density at which point they can optimally seed the larger ponds in a manner that supports the most rapid growth. Fertilizer is fed to the nutrient station, and the nutrients are fed to the lemna growth reactor.

Well water is conveyed to rapid sand filtration with water from the pump station that pumps water to and from the water reservoir. Some of the water from the rapid sand filtration and well water is added to the nutrient station. Some of the water from the rapid sand filtration and well water is added to the lemna growth reactor to maintain the reactor level at a certain set-point. Some of the water from the rapid sand filtration and well water is added to the sprinklers, which acts as a cooling system to the lemna growth reactor. For optimum micro-crop productivity, the water is closely monitored to maintain the necessary nutrients and water elements within standard levels. Sensors installed in the ponds monitor and record the levels of ammonia, pH, oxidation reduction potential (ORP), and temperature. The ammonia sensor is used as feedback to control the levels of nitrogen in the ponds via the nutrient tank injection system. A liquid level transmitter installed in each pond assures that the water level does not fall below the desired depth.

For maximum biomass productivity, the thickness of the micro-crop mat is monitored and maintained at a desired thickness. Harvesting can take place through several physical mechanisms and at varying times throughout the year, based on environmental conditions and the corresponding growth of the specific species. When the desired harvesting conditions are met, the micro-crop mat is transported over the skimmers and pumped to a vibrating screen where the micro-crop is separated and collected in a hopper for further processing. The harvest process is controlled via a programmable logic controller (PLC) and human/machine interface (HMI).

The drainage overflow from the lemna growth reactor and the outflow from the harvest collection are conveyed to the harvest sump. The water from the harvest sump is fed to the equalization tank, from which water is fed to the pump station and the water reservoir.

The material from the harvest sump is conveyed to the mechanical scraper. The wet lemna is conveyed to the dewatering station to yield dewatered lemna for further processing.

In FIG. 36, each black text indicates process streams; "Well Water #1," "Rapid Sand Filtration," "Pump Station," "Water Reservoir," and "Equalization Tank," indicate water supply; "Nutrient Station" and "Fertilizer" indicate nutrients; "Harvest Sump," "Mechanical Scraper," and "Dewatering Station" indicate harvest dewatering; and each number within a rhombus indicates unit operation.

Example 21

Process Flow Diagram of Pilot Commercial Unit to Isolate Protein from *Lemna*

Figure 37:
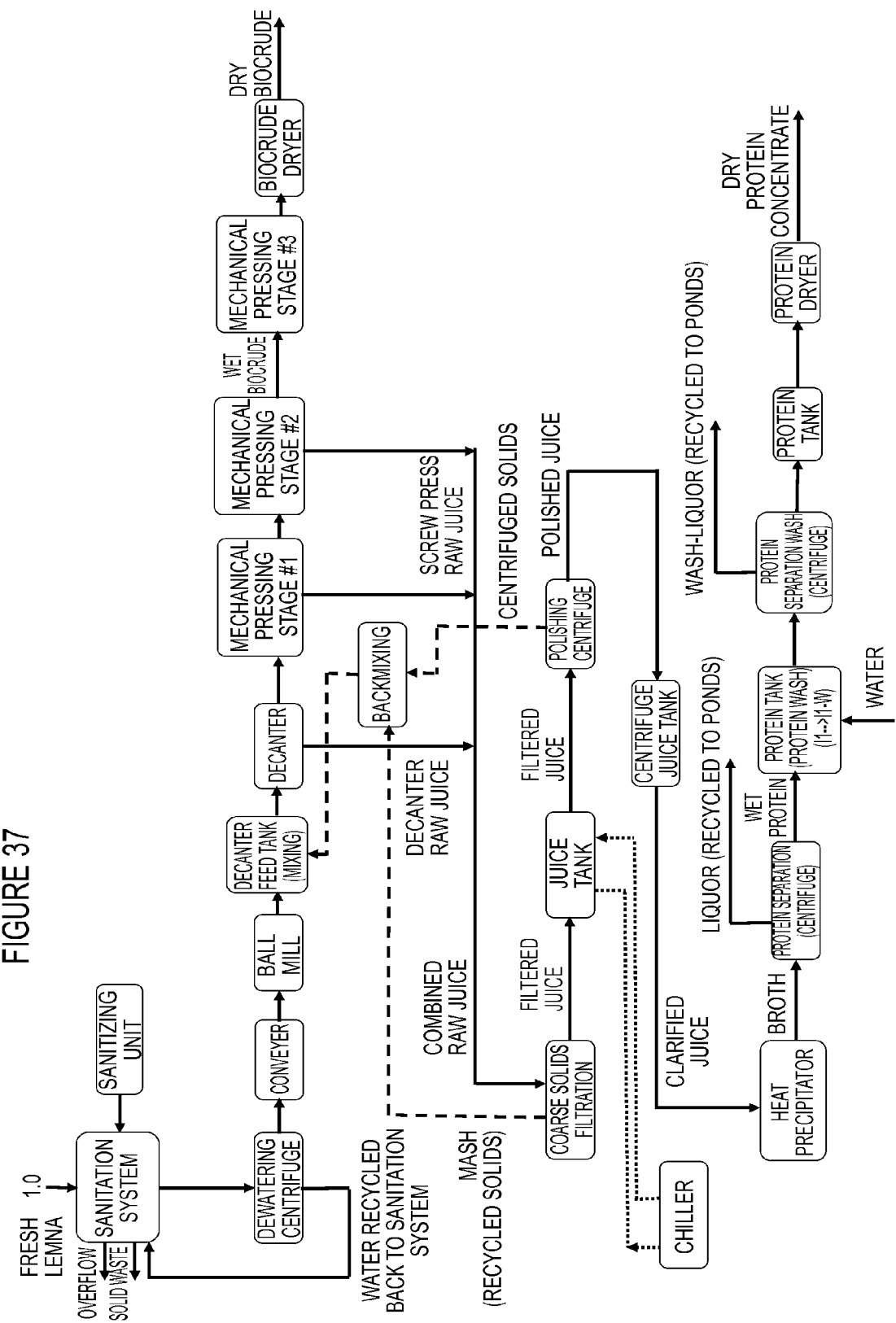
FIG. 37 is a flow diagram illustrating an exemplary process of isolating protein and other products from fresh lemna.

FIG. 37 shows a flow diagram of an exemplary process of isolating protein from an aquatic species, e.g., fresh lemna. The process was tested by experiments.

Fresh lemna (also referred to as biomass slurry or raw feedstock) are conveyed to a sanitation system from which overflow and solid waste are discarded. The material is conveyed to a dewatering centrifuge or shaker screen conveyor system and the separated water is recycled back to the sanitation system. The material is fed to a conveyor and then to a ball mill where the wet biomass fronds are lysed to expose the internal water and protein. The lysed biomass is conveyed to a decanter feed tank for the mixing step. The lysed biomass is conveyed to a decanter which generates a decanter raw juice. The solid phase is conveyed to a mechanical pressing stage #1 to generate a second juice (identified in the Figure as "Raw Juice") and a biocrude. The biocrude is conveyed to mechanical pressing stage #2 for further pressing to generate a juice (identified in the Figure as "Screw Press Raw Juice") and a wet biocrude. The wet biocrude is conveyed to a mechanical pressing stage #3. The wet biocrude ejected from screw press #3 is collected for drying using a biocrude dryer (a spin flash dryer) to generate a dry biocrude.

The decanter raw juice and the screw press raw juice from mechanical pressing stage #1 and mechanical pressing stage #2 are combined to form a combined raw juice and fed to a coarse solids filtration container in which the combined raw juice is filtered to generate a mash comprising recycled solids and filtered juice. The mash is fed to the backmixing container. The filtered juice is stored in the juice tank. The juice tank is connected to a chiller. Filtered juice from the juice tank is clarified using a polishing centrifuge to generate centrifuged solids from the filtered juice and a clarified juice. The centrifuged solids from the filtered juice are fed to the backmixing container. The clarified juice is conveyed to a heat precipitator to cause heat-induced protein coagulation, generating a broth comprising a wet protein concentrate. In other embodiments, the protein in the spun filtered juice is coagulated by acid treatment, a combination of acid and/or thermal treatment. In order to separate the protein from the remaining part of the broth, the broth is centrifuged to generate a liquor and a wet protein concentrate. The liquor is recycled back to the growth ponds (also referred to as bioreactors). In other embodiments, the liquor is discarded. The wet protein concentrate is washed in the protein tank by adding water to the wet protein concentrate to form a wet protein concentrate wash. The protein is separated in a centrifuge to generate a wash-liquor, which is recycled back to the growth ponds (also referred to as bioreactors). In other embodiments, the wash liquor is discarded. The resulting wet protein concentrate wash is dried using a protein dryer (spray dryer) to generate a dry protein concentrate.

In FIG. 37, each black arrow indicates a process stream; each dashed arrow indicates recycled stream; each dotted arrow indicates utilities; "Sanitation System," "Dewatering Centrifuge," and "Conveyor" indicate sanitation system; "Ball Mill," "Decanter Feed Tank (Mixing)," "Decanter," "Mechanical Pressing Stage #1," "Mechanical Pressing Stage #2," "Mechanical Pressing Stage #3," "Biocrude Dryer," and "Backmixing" indicate biocrude processing; and "Coarse Solids Filtration," "Juice Tank," "Polishing Centrifuge," "Chiller," "Centrifuge Juice Tank," "Heat Precipitator," "Protein Separation (Centrifuge)," "Protein Tank (Protein Wash),"

"Protein Separation Wash (Centrifuge)," "Protein Tank," and "Protein Dryer" indicate protein processing.

Example 22

Process Flow Diagram of Certification Run to Isolate Protein from *Lemna*

Figure 38:
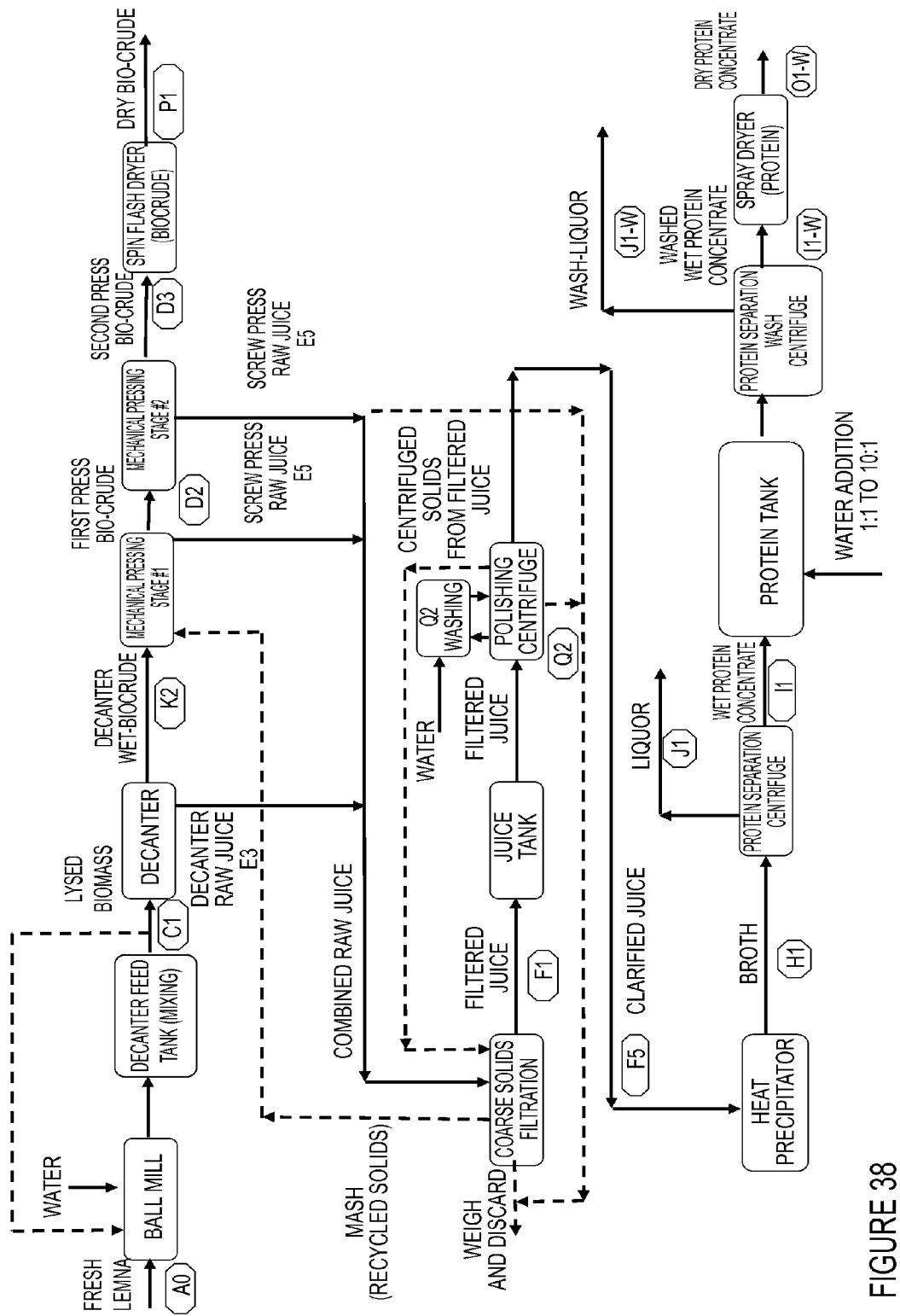
FIG. 38 is a flow diagram illustrating an exemplary process of isolating protein and other products from fresh lemna.

FIG. 38 shows a flow diagram of an exemplary certification run to isolate protein from an aquatic species, e.g., fresh lemna. The process was tested by experiments.

Fresh lemna (also referred to as biomass slurry or raw feedstock) are conveyed to a ball mill where the wet biomass fronds are mixed with water and lysed to expose the internal water and protein. The lysed biomass is conveyed to a decanter feed tank for the mixing step. The lysed biomass is conveyed to a decanter which generates a decanter raw juice and decanter wet-biocrude. The decanter wet-biocrude is conveyed to a mechanical pressing stage #1 to generate a raw juice and a first press bio-crude. The first press bio-crude is conveyed to mechanical pressing stage #2 to generate a screw press raw juice and a second press bio-crude. The second press bio-crude is collected for drying using a biocrude dryer (a spin flash dryer) to generate a dry biocrude.

The decanter raw juice, the screw press raw juice from mechanical pressing stage #1, and the screw press raw juice from mechanical pressing stage #2 are combined to form a combined raw juice and fed to a coarse solids filtration container in which the combined raw juice is filtered to generate a mash comprising recycled solids and filtered juice. The mash is fed to mechanical pressing stage #1. The filtered juice is stored in the juice tank. Filtered juice from the juice tank is clarified using a polishing centrifuge and washed with water to generate centrifuged solids from the filtered juice and a clarified juice. The clarified juice is conveyed to a heat precipitator to cause heat-induced protein coagulation, generating a broth comprising a wet protein concentrate. In order to separate the protein from the remaining part of the broth, the broth is centrifuged to generate a liquor and a wet protein concentrate. The liquor is recycled back to the growth ponds (also referred to as bioreactors). In other embodiments, the liquor is discarded. The wet protein concentrate is washed in the protein tank by adding water (1:1 to 10:1) to the wet protein concentrate to form a wet protein concentrate wash. The protein is separated in a centrifuge to generate a wash-liquor, which is recycled back to the growth ponds (also referred to as bioreactors). In other embodiments, the wash liquor is discarded. The resulting wet protein concentrate wash is dried using a protein dryer (spray dryer) to generate a dry protein concentrate.

In FIG. 38, each block arrow indicates a process stream, each dashed arrow indicates a recycled stream; each dotted arrow indicates a discarded stream; and each letter or letter/number combination within a hexagon indicates a sampling location or a material ID. A0, P1, and O1-W indicate samples that are taken for internal and external analysis. C1, K2, D2, D3, F5, Q2, J1, J1-W, I1, and I1-W indicate samples that are taken for internal analysis.

Example 23

*Lemna* Growth and Processing Facility

A process of growing and harvesting lemna is described in this example. The process was tested by experiments.

a. Raceway Bioreactors

The facility is designed to utilize multiple Raceway Bioreactors. Each Raceway is lined with LDPE (30 mil) plastic over a geomembrane (8 oz). A windbreak of PE material provides protection from wind.

The water supply to the Raceway is delivered via the Return Pumps originating from the Primary Holding Pond. Alternate water supply is discussed in the Water Supply & Storage section below. Overall water flow into each Raceway is monitored. Water flow into each Raceway harvest is automatically controlled.

Several alternatives exist to deliver water to a Raceway using automated valves controlled by the Central PLC. The water supply may be directed through the pair of Rainmaker distribution pipes, the paddlewheel Blade Cleaner distribution pipe, or the Water Manifold distribution pipe. In the rainmaker, blade cleaner, and water manifold, the flow rate is controlled. The water supply may be directed through the underwater Clean Suction/Irrigation distribution pipe.

In some embodiments, the raceway circulation is directed through the Paddlewheel. The Paddlewheel is located at the outside turnaround end of each raceway, which is the operating end. The Paddlewheel rotational speed is controlled by a variable frequency drive (VFD), and the surface velocity is automatically controlled.

*Lemna* is harvested from the growth raceway by submerged Harvest Skimmers. Two Skimmer Modules are installed in each Raceway. The first is located downstream of the outside turnaround near the Paddlewheel. The second is located downstream of the inside turnaround. Skimmers are constructed of PVC piping installed in submerged concrete boxes. A harvest cycle consists of harvesting through each Raceway's pair of Harvest Skimmers. During a harvest cycle, skimmers are raised to the surface of the pond by a linear actuator and mechanical linkage. Harvest is achieved by drawing suction through the skimmer piping with one of the two parallel Mat Harvest Pumps. Harvested lemna is pumped to the Processing Building for processing into the various products, including, but not limited to, protein concentrate, bio-crude, and lemna (animal) meal. Flow through the Mat Harvest Pump is controlled by actuating the Skimmer Flow Valves to meet the set point for FIC-141. The two Mat Harvest Pumps serve all three Raceways. The pumps are located at the Harvest Station on the operating end of the Raceways.

Biomass detritus is harvested from the Raceway floor by the underwater harvest system. Underwater harvest flow is achieved by drawing suction with the Underwater Harvest Pump. Biomass detritus is pumped to the Processing Building for processing with the skimmer harvest. Underwater harvest is operated continuously from all three Raceways. During underwater harvest, the flow is monitored and totalized by computer function. Underwater harvest is drawn from a Raceway using automated valves controlled by the Central PLC (programmable logic controller). Alternatively, underwater harvest may be directed from underwater harvest screen boxes in each Raceway, or from underwater suction piping in each Raceway.

Raceway water analysis and instrumentation is performed by monitoring water level and water temperature. The Raceway water level is monitored, and alarms notify the PLC when the high or low alarm set points are reached. Control of water level may be performed with or without automation. The Raceway water temperature is also monitored, and alarms notify the PLC when the high or low alarm set points are reached. Control of water temperature may be performed with or without automation.

In the Automated Sampling System, the Analytical Sampling Pump can draw water from any of the three Raceways by opening the sampling valve. The Sampling Pump discharge is run through the Sample filter to remove particles of specific sizes.

Raceways are protected from overflow during a severe rain event by a passive system located at the overflow end of each raceway. A gooseneck positioned at a height below the raceway wall height allows water to be discharged.

Water Supply and Storage

Supply water can be supplied to the facility by the water supply pumps or by the well water pump. Surface or well water is pumped through the supply water screeners to remove particles of a specific size. Screened water is run through supply water sand filters and conveyed to the Growth & Harvest system. Water reclaimed from the process is drained by gravity from the reclaimed water tanks in the process building to the raceways and holding ponds.

In the Water Return System, the return pumps deliver water from the primary holding pond to the raceways and process building. Alternatively, the return pumps can draw suction from the secondary holding pond and deliver to the facility or to the primary holding pond. Return water is pumped through the supply water screeners to remove particles of a specific size.

The secondary holding pond is utilized as a process water reservoir to supplement the primary holding pond as needed. Water can be transferred from the Primary Holding Pond and the Raceways by gravity.

c. Nutrient System

The Nutrient System consists of a pair of Nutrient Tanks in which a nutrient solution is blended in batches that are delivered to the Raceways. Nutrient blending is a semi-automated process by which Supply Water is metered to the Nutrient Tanks. The operator utilizes automated valves to fill the Nutrient Tank. Dry nutrient blend is added either manually or automatically according the desired dosing concentration. As the dry nutrient blend is added, the Nutrient Pumps recirculate the Supply Water in the Nutrient Tanks.

As the Raceways are filled for commissioning and start-up, an initial dose of nutrient is delivered. Maintenance-level doses of nutrient are required on a regular basis to maintain the desired nutrient concentration in the water in the Raceways. Each dose is a blend of nutrients at a concentration that will maintain the desired nutrition levels. Once a nutrient solution is blended and a Nutrient Tank contains a prepared solution, the delivery process is semi-automated. Either Nutrient Pump can deliver a dose to any Raceway by use of automated valves.

*Lemna* Processing a. Dewatering and Screening

*Lemna* harvested through the Harvest Skimmers by the Mat Harvest Pumps is dewatered by the Harvested *Lemna* Screener, which is a two-deck screener that separates oversized material and debris from the lemna. Detritus is removed from the Raceways by the Underwater Harvest Pump and is screened by the Underwater Harvest Screener. Raceway harvest water from both screeners is collected in the Reclaimed Water Tanks, which are two horizontal tanks mounted on an elevated platform located directly below the screener mezzanine deck. The Reclaimed Water Tanks are hydraulically linked to effectively combine their volume and accommodate the flow of reclaimed water from both screeners. The tanks also serve the following smaller volume process discharge streams: Waste press juice from Screw Press #3, Liquor from the Protein Broth Centrifuge, Liquor from the Washed Protein Centrifuge, and Recycled cooling water from the Juice Cooler. The tanks drain by gravity through a PVC pipe into the Primary Holding Pond. When a high level is reached, a high level switch will alarm and interlock to shut down the Mat Harvest Pumps and the Underwater Harvest Pump. For lemna harvest rate measurement, harvested lemna from the Harvested *Lemna* Screener and detritus from the Underwater Harvest Screener drop onto the Weigh Belt Feeder to be metered by a load cell conveyed in to processing.

Dewatered *Lemna* Surge Hopper

The Dewatered *Lemna* Surge Hopper is a rectangular steel hopper with the size chosen to accommodate the specific number of raceways in production. The Dewatered *Lemna* Surge Hopper is a live-bottom hopper emptied by a screw conveyor which delivers harvested lemna to milling. The conveyor rotational speed is controlled by VFD to match the flow of the downstream milling process.

c. *Lemna* Milling

The Ball Mill Feeder receives flow from the Dewatered *Lemna* Surge Hopper Conveyor and controls flow into the Ball Mill. *Lemna* is milled into mash by the Ball Mill and is discharged into the Mash Mix Tank. The desired total solids concentration of milled mash is optimized to facilitate processing in the *Lemna* Decanter. The Ball Mill Feeder can accept flow from recycled stream from the Mash Mix Tank, Protein Juice from the liquid receiver of the *Lemna* Decanter, and water from the Process Building header. Milled lemna mash is held in the Mash Mix Tank, an agitated tank with a capacity to hold all of the anticipated total daily harvest of dewatered lemna from all Raceways.

d. *Lemna* Decanting

The feed rate to the *Lemna* Decanter is controlled by the Mash Pump VFD. All automated functions within the *Lemna* Decanter Skid are controlled by the *Lemna* Decanter Skid Control Panel. The Bio-Crude Solids output from the decanter initiates the Bio-Crude processing stream. Bio-Crude is transferred from the decanter discharge to the Bio-Crude Pressing Unit by the Wet Bio-Crude Conveyor. The liquid output from the decanter initiates the Protein processing stream. Protein Juice falls from the decanter to the Juice Receiver, and is delivered from the receiver to the Juice Screener by the Juice Pump. The recycled streams, which include Press Juice from Screw Press #1, Press Juice from Screw Press #2, and pulp from the Polishing Centrifuge, are also conveyed to the Juice Receiver. The combined Protein Juice and recycle streams from the Juice Receiver are delivered to the Juice Filter by the Juice Pump. The suspended solids from the Protein Juice stream are screened through the Juice Filter. Solids are discharged from the Juice Filter directly into the Wet Bio-Crude Conveyor for delivery to Bio-Crude Pressing. Juice is discharged to the Filtered Juice Tank and is transferred to Juice Tank #1 by the Filtered Juice Pump.

Bio-Crude Processing a. Bio-Crude Pressing

Screw Press #1

The Bio-Crude stream from the *Lemna* Decanter is dewatered in preparation for drying by a series of screw presses. Screw Press #1 is the first stage. Anticipated daily production of the Bio-Crude first pressing will vary based on the number of bioreactors and the size of the processing center.

Screw Press #2

Bio-Crude is further dewatered after being directly discharged from Screw Press #1 into Screw Press #2. Anticipated daily production of the Bio-Crude second pressing will vary based on the number of bioreactors and the size of the processing facility.

Press Juice Recovery

The combined Press Juice from Screw Press #1 and Screw Press #2 is conveyed to the Press Juice Receiver. Recovered Press Juice is recycled back to the Wet Bio-Crude Conveyor by the Press Juice Pump.

Screw Press #3

Bio-Crude is further dewatered after being directly discharged from Screw Press #2 into Screw Press #3. Optional adjustments include injecting steam into Screw Press #3. Anticipated daily production of the Bio-Crude third pressing will vary based on the number of bioreactors and the size of the processing facility. Pressed Bio-Crude is discharged from Screw Press #3 into the Bio-Crude Conveyor, which delivers the Bio-Crude to the Pressed Bio-Crude Hopper.

Waste Press Juice Reclamation

Press Juice from Screw Press #3 is conveyed to the Waste Juice Receiver. Waste Juice is pumped by the Waste Juice Pump to the Reclaimed Water Tanks for return to the Primary Holding Pond.

Bio-Crude Drying

The Pressed Bio-Crude Hopper has a nominal capacity of 125% of the anticipated total daily production of Pressed Bio-Crude. Daily production is held in the hopper until the following operating day, when it is dried and packaged. Pressed Bio-Crude is transferred by the Pressed Bio-Crude Conveyor to the Dryer Feed Hopper at a rate controlled by VFD to maintain an operating level in the Bio-Crude Dryer Feed Hopper.

The Pressed Bio-Crude is dried by the Bio-Crude Dryer. In some embodiments, the Bio-Crude Dryer is a spin-flash dryer with intake heated by an Air Heater fired by natural gas. Liquified natural gas (LNG) tanks are located on site for burner supply. Dried Bio-Crude is discharged into a product hopper and transferred to the packaging room. Automated functions within the scope of the Bio-Crude Dryer Skid are controlled by a dedicated control panel.

c. Bio-Crude Packaging

The packaging area is climate controlled area to reduce humidity effects on the Bio-Crude product. Bio-Crude is packaged in appropriate product-specific bags, fiber drums, or other containers.

iv. Protein Concentrate Processing a. Polishing Centrifugation

Juice Polishing

Residual solids are removed for Filtered Protein Juice by the Polishing Centrifuge.

Pulp Recycle

The solids discharged from the Polishing Centrifuge are conveyed to the Decanter Juice Receiver, where the solids are recycled into the Juice Filter and Wet *Lemna* Conveyor.

Protein Precipitation

Steam Injection Precipitation

Liquid proteins in the Polished Juice are precipitated for separation by the Steam Injection Precipitator.

c. Protein Broth Centrifugation

Concentrated Protein Broth

The Protein Broth is concentrated by the Protein Broth Centrifuge. The Broth is fed to the Protein Broth Centrifuge by the Broth Holding Tank Pump.

Liquor Reclamation

The complementary phase from the Protein Broth Centrifuge is the liquor phase. Liquor is discharged to the Reclaimed Water Tanks for return to the Primary Holding Pond.

d. Protein Broth Washing & Centrifugation

Concentrated Protein Broth is washed to further concentrate the precipitated protein solids. Prior to the Broth Wash Tank, the concentrated broth is mixed with wash water. The Washed Broth is conveyed to the Washed Broth Centrifuge. The Broth is fed to the Wash Centrifuge by the Broth Wash Pump. The Washed Broth is separated from wash water by the Wash Centrifuge. The Washed Broth is conveyed from the centrifuge to the Protein Tank. The flow rate is monitored and sent to the Wash Centrifuge Control Panel. Anticipated daily production of Washed Broth varies based on the number of bioreactors and the size of the processing facility. The liquor phase separated in the Wash Centrifuge is conveyed to the Reclaimed Water Tanks for return to the Primary Holding Pond.

e. Protein Drying

The Protein Tank has a nominal of 125% of the anticipated total daily production of Washed Protein Concentrate. The Protein Tank is equipped with a chilled water jacket to maintain the temperature of the contents at the desired temperature. Daily production is held in the tank until it is dried and packaged. The Concentrated Protein is dried by the Protein Dryer. In some embodiments, the Protein Dryer is a spray dryer with intake heated by an Air Heater fired by natural gas. Liquified natural gas (LNG) tanks are located on site for burner supply. Anticipated daily production of Dry Protein Concentrate will vary based on the number of bioreactors and the size of the processing facility. The Dried Protein Concentrate is conveyed to a product hopper and transferred to the packaging room.

f. Protein Packaging

The packaging area is climate controlled to reduce humidity effects on the Protein Concentrate product. The Protein Concentrate is packaged in appropriate product-specific bags or fiber drums.

v. Process Liquid Chilling and Holding a. System Design Intent

The Process Liquid Chilling & Holding System is designed to preserve partially processed mash, juice or broth during a process upset. The following process locations can transfer partially processed product to or from the Chilling & Holding System: Filtered Juice, Polished Juice, Precipitated Broth, Concentrated Broth, and Washed Broth.

System Components

Primary Cooling

Process fluids from Filtered Juice, Polished Juice, Precipitated Broth, Concentrated Broth, and Washed Broth pass through the Juice Cooler to set or maintain the temperature at the desired level.

Chilling

Process fluids exiting the Juice Cooler also pass through the Juice Chiller to set or maintain the temperature at the desired level. The chilling fluid supply is generated by the Water Chiller Skid, which operates in a closed loop. The temperature of the process fluid exiting the Juice Chiller is controlled.

Holding Tank

The Chilled Juice Tank has a nominal capacity of 100% of the anticipated total daily production Milled *Lemna* Mash. The Chilled Juice Tank is equipped with a chilled water jacket to maintain the temperature of the contents at the desired set point.

vi. Clean-In-Place (CIP) System a. CIP Skid

The CIP Skid is equipped with two tanks sized appropriately for the volume of material being processed. The CIP Rinse Tank normally contains hot water used to rinse process equipment before and after cleaning with caustic solution, and a caustic solution used to clean process equipment by recirculation. The CIP Pump is a centrifugal pump that delivers CIP solution and rinse to CIP system users. The CIP Heater warms CIP solutions to the desired temperature. Flow can be recirculated through the CIP Heater and either of the two CIP tanks to reach the desired temperature set point.

b. CIP Solution & Rinse

The CIP solution is a caustic solution heated to a desired set point. The solution is prepared by dilution with the appropriate amount of water. The CIP rinse refers to clean water heated to the designated set point.

c. CIP Supply & Return

The CIP System Users are as follows: Mash Mix Tank, Juice Tank #1, Polishing Centrifuge, Broth Holding Tank, Protein Broth Centrifuge, Broth Wash Tanks, Wash Centrifuge, Juice Cooler, Juice Chiller, Chilled Juice Tank, and Protein Tank.

Example 24

Protein Purity, Protein Product Yield, and Biocrude Product Yield

Dry protein concentrate and dry bio-crude were produced according to the Process Flow Diagram shown in FIG. 38 and described herein.

Summarized in Table 6 are protein purity, protein product yield, and biocrude product yield. As used herein and described elsewhere in the application, protein purity is calculated as a percentage of total final product dry substance, protein yield is calculated as a percentage of total input dry substance mass, and biocrude yield is calculated as a percentage of total input dry substance mass.

TABLE 6

Product Yields

|  | Day I | Day II | Day III |
|---|---|---|---|
| Protein Purity | 67.7% | 69.9% | 69.1% |
| Protein Product Yield | 23.2% | 20.3% | 21.6% |
| Biocrude Product Yield | 43.7% | 47.6% | 37.9% |

The dry protein concentrate and dry bio-crude were analyzed further.

Example 25

Process Product Yields

Summarized in Table 7 are typical yield ranges of the protein, bio-crude, and lemna meal.

TABLE 7

Process Product Yields
Process Product Yields

| Product | Typical Yield Range |
|---|---|
| Protein | 15%-28% |
| Bio-Crude | 30%-52% |
| *Lemna* Meal | 32%-55% |

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

STATEMENT OF EXEMPLARY EMBODIMENTS OF INVENTION

Some embodiments of the invention are disclosed in the following items.

Items

1. A process of recovering multiple products from biomass of an aquatic species comprising:
   providing the biomass;
   lysing the biomass to generate a lysed biomass;
   separating the lysed biomass to generate a juice and a first solid phase;
   forming a wet protein concentrate using the juice;
   drying the wet protein concentrate to generate a dry protein concentrate;
   producing a wet bio-crude using the first solid phase,
   drying the wet bio-crude to generate at least one product selected from a dry bio-crude and a carbohydrate-rich meal,
   wherein the multiple products comprise products selected from the dry protein concentrate, dry bio-crude, and carbohydrate-rich meal, and
   wherein at least 50% of the protein in the multiple products is in the dry protein concentration.
2. The process of item 1, wherein the providing step comprises:
   producing the biomass of an aquatic species on an industrial scale; and
   harvesting the biomass.
3. The process of item 1, wherein the separating step comprises pressing the lysed biomass.
4. The process of item 1, further comprising:
   filtering the juice to generate a filtered juice and a second solid phase;
   clarifying the filtered juice to generate a clarified juice and a third solid phase;
   coagulating protein from the clarified juice to generate a broth comprising the wet protein concentrate; and
   separating the wet protein concentrate from the broth.
5. The process of item 4, wherein at least one of: the first solid phase, the second solid phase, the third solid phase, and the broth, is/are used to recover the bio-crude and the carbohydrate-rich meal.
6. The process of item 1, wherein the aquatic species comprises a species of *Lemna*.
7. The process of item 1, wherein the lysing comprises using at least one of: a ball mill a colloid mill, a knife mill, a hammer mill, a grinding mill, a puree machine, and a filter press.
8. The process of item 3, wherein the pressing comprises using at least one of a belt press, a fan press, a rotary press, a screw press, a filter press, and finisher press.
9. The process of item 1, wherein the juice comprises soluble protein.
10. The process of item 4 comprising pressing at least one of the first solid phase, the second solid phase, or the third solid phase to generate a second juice and a bio-crude.
11. The process of item 10, wherein the second juice is combined with the juice.
12. The process of item 10, wherein the further pressing is carried out using a screw press.
13. The process of item 10, further comprising drying the bio-crude.
14. The process of item 13, wherein the drying is carried out using at least one of: a spin flash dryer, a spray dryer, a drum dryer, a flash dryer, a fluid bed dryer, a double drum dryer, and a rotary dryer.
15. The process of item 4, wherein the filtering is carried out using at least one of: a vibratory separator, a vibrating screen filter, a circular vibratory separator, a linear/inclined motion shaker, a decanter centrifuge, and a filter press.
16. The process of item 15, wherein the vibratory separator comprises at least one vibrating screen filter.
17. The process of item 4, wherein the clarifying comprises centrifuging and/or further filtration of the filtered juice.
18. The process of item 17, wherein the clarifying comprises use of at least one of a high-speed multi disc stack centrifuge, microfiltration and ultrafiltration.
19. The process of item 4, wherein the clarified juice is stored in a chilled storage tank.
20. The process of item 4, wherein the coagulating comprises lowering the pH of the clarified juice.
21. The process of item 20, wherein the pH is lowered to below about 6.
22. The process of item 20, wherein the pH is lowered to below about 5.
23. The process of item 20, wherein the pH is lowered to about 4.5.
24. The process of item 20, wherein lowering the pH comprises using at least one acid selected from hydrochloric acid, nitric acid, and sulfuric acid.
25. The process of item 4, wherein the coagulating is carried out using a precipitator comprising at least one heat exchanger.
26. The process of item 25, wherein the at least one heat exchanger comprises at least one plate, or tube or steam injection heat exchanger.

27. The process of item 4, wherein the coagulating comprises heating the clarified juice to a first temperature to generate a broth; and
cooling the broth to a second temperature.

28. The process of item 27, wherein the first temperature is from about 40° C. to about 100° C.

29. The process of item 27, wherein the second temperature is below about 40° C.

30. The process of item 27, wherein the second temperature is below about 30° C.

31. The process of item 1, wherein the separating comprises using a high speed multi-disk stack centrifuge.

32. The process of item 1, wherein the wet protein concentrate is stored in a chilled storage tank.

33. The process of item 1, further comprising drying the wet protein concentrate to generate a dry protein concentrate.

34. The process of item 33, wherein the drying is carried out using a spray dryer, a drum dryer, spin flash dryer, a flash dryer, a fluid bed dryer, a double drum dryer, and a rotary dryer.

35. The process of item 1, further comprising contacting a material selected from the group consisting of the third solid phase and the clarified juice with at least one of: an alcohol, a solvent, or water, and with an acid catalyst, to form a mixture, separating the mixture into a liquid and a solid, whereby lipids and ash-forming components in the material are segregated into the liquid.

36. The process of item 1, further comprising, either before or directly after the lysing, washing the biomass using an aqueous solvent.

37. A system of recovering multiple products from biomass of an aquatic species comprising:
a lysing unit for lysing the biomass to generate a lysed biomass;
a separating unit for separating the lysed biomass to generate a juice and a solid phase;
a unit for forming a wet protein concentrate using the juice;
a protein drying unit for drying the wet protein concentrate to generate a dry protein concentrate; and
a unit for drying a wet bio-crude to generate at least one product selected from a dry bio-crude and carbohydrate-rich meal, wherein the wet bio-crude comprises the solid phase;
wherein the multiple products comprise products selected from the dry protein concentrate, dry bio-crude, and carbohydrate-rich meal, and
wherein at least 50% of the protein in the multiple products is in the dry protein concentration.

38. The system of item 37, wherein the lysing unit comprises at least one apparatus selected from a colloid mill, knife mill, ball mill, hammer mill, grinding mill, puree machine, and filter press.

39. The system of item 37, wherein the separating unit comprises at least one apparatus selected from a belt press, decanter centrifuge, fan press, rotary press, screw press, filter press, and finisher press.

40. The system of item 37, wherein the unit for forming the wet protein concentrate using the juice comprising at least one unit selected from a filtering unit, a clarifying unit, a protein coagulation unit, and a protein collection unit.

41. The system of item 40, wherein the filtering unit comprises at least one apparatus selected from a vibratory separator, vibrating screen filter, circular vibratory separator, linear/inclined motion shaker, decanter centrifuge, filter press.

42. The system of item 40, wherein the clarifying unit comprises at least one apparatus selected from a high-speed disc stack centrifuge, microfiltration, ultra-filtration.

43. The system of item 40, wherein the protein coagulation unit comprises at least one apparatus selected from a heat precipitator and acid precipitation apparatus.

44. The system of item 40, wherein the protein collection unit comprises at least one apparatus selected from a high speed multi-disk stack centrifuge, settling tank, clarifier, and decanter centrifuge.

45. The system of item 37, wherein the protein drying unit comprises at least one apparatus selected from a spray dryer, double drum dryer, and flash dryer.

46. The system of item 37, wherein the unit for drying the bro-crude comprises at least one apparatus selected from a fluid bed dryer, spin flash dryer, flash dryer, drum dryer, and rotary dryer.

47. The system of item 37 further comprising a sanitizing unit.

We claim:

1. A process of recovering multiple products from biomass of an aquatic species comprising:
providing the biomass;
lysing the biomass to generate a lysed biomass;
separating the lysed biomass to generate a juice and a first solid phase;
filtering the juice to generate a filtered juice and a second solid phase;
clarifying the filtered juice to generate a clarified juice and a third solid phase;
coagulating protein from the clarified juice to generate a broth comprising the wet protein concentrate;
separating the wet protein concentrate from the broth;
drying the wet protein concentrate to generate a dry protein concentrate;
producing a wet bio-crude using the first solid phase;
drying the wet bio-crude to generate at least one product selected from a dry bio-crude and a carbohydrate-rich meal;
wherein the multiple products comprise products selected from the dry protein concentrate, dry bio-crude, and carbohydrate-rich meal; and
wherein at least 50% of the protein in the multiple products is in the dry protein concentration.

2. The process of claim 1, wherein the providing step comprises:
producing the biomass of an aquatic species on an industrial scale; and
harvesting the biomass.

3. The process of claim 1, wherein the separating step comprises pressing the lysed biomass.

4. The process of claim 3, wherein the pressing comprises using at least one of a belt press, a fan press, a rotary press, a screw press, a filter press, and finisher press.

5. The process of claim 1, wherein at least one of: the first solid phase, the second solid phase, the third solid phase, and the broth, is/are used to recover the bio-crude and the carbohydrate-rich meal.

6. The process of claim 1, wherein the aquatic species comprises a species of *Lemna*.

7. The process of claim 1, wherein the lysing comprises using at least one of: a ball mill a colloid mill, a knife mill, a hammer mill, a grinding mill, a puree machine, and a filter press.

8. The process of claim 1, wherein the juice comprises soluble protein.

9. The process of claim 1 comprising pressing at least one of the first solid phase, the second solid phase, or the third solid phase to generate a second juice and a bio-crude.

10. The process of claim 9, wherein the second juice is combined with the juice.

11. The process of claim 9, wherein the further pressing is carried out using a screw press.

12. The process of claim 9, further comprising drying the bio-crude.

13. The process of claim 12, wherein the drying is carried out using at least one of: a spin flash dryer, a spray dryer, a drum dryer, a flash dryer, a fluid bed dryer, a double drum dryer, and a rotary dryer.

14. The process of claim 1, wherein the filtering is carried out using at least one of: a vibratory separator, a vibrating screen filter, a circular vibratory separator, a linear/inclined motion shaker, a decanter centrifuge, and a filter press.

15. The process of claim 14, wherein the vibratory separator comprises at least one vibrating screen filter.

16. The process of claim 1, wherein the clarifying comprises centrifuging and/or further filtration of the filtered juice.

17. The process of claim 16, wherein the clarifying comprises use of at least one of a high-speed multi disc stack centrifuge, microfiltration and ultrafiltration.

18. The process of claim 1, wherein the clarified juice is stored in a chilled storage tank.

19. The process of claim 1, wherein the coagulating comprises lowering the pH of the clarified juice.

20. The process of claim 19, wherein the pH is lowered to below about 6.

21. The process of claim 19, wherein the pH is lowered to below about 5.

22. The process of claim 19, wherein the pH is lowered to about 4.5.

23. The process of claim 19, wherein lowering the pH comprises using at least one acid selected from hydrochloric acid, nitric acid, and sulfuric acid.

24. The process of claim 1, wherein the coagulating is carried out using a precipitator comprising at least one heat exchanger.

25. The process of claim 24, wherein the at least one heat exchanger comprises at least one plate, or tube or steam injection heat exchanger.

26. The process of claim 1, wherein the coagulating comprises heating the clarified juice to a first temperature to generate a broth; and cooling the broth to a second temperature.

27. The process of claim 26, wherein the first temperature is from about 40° C. to about 100° C.

28. The process of claim 26, wherein the second temperature is below about 40° C.

29. The process of claim 26, wherein the second temperature is below about 30° C.

30. The process of claim 1, wherein the separating comprises using a high speed multi-disk stack centrifuge.

31. The process of claim 1, wherein the wet protein concentrate is stored in a chilled storage tank.

32. The process of claim 1, further comprising drying the wet protein concentrate to generate a dry protein concentrate.

33. The process of claim 32, wherein the drying is carried out using a spray dryer, a drum dryer, spin flash dryer, a flash dryer, a fluid bed dryer, a double drum dryer, and a rotary dryer.

34. The process of claim 1, further comprising contacting a material selected from the group consisting of the third solid phase and the clarified juice with at least one of: an alcohol, a solvent, or water, and with an acid catalyst, to form a mixture, separating the mixture into a liquid and a solid, whereby lipids and ash-forming components in the material are segregated into the liquid.

35. The process of claim 1, further comprising, either before or directly after the lysing, washing the biomass using an aqueous solvent.

* * * * *